US009554525B2

(12) United States Patent
Wu et al.

(10) Patent No.: US 9,554,525 B2
(45) Date of Patent: Jan. 31, 2017

(54) AGRONOMICALLY ELITE SOYBEANS WITH HIGH β-CONGLYCININ CONTENT

(71) Applicant: Monsanto Technology LLC, St. Louis, MO (US)

(72) Inventors: Kunsheng Wu, Ballwin, MO (US); Thomas Horejsi, Ames, IA (US); Joseph R. Byrum, West Des Moines, IA (US); Neal Bringe, Elizabeth, CO (US); Julie Yang, Bridgeton, MO (US); Donghong Pei, Northfield, MN (US); Robert Reiter, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 293 days.

(21) Appl. No.: 14/106,707

(22) Filed: Dec. 13, 2013

(65) Prior Publication Data

US 2014/0259196 A1 Sep. 11, 2014

Related U.S. Application Data

(62) Division of application No. 11/517,186, filed on Sep. 7, 2006, now abandoned.

(60) Provisional application No. 60/722,493, filed on Sep. 30, 2005, provisional application No. 60/714,779, filed on Sep. 7, 2005.

(51) Int. Cl.

*A01H 1/04* (2006.01)
*A01H 5/10* (2006.01)
*C12Q 1/68* (2006.01)

(52) U.S. Cl.

CPC *A01H 1/04* (2013.01); *A01H 5/10* (2013.01); *C12Q 1/6895* (2013.01); *C12Q 2600/13* (2013.01); *C12Q 2600/156* (2013.01); *C12Q 2600/172* (2013.01)

(58) Field of Classification Search

None

See application file for complete search history.

(56) References Cited

U.S. PATENT DOCUMENTS

| | | | | |
|---|---|---|---|---|
| 6,171,640 | B1 | 1/2001 | Bringe | |
| 6,566,134 | B2 | 5/2003 | Bringe | |
| 7,094,751 | B2 * | 8/2006 | Bringe ................. | A23C 11/103 426/656 |
| 7,186,425 | B2 | 3/2007 | Kohno et al. | |
| 2004/0037905 | A1 | 2/2004 | Bringe | |
| 2005/0138681 | A1 | 6/2005 | Takahashi et al. | |
| 2006/0062894 | A1 | 3/2006 | Smith et al. | |

FOREIGN PATENT DOCUMENTS

| | | |
|---|---|---|
| EP | 1 323 425 | 9/2001 |
| JP | 2005-206545 | 8/2005 |
| WO | WO 00/19839 | 4/2000 |
| WO | WO 2004/006659 | 1/2004 |
| WO | WO 2006/010049 | 1/2006 |
| WO | WO 2006/039136 | 4/2006 |

OTHER PUBLICATIONS

Csanadi et al. Seed quality QTLs identified in molecular map of early maturing soybean. (2001) Theor. Appl. Genet.; vol. 103; pp. 912-919.*

Ritchie et al. Targeting Induced Local Lesions in Genomes—TILLING (2004) Legume Crop Genetics; pp. 194-203.*

Jander et al (2003) Plant Physiology; vol. 131; pp. 139-146.*

Beilinson et al., "Genomic organization of glycinin genes in soybean," *Theor. Appl. Genet.*, 104:1132-1140, 2002.

Chen et al., "Four genes affecting seed traits in soybeans map to linkage Group F," *J. Hered.*, 89(3):211-215,1998.

De Moraes et al., "Assisted selection by specific DNA markers for genetic elimination of the Kunitz trypsin inhibitor and lectin in soybean seeds," *Euphytica*, 149:221-226, 2006.

Diers et al., "Genetic mapping of the Gy4 and Gy5 glycinin genes in soybean and the analysis of a variant of Gy4," *Theor. Appl. Genet.*, 89:297-304, 1993.

Hajika et al., "A line lacking all the seed lipoxygenase isozymes in soybean [*Glycine max* (L.) *Merrill*] induced by gamma-ray irradiation," *Jpn J. Breed.*, 41:507-509, 1991.

Hao et al., "Effects of lipoxygenase null genes of soybean in controlling beany-flavor of soymilk and soyflour," *Agricultural Sciences in China*, 1:965-971, 2002.

Harada et al., "Genetic analysis of the most acidic 11S globulin subunit and related characters in soybean seeds," *Japan J. Breed.*, 33:23-30, 1983.

Natarajan et al., "Characterization of storage proteins in wild (*Glycine soja*) and cultivated (*Glycine max*) soybean seeds using proteomic analysis," *J. Agric. Food Chem.*, 54(8):3114-3120, 2006.

Nielsen et al., In: Cellular and Molecular Biology of Plant Seed Development, Larkins et al. (Eds.), Kluwer Academic Publishers, Dordrecht, The Netherlands, pp. 151-220, 1997.

Nielsen et al., "Characterization of the glycinin gene family in soybeans," *The Plant Cell*, 1:313-328, 1989.

Shibata et al., "Primary structure of soybeans lipxygenase L-2," *J. Biol. Chem.*, 263:6816-6821, 1987.

Shibata et al., "Primary structure of soybeans lipoxygenase-1," *J. Biol. Chem.*, 262:10080-10085, 1987.

Wilson, In: *Lipoxygenase and Lipoxygenase Pathway Enzymes*, Piazza (Ed.), 209-225, 1996.

Yenofsky et al., "Isolation and characterization of a soybean (*Glycine max*) lipoxygenase-3 gene," *Mol. Gen. Genet*, 211:215-222, 1988.

(Continued)

*Primary Examiner* — Cathy Kingdon Worley

(74) *Attorney, Agent, or Firm* — Dentons US LLP; Chunping Li Esq.

(57) ABSTRACT

The invention overcomes the deficiencies of the art by providing an agronomically elite soybean plant with non-transgenic mutations of at least two of the glycinin subunits selected from the group consisting of Gy1, Gy2, Gy3, Gy4, and Gy5, such as conferring a Gy2 and Gy4 null phenotype and increased β-conglycinin content in seed. The invention also provides derivatives, and plant parts of these plants and uses thereof. Methods for marker assisted selection of soybean varieties comprising non-transgenic mutations conferring a reduced Gy1, Gy2, Gy3, Gy4, and Gy5 phenotype are also provided as part of the current invention. Methods for producing such plants that are further lipoxygenase and/or Kunitz Trypsin Inhibitor null and the plants produced thereby are also provided. The invention is significant in that soybeans from such plants are preferred dietary additives and provide important health benefits.

28 Claims, 9 Drawing Sheets

(56) References Cited

OTHER PUBLICATIONS

Cho et al., Inheritance and organization of glycinin genes in soybeans, *The Plant Cell*, 1:329-337, 1989.
Nishiba et al., "Degradation of vitamin E, vitamin C, and lutein in soybean homogenate: a comparison of normal soybeans and lipoxygenase-lacking (triple-null) soybean" *J. Agric. Food Chem.*, 46:3708-3712, 1998.
Takahashi et al., "Accumulation of high levels of free amino acids in soybean seeds through integration of mutations conferring seed protein deficiency," *Planta*, 217:577-586, 2003.
Yagasaki et al., Inheritance of glycinin subunits and characterization of glycinin molecules lacking the subunits in soybean (*Glycine max* (L.) *Merr.*), *Breeding Science*, 46:11-15, 1996.
Krishnan, "Engineering soybean for enhanced sulfur amino acid content," *Crop Sci.*, 45:454-461, 2005.
Henikoff et al. TILLING. Traditional mutagenesis meets functional genomics. *Plant Physiology*, 135:630-636, 2004.
Scallon et al., "Characterization of a null-allele for the $Gy_4$ glycinin gene from soybean," ., *Mol. Gen. Genet*. 208:107-113, 1987.
Yagasaki et al., "Growth Habit and Tofu Processing Suitability of Soybeans with Different Glycinin Subunit Composition," The Hokuriku Crop Science 34:126-128, 1999 (English summary).
Office Action regarding Chinese Application No. 201310711601.9, dated Sep. 8, 2016.
Zhou, "Application of DNA molecular marker technique in plant study," *Chemical Industry Press*. 1st edition, p. 217. 2005.

* cited by examiner

A

B

| | number of observed plants | | Chi square | P value |
|---|---|---|---|---|
| Gy1,3 levels | ≤3.0% | ≥3.1% | | |
| JB0305602 | 92 | 307 | 0.854 | 0.355 |
| JB0305605 | 97 | 301 | 0.120 | 0.942 |
| Total | 189 | 608 | 0.670 | 0.715 |

A

B

| | number of observed plants | | | |
|---|---|---|---|---|
| Gy2 levels | ≤1.0 | ≥1.1 | Chi square | P value |
| JB0305602 | 95 | 305 | 0.333 | 0.564 |
| JB0305605 | 91 | 309 | 1.080 | 0.583 |
| Total | 186 | 614 | 1.307 | 0.520 |

A

B

Phenotypic correlation coefficients (r)

| | Gy1,3 | Gy2 | Gy4 | Gy5 |
|---|---|---|---|---|
| Gy1,3 | 1 | | | |
| Gy2 | 0.88 | 1 | | |
| Gy4 | -0.23 | -0.16 | 1 | |
| Gy5 | -0.59 | -0.62 | 0.04 | 1 |

A

B

| | number of observed plants | | | |
|---|---|---|---|---|
| Gy4 levels | 0 | >0 | Chi square | P value |
| JB0305602 | 106 | 294 | 0.480 | 0.488 |
| JB0305605 | 95 | 305 | 0.333 | 0.846 |
| Total | 201 | 599 | 0.007 | 0.997 |

A

B

| | Gy total |
|---|---|
| Cgy1 | -0.83 |
| Cgy2,3 | -0.79 |
| Cgy4 | -0.36 |
| Cgy total | -0.78 |

A

B

SEQUENCE LISTING

```
<160> NUMBER OF SEQ ID NOS: 177

<210> SEQ ID NO 1
<211> LENGTH: 26
```

-continued

<212> TYPE: DNA
<213> ORGANISM: Artificial Sequence
<220> FEATURE:
<223> OTHER INFORMATION: Synthetic Primer

<400> SEQUENCE: 1
gcctaagtac gtactcaaaa tgccaa 26

<210> SEQ ID NO 2
<211> LENGTH: 27
<212> TYPE: DNA
<213> ORGANISM: Artificial Sequence
<220> FEATURE:
<223> OTHER INFORMATION: Synthetic Primer

<400> SEQUENCE: 2
ctacacctca tgaagttcat ggtgtga 27

<210> SEQ ID NO 3
<211> LENGTH: 27
<212> TYPE: DNA
<213> ORGANISM: Artificial Sequence
<220> FEATURE:
<223> OTHER INFORMATION: Synthetic Primer

<400> SEQUENCE: 3
ccatgcatgg tcccctcgtc atcacga 27

<210> SEQ ID NO 4
<211> LENGTH: 29
<212> TYPE: DNA
<213> ORGANISM: Artificial Sequence
<220> FEATURE:
<223> OTHER INFORMATION: Synthetic Primer

<400> SEQUENCE: 4
ccctcattta tcaaaccctt aaacatatt 29

<210> SEQ ID NO 5
<211> LENGTH: 30
<212> TYPE: DNA
<213> ORGANISM: Artificial Sequence
<220> FEATURE:
<223> OTHER INFORMATION: Synthetic Primer

<400> SEQUENCE: 5
gaacttcatg aggtgtagca cccaaggctt 30

<210> SEQ ID NO 6
<211> LENGTH: 30
<212> TYPE: DNA
<213> ORGANISM: Artificial Sequence
<220> FEATURE:
<223> OTHER INFORMATION: Synthetic Primer

<400> SEQUENCE: 6
gattatgtta cgtcatatgg aagaaatcaa 30

<210> SEQ ID NO 7
<211> LENGTH: 31
<212> TYPE: DNA
<213> ORGANISM: Artificial Sequence
<220> FEATURE:
<223> OTHER INFORMATION: Synthetic Primer

<400> SEQUENCE: 7
ccatatgacg taacataatc atatcattga t 31

<210> SEQ ID NO 8
<211> LENGTH: 30
<212> TYPE: DNA
<213> ORGANISM: Artificial Sequence
<220> FEATURE:
<223> OTHER INFORMATION: Synthetic Primer

<400> SEQUENCE: 8
gaattataat atctaatatt gctatgtggc 30

<210> SEQ ID NO 9
<211> LENGTH: 29
<212> TYPE: DNA
<213> ORGANISM: Artificial Sequence
<220> FEATURE:
<223> OTHER INFORMATION: Synthetic Primer

<400> SEQUENCE: 9
ctcaacaaag aggacaaagc agcagacca 29

<210> SEQ ID NO 10
<211> LENGTH: 28
<212> TYPE: DNA
<213> ORGANISM: Artificial Sequence
<220> FEATURE:
<223> OTHER INFORMATION: Synthetic Primer

<400> SEQUENCE: 10
gatgacctcc ttgctcttgc tgatattt 28

<210> SEQ ID NO 11
<211> LENGTH: 29
<212> TYPE: DNA
<213> ORGANISM: Artificial Sequence
<220> FEATURE:
<223> OTHER INFORMATION: Synthetic Primer

<400> SEQUENCE: 11
caccctggaa ttcttggaac atgcattca 29

<210> SEQ ID NO 12
<211> LENGTH: 27
<212> TYPE: DNA
<213> ORGANISM: Artificial Sequence
<220> FEATURE:
<223> OTHER INFORMATION: Synthetic Primer

<400> SEQUENCE: 12
ggagagatcc aaactcagca ctgagtc 27

<210> SEQ ID NO 13
<211> LENGTH: 22
<212> TYPE: DNA
<213> ORGANISM: Artificial Sequence
<220> FEATURE:
<223> OTHER INFORMATION: Synthetic Primer

<400> SEQUENCE: 13
gcgtggacaa gcagatagcg aa 22

<210> SEQ ID NO 14
<211> LENGTH: 22
<212> TYPE: DNA
<213> ORGANISM: Artificial Sequence
<220> FEATURE:
<223> OTHER INFORMATION: Synthetic Primer

<400> SEQUENCE: 14
cttgcggaga gatccaaact ca 22

<210> SEQ ID NO 15
<211> LENGTH: 26
<212> TYPE: DNA
<213> ORGANISM: Artificial Sequence
<220> FEATURE:
<223> OTHER INFORMATION: Synthetic Primer

<400> SEQUENCE: 15
gaggatgaga agccacagtg caaggg 26

<210> SEQ ID NO 16
<211> LENGTH: 31
<212> TYPE: DNA
<213> ORGANISM: Artificial Sequence
<220> FEATURE:
<223> OTHER INFORMATION: Synthetic Primer

<400> SEQUENCE: 16
gtatgttgat ctttgatgaa tgatgtacgt a 31

<210> SEQ ID NO 17
<211> LENGTH: 29
<212> TYPE: DNA
<213> ORGANISM: Artificial Sequence
<220> FEATURE:
<223> OTHER INFORMATION: Synthetic Primer

<400> SEQUENCE: 17
ggatgaattt gttgtgactc ttgcatgca 29

<210> SEQ ID NO 18
<211> LENGTH: 29
<212> TYPE: DNA
<213> ORGANISM: Artificial Sequence
<220> FEATURE:
<223> OTHER INFORMATION: Synthetic Primer

<400> SEQUENCE: 18
ctgagactcc tgaggtggaa ccaggaact 29

<210> SEQ ID NO 19
<211> LENGTH: 28
<212> TYPE: DNA
<213> ORGANISM: Artificial Sequence
<220> FEATURE:
<223> OTHER INFORMATION: Synthetic Primer

<400> SEQUENCE: 19
gcagataaag aacaacaacc ctttcaag 28

<210> SEQ ID NO 20
<211> LENGTH: 29
<212> TYPE: DNA
<213> ORGANISM: Artificial Sequence
<220> FEATURE:
<223> OTHER INFORMATION: Synthetic Primer

<400> SEQUENCE: 20
caacacttcc taaagatatc atcgatcaa 29

-continued

<210> SEQ ID NO 21
<211> LENGTH: 27
<212> TYPE: DNA
<213> ORGANISM: Artificial Sequence
<220> FEATURE:
<223> OTHER INFORMATION: Synthetic Primer

<400> SEQUENCE: 21
gcaattgcat gcaatacaaa cacactt 27

<210> SEQ ID NO 22
<211> LENGTH: 29
<212> TYPE: DNA
<213> ORGANISM: Artificial Sequence
<220> FEATURE:
<223> OTHER INFORMATION: Synthetic Primer

<400> SEQUENCE: 22
gccacagttt caatcaattt tactaacaa 29

<210> SEQ ID NO 23
<211> LENGTH: 29
<212> TYPE: DNA
<213> ORGANISM: Artificial Sequence
<220> FEATURE:
<223> OTHER INFORMATION: Synthetic Primer

<400> SEQUENCE: 23
ccatgaactt aatgaggtgt aacacacaa 29

<210> SEQ ID NO 24
<211> LENGTH: 26
<212> TYPE: DNA
<213> ORGANISM: Artificial Sequence
<220> FEATURE:
<223> OTHER INFORMATION: Synthetic Primer

<400> SEQUENCE: 24
aagataggtt ggacggttaa gaagaa 26

<210> SEQ ID NO 25
<211> LENGTH: 27
<212> TYPE: DNA
<213> ORGANISM: Artificial Sequence
<220> FEATURE:
<223> OTHER INFORMATION: Synthetic Primer

<400> SEQUENCE: 25
accgtccaac ctatcttata tattcaa 27

<210> SEQ ID NO 26
<211> LENGTH: 26
<212> TYPE: DNA
<213> ORGANISM: Artificial Sequence
<220> FEATURE:
<223> OTHER INFORMATION: Synthetic Primer

<400> SEQUENCE: 26
caccctctct gaagcgatgt accttt 26

<210> SEQ ID NO 27
<211> LENGTH: 28
<212> TYPE: DNA
<213> ORGANISM: Artificial Sequence
<220> FEATURE:
<223> OTHER INFORMATION: Synthetic Primer

<400> SEQUENCE: 27
cctagcactt atcaagagcc gcaagaat 28

<210> SEQ ID NO 28
<211> LENGTH: 27
<212> TYPE: DNA
<213> ORGANISM: Artificial Sequence
<220> FEATURE:
<223> OTHER INFORMATION: Synthetic Primer

<400> SEQUENCE: 28
ctgcatgttc acgccgaacg cttcttt 27

<210> SEQ ID NO 29
<211> LENGTH: 28
<212> TYPE: DNA
<213> ORGANISM: Artificial Sequence
<220> FEATURE:
<223> OTHER INFORMATION: Synthetic Primer

<400> SEQUENCE: 29
atatcagcag cagcagcaag gaggttcc 28

<210> SEQ ID NO 30
<211> LENGTH: 27
<212> TYPE: DNA
<213> ORGANISM: Artificial Sequence
<220> FEATURE:
<223> OTHER INFORMATION: Synthetic Primer

<400> SEQUENCE: 30
gcaagtgcta agataacttt gtcgtca 27

<210> SEQ ID NO 31
<211> LENGTH: 27
<212> TYPE: DNA
<213> ORGANISM: Artificial Sequence
<220> FEATURE:
<223> OTHER INFORMATION: Synthetic Primer

<400> SEQUENCE: 31
cttgaaagaa gcgttcggcg tgaacat 27

<210> SEQ ID NO 32
<211> LENGTH: 27
<212> TYPE: DNA
<213> ORGANISM: Artificial Sequence
<220> FEATURE:
<223> OTHER INFORMATION: Synthetic Primer

<400> SEQUENCE: 32
gcaagtgcta agataacttt gtcgtca 27

<210> SEQ ID NO 33
<211> LENGTH: 28
<212> TYPE: DNA
<213> ORGANISM: Artificial Sequence
<220> FEATURE:
<223> OTHER INFORMATION: Synthetic Primer

<400> SEQUENCE: 33
ggatgaataa catgttgtga ttaacgta 28

<210> SEQ ID NO 34

<211> LENGTH: 29
<212> TYPE: DNA
<213> ORGANISM: Artificial Sequence
<220> FEATURE:
<223> OTHER INFORMATION: Synthetic Primer

<400> SEQUENCE: 34
caaggaagct gaaagggttg ttgttcttc 29

<210> SEQ ID NO 35
<211> LENGTH: 27
<212> TYPE: DNA
<213> ORGANISM: Artificial Sequence
<220> FEATURE:
<223> OTHER INFORMATION: Synthetic Primer

<400> SEQUENCE: 35
caccattaac ttaatagtgt aagacag 27

<210> SEQ ID NO 36
<211> LENGTH: 30
<212> TYPE: DNA
<213> ORGANISM: Artificial Sequence
<220> FEATURE:
<223> OTHER INFORMATION: Synthetic Primer

<400> SEQUENCE: 36
ccttgttgaa taaaggttgt aagttggatt 30

<210> SEQ ID NO 37
<211> LENGTH: 31
<212> TYPE: DNA
<213> ORGANISM: Artificial Sequence
<220> FEATURE:
<223> OTHER INFORMATION: Synthetic Primer

<400> SEQUENCE: 37
gattccgaag ccaccttaca ccattaactt a 31

<210> SEQ ID NO 38
<211> LENGTH: 30
<212> TYPE: DNA
<213> ORGANISM: Artificial Sequence
<220> FEATURE:
<223> OTHER INFORMATION: Synthetic Primer

<400> SEQUENCE: 38
ggataaaatg aaccttgttg aataaaggtt 30

<210> SEQ ID NO 39
<211> LENGTH: 29
<212> TYPE: DNA
<213> ORGANISM: Artificial Sequence
<220> FEATURE:
<223> OTHER INFORMATION: Synthetic Primer

<400> SEQUENCE: 39
gtcttaagct cagcacccca cttctgagt 29

<210> SEQ ID NO 40
<211> LENGTH: 30
<212> TYPE: DNA
<213> ORGANISM: Artificial Sequence
<220> FEATURE:
<223> OTHER INFORMATION: Synthetic Primer

<400> SEQUENCE: 40
ggataaaatg aaccttgttg aataaaggtt 30

<210> SEQ ID NO 41
<211> LENGTH: 29
<212> TYPE: DNA
<213> ORGANISM: Artificial Sequence
<220> FEATURE:
<223> OTHER INFORMATION: Synthetic Primer

<400> SEQUENCE: 41
cctcaagagt aacgttaagg acatcgata 29

<210> SEQ ID NO 42
<211> LENGTH: 29
<212> TYPE: DNA
<213> ORGANISM: Artificial Sequence
<220> FEATURE:
<223> OTHER INFORMATION: Synthetic Primer

<400> SEQUENCE: 42
cagttattta aagtgatttc accacgagg 29

<210> SEQ ID NO 43
<211> LENGTH: 28
<212> TYPE: DNA
<213> ORGANISM: Artificial Sequence
<220> FEATURE:
<223> OTHER INFORMATION: Synthetic Primer

<400> SEQUENCE: 43
aagaaattgg acaacgttgt aacatgca 28

<210> SEQ ID NO 44
<211> LENGTH: 29
<212> TYPE: DNA
<213> ORGANISM: Artificial Sequence
<220> FEATURE:
<223> OTHER INFORMATION: Synthetic Primer

<400> SEQUENCE: 44
caatgtttgt ctttctcgtc acaatctgg 29

<210> SEQ ID NO 45
<211> LENGTH: 28
<212> TYPE: DNA
<213> ORGANISM: Artificial Sequence
<220> FEATURE:
<223> OTHER INFORMATION: Synthetic Primer

<400> SEQUENCE: 45
aagaaattgg acaacgttgt aacatgca 28

<210> SEQ ID NO 46
<211> LENGTH: 31
<212> TYPE: DNA
<213> ORGANISM: Artificial Sequence
<220> FEATURE:
<223> OTHER INFORMATION: Synthetic Primer

<400> SEQUENCE: 46
gcttttataa catgaattaa tgatgtaagt a 31

<210> SEQ ID NO 47
<211> LENGTH: 28
<212> TYPE: DNA

-continued

```
<213> ORGANISM: Artificial Sequence
<220> FEATURE:
<223> OTHER INFORMATION: Synthetic Primer

<400> SEQUENCE: 47

gattaacgta cacttgatgt atggtgca                                    28


<210> SEQ ID NO 48
<211> LENGTH: 30
<212> TYPE: DNA
<213> ORGANISM: Artificial Sequence
<220> FEATURE:
<223> OTHER INFORMATION: Synthetic Primer

<400> SEQUENCE: 48

gcataggtac ttgagtgact cattacacaa                                  30


<210> SEQ ID NO 49
<211> LENGTH: 27
<212> TYPE: DNA
<213> ORGANISM: Artificial Sequence
<220> FEATURE:
<223> OTHER INFORMATION: Synthetic Primer

<400> SEQUENCE: 49

gcacagtaaa acagttcaaa ttgagaa                                     27


<210> SEQ ID NO 50
<211> LENGTH: 27
<212> TYPE: DNA
<213> ORGANISM: Artificial Sequence
<220> FEATURE:
<223> OTHER INFORMATION: Synthetic Primer

<400> SEQUENCE: 50

cattcttcac cttgcatggc tattgtt                                     27


<210> SEQ ID NO 51
<211> LENGTH: 30
<212> TYPE: DNA
<213> ORGANISM: Artificial Sequence
<220> FEATURE:
<223> OTHER INFORMATION: Synthetic Primer

<400> SEQUENCE: 51

gcaaggtgaa gaatgtcaca aactcagcaa                                  30


<210> SEQ ID NO 52
<211> LENGTH: 30
<212> TYPE: DNA
<213> ORGANISM: Artificial Sequence
<220> FEATURE:
<223> OTHER INFORMATION: Synthetic Primer

<400> SEQUENCE: 52

ggtgacaaat ggattaatat acactgagaa                                  30


<210> SEQ ID NO 53
<211> LENGTH: 26
<212> TYPE: DNA
<213> ORGANISM: Artificial Sequence
<220> FEATURE:
<223> OTHER INFORMATION: Synthetic Primer

<400> SEQUENCE: 53

ggatgatcat catcgcccaa ggtaat                                      26
```

<210> SEQ ID NO 54
<211> LENGTH: 27
<212> TYPE: DNA
<213> ORGANISM: Artificial Sequence
<220> FEATURE:
<223> OTHER INFORMATION: Synthetic Primer

<400> SEQUENCE: 54
ctggtgactg tcctgtagct gctgctt 27

<210> SEQ ID NO 55
<211> LENGTH: 27
<212> TYPE: DNA
<213> ORGANISM: Artificial Sequence
<220> FEATURE:
<223> OTHER INFORMATION: Synthetic Primer

<400> SEQUENCE: 55
tcaaggtcgc agaagcagca gctacag 27

<210> SEQ ID NO 56
<211> LENGTH: 28
<212> TYPE: DNA
<213> ORGANISM: Artificial Sequence
<220> FEATURE:
<223> OTHER INFORMATION: Synthetic Primer

<400> SEQUENCE: 56
tgagagggaa tttgttcatc ttcatcat 28

<210> SEQ ID NO 57
<211> LENGTH: 30
<212> TYPE: DNA
<213> ORGANISM: Artificial Sequence
<220> FEATURE:
<223> OTHER INFORMATION: Synthetic Primer

<400> SEQUENCE: 57
gatgatgaag atgaacaaat tccctctcac 30

<210> SEQ ID NO 58
<211> LENGTH: 30
<212> TYPE: DNA
<213> ORGANISM: Artificial Sequence
<220> FEATURE:
<223> OTHER INFORMATION: Synthetic Primer

<400> SEQUENCE: 58
gtagaggaca acatattggg cactgagttg 30

<210> SEQ ID NO 59
<211> LENGTH: 27
<212> TYPE: DNA
<213> ORGANISM: Artificial Sequence
<220> FEATURE:
<223> OTHER INFORMATION: Synthetic Primer

<400> SEQUENCE: 59
caccctccca gccctccgcc aattcca 27

<210> SEQ ID NO 60
<211> LENGTH: 30
<212> TYPE: DNA
<213> ORGANISM: Artificial Sequence
<220> FEATURE:

<223> OTHER INFORMATION: Synthetic Primer

<400> SEQUENCE: 60
gtcacataga tcacactgtt tgcattcaga 30

<210> SEQ ID NO 61
<211> LENGTH: 28
<212> TYPE: DNA
<213> ORGANISM: Artificial Sequence
<220> FEATURE:
<223> OTHER INFORMATION: Synthetic Primer

<400> SEQUENCE: 61
ttactctcca cattggaatc tgaatgca 28

<210> SEQ ID NO 62
<211> LENGTH: 29
<212> TYPE: DNA
<213> ORGANISM: Artificial Sequence
<220> FEATURE:
<223> OTHER INFORMATION: Synthetic Primer

<400> SEQUENCE: 62
gccactcaga tataaacata ggctcgctg 29

<210> SEQ ID NO 63
<211> LENGTH: 29
<212> TYPE: DNA
<213> ORGANISM: Artificial Sequence
<220> FEATURE:
<223> OTHER INFORMATION: Synthetic Primer

<400> SEQUENCE: 63
cataaatgac aagcatgatg gtgtgagga 29

<210> SEQ ID NO 64
<211> LENGTH: 31
<212> TYPE: DNA
<213> ORGANISM: Artificial Sequence
<220> FEATURE:
<223> OTHER INFORMATION: Synthetic Primer

<400> SEQUENCE: 64
ccagtaaaca tataatcagt attactcatt t 31

<210> SEQ ID NO 65
<211> LENGTH: 28
<212> TYPE: DNA
<213> ORGANISM: Artificial Sequence
<220> FEATURE:
<223> OTHER INFORMATION: Synthetic Primer

<400> SEQUENCE: 65
agccatgcaa ggtgaagaat gtcacaaa 28

<210> SEQ ID NO 66
<211> LENGTH: 27
<212> TYPE: DNA
<213> ORGANISM: Artificial Sequence
<220> FEATURE:
<223> OTHER INFORMATION: Synthetic Primer

<400> SEQUENCE: 66
aagagtatca ccagcatttc tcagtgt 27

-continued

<210> SEQ ID NO 67
<211> LENGTH: 26
<212> TYPE: DNA
<213> ORGANISM: Artificial Sequence
<220> FEATURE:
<223> OTHER INFORMATION: Synthetic Primer

<400> SEQUENCE: 67
ctttgttgac atatcaatca ccttaa 26

<210> SEQ ID NO 68
<211> LENGTH: 28
<212> TYPE: DNA
<213> ORGANISM: Artificial Sequence
<220> FEATURE:
<223> OTHER INFORMATION: Synthetic Primer

<400> SEQUENCE: 68
gtgaaagaat taacaagtaa ggagaaca 28

<210> SEQ ID NO 69
<211> LENGTH: 29
<212> TYPE: DNA
<213> ORGANISM: Artificial Sequence
<220> FEATURE:
<223> OTHER INFORMATION: Synthetic Primer

<400> SEQUENCE: 69
gttctcctta cttgttaatt ctttcactt 29

<210> SEQ ID NO 70
<211> LENGTH: 27
<212> TYPE: DNA
<213> ORGANISM: Artificial Sequence
<220> FEATURE:
<223> OTHER INFORMATION: Synthetic Primer

<400> SEQUENCE: 70
gtcctggtcc tggtcttgtt cacgctt 27

<210> SEQ ID NO 71
<211> LENGTH: 28
<212> TYPE: DNA
<213> ORGANISM: Artificial Sequence
<220> FEATURE:
<223> OTHER INFORMATION: Synthetic Primer

<400> SEQUENCE: 71
gaagatcaac ctcgcaagag ccgcgaat 28

<210> SEQ ID NO 72
<211> LENGTH: 29
<212> TYPE: DNA
<213> ORGANISM: Artificial Sequence
<220> FEATURE:
<223> OTHER INFORMATION: Synthetic Primer

<400> SEQUENCE: 72
caactacccc tagagaatca ctaaagaat 29

<210> SEQ ID NO 73
<211> LENGTH: 28
<212> TYPE: DNA
<213> ORGANISM: Artificial Sequence
<220> FEATURE:
<223> OTHER INFORMATION: Synthetic Primer

<400> SEQUENCE: 73
gtcagtaagt atgttgtagg gttggatt 28

<210> SEQ ID NO 74
<211> LENGTH: 28
<212> TYPE: DNA
<213> ORGANISM: Artificial Sequence
<220> FEATURE:
<223> OTHER INFORMATION: Synthetic Primer

<400> SEQUENCE: 74
ccatcatgct tgtcatttat gcgacttt 28

<210> SEQ ID NO 75
<211> LENGTH: 28
<212> TYPE: DNA
<213> ORGANISM: Artificial Sequence
<220> FEATURE:
<223> OTHER INFORMATION: Synthetic Primer

<400> SEQUENCE: 75
caaggctcac cccgtgttaa agtcgcat 28

<210> SEQ ID NO 76
<211> LENGTH: 29
<212> TYPE: DNA
<213> ORGANISM: Artificial Sequence
<220> FEATURE:
<223> OTHER INFORMATION: Synthetic Primer

<400> SEQUENCE: 76
gaataaagac aaaacgtgaa gactgacat 29

<210> SEQ ID NO 77
<211> LENGTH: 24
<212> TYPE: DNA
<213> ORGANISM: Artificial Sequence
<220> FEATURE:
<223> OTHER INFORMATION: Synthetic Primer

<400> SEQUENCE: 77
ctccttcaaa cttattaaca cttt 24

<210> SEQ ID NO 78
<211> LENGTH: 22
<212> TYPE: DNA
<213> ORGANISM: Artificial Sequence
<220> FEATURE:
<223> OTHER INFORMATION: Synthetic Primer

<400> SEQUENCE: 78
ccttgaacga caatgatcat tt 22

<210> SEQ ID NO 79
<211> LENGTH: 25
<212> TYPE: DNA
<213> ORGANISM: Artificial Sequence
<220> FEATURE:
<223> OTHER INFORMATION: Synthetic Primer

<400> SEQUENCE: 79
ctcaaggtcg cagcagcaac tacaa 25

<210> SEQ ID NO 80
<211> LENGTH: 24

<212> TYPE: DNA
<213> ORGANISM: Artificial Sequence
<220> FEATURE:
<223> OTHER INFORMATION: Synthetic Primer

<400> SEQUENCE: 80
gagggagttt gttcatattc ttcg 24

<210> SEQ ID NO 81
<211> LENGTH: 25
<212> TYPE: DNA
<213> ORGANISM: Artificial Sequence
<220> FEATURE:
<223> OTHER INFORMATION: Synthetic Primer

<400> SEQUENCE: 81
gaagaatatg aacaaactcc ctctt 25

<210> SEQ ID NO 82
<211> LENGTH: 25
<212> TYPE: DNA
<213> ORGANISM: Artificial Sequence
<220> FEATURE:
<223> OTHER INFORMATION: Synthetic Primer

<400> SEQUENCE: 82
ggacaacata ttgggcactg agtcc 25

<210> SEQ ID NO 83
<211> LENGTH: 23
<212> TYPE: DNA
<213> ORGANISM: Artificial Sequence
<220> FEATURE:
<223> OTHER INFORMATION: Synthetic Primer

<400> SEQUENCE: 83
ctcccagccc tccgccaatt cgg 23

<210> SEQ ID NO 84
<211> LENGTH: 28
<212> TYPE: DNA
<213> ORGANISM: Artificial Sequence
<220> FEATURE:
<223> OTHER INFORMATION: Synthetic Primer

<400> SEQUENCE: 84
cacatagatc acactgttcg cgttcaag 28

<210> SEQ ID NO 85
<211> LENGTH: 27
<212> TYPE: DNA
<213> ORGANISM: Artificial Sequence
<220> FEATURE:
<223> OTHER INFORMATION: Synthetic Primer

<400> SEQUENCE: 85
tactctccac attggaactt gaacgcg 27

<210> SEQ ID NO 86
<211> LENGTH: 27
<212> TYPE: DNA
<213> ORGANISM: Artificial Sequence
<220> FEATURE:
<223> OTHER INFORMATION: Synthetic Primer

<400> SEQUENCE: 86
cactcagata ttaacatagg ctgggtc 27

<210> SEQ ID NO 87
<211> LENGTH: 25
<212> TYPE: DNA
<213> ORGANISM: Artificial Sequence
<220> FEATURE:
<223> OTHER INFORMATION: Synthetic Primer

<400> SEQUENCE: 87
ggccctttgg tcaacccata aataa 25

<210> SEQ ID NO 88
<211> LENGTH: 27
<212> TYPE: DNA
<213> ORGANISM: Artificial Sequence
<220> FEATURE:
<223> OTHER INFORMATION: Synthetic Primer

<400> SEQUENCE: 88
aagactgaca ttttattaag gcgattc 27

<210> SEQ ID NO 89
<211> LENGTH: 29
<212> TYPE: DNA
<213> ORGANISM: Artificial Sequence
<220> FEATURE:
<223> OTHER INFORMATION: Synthetic Primer

<400> SEQUENCE: 89
catggaactc tcaacaccct gagctgcaa 29

<210> SEQ ID NO 90
<211> LENGTH: 28
<212> TYPE: DNA
<213> ORGANISM: Artificial Sequence
<220> FEATURE:
<223> OTHER INFORMATION: Synthetic Primer

<400> SEQUENCE: 90
cctctagata taagatagtg ttcttcaa 28

<210> SEQ ID NO 91
<211> LENGTH: 26
<212> TYPE: DNA
<213> ORGANISM: Artificial Sequence
<220> FEATURE:
<223> OTHER INFORMATION: Synthetic Primer

<400> SEQUENCE: 91
gtcactgttt ccaaacgcac cctcaa 26

<210> SEQ ID NO 92
<211> LENGTH: 26
<212> TYPE: DNA
<213> ORGANISM: Artificial Sequence
<220> FEATURE:
<223> OTHER INFORMATION: Synthetic Primer

<400> SEQUENCE: 92
gggttcccag caaggtaaaa tacctt 26

<210> SEQ ID NO 93
<211> LENGTH: 26
<212> TYPE: DNA
<213> ORGANISM: Artificial Sequence
<220> FEATURE:
<223> OTHER INFORMATION: Synthetic Primer

<400> SEQUENCE: 93
gtgttcctta ctggacctat aacact 26

<210> SEQ ID NO 94
<211> LENGTH: 25
<212> TYPE: DNA
<213> ORGANISM: Artificial Sequence
<220> FEATURE:
<223> OTHER INFORMATION: Synthetic Primer

<400> SEQUENCE: 94
gggtgatcag gacgaggttg atctt 25

<210> SEQ ID NO 95
<211> LENGTH: 26
<212> TYPE: DNA
<213> ORGANISM: Artificial Sequence
<220> FEATURE:
<223> OTHER INFORMATION: Synthetic Primer

<400> SEQUENCE: 95
gtcactgcat agtatcatac acactt 26

<210> SEQ ID NO 96
<211> LENGTH: 25
<212> TYPE: DNA
<213> ORGANISM: Artificial Sequence
<220> FEATURE:
<223> OTHER INFORMATION: Synthetic Primer

<400> SEQUENCE: 96
gtctgacatc ctcttccacg tggtt 25

<210> SEQ ID NO 97
<211> LENGTH: 27
<212> TYPE: DNA
<213> ORGANISM: Artificial Sequence
<220> FEATURE:
<223> OTHER INFORMATION: Synthetic Primer

<400> SEQUENCE: 97
cgagaacaat agaaatagac catcagg 27

<210> SEQ ID NO 98
<211> LENGTH: 25
<212> TYPE: DNA
<213> ORGANISM: Artificial Sequence
<220> FEATURE:
<223> OTHER INFORMATION: Synthetic Primer

<400> SEQUENCE: 98
cctcttcaca caatgatcca aactc 25

<210> SEQ ID NO 99
<211> LENGTH: 23
<212> TYPE: DNA
<213> ORGANISM: Artificial Sequence
<220> FEATURE:
<223> OTHER INFORMATION: Synthetic Primer

<400> SEQUENCE: 99
gtccagggtc catgttatcg tct 23

<210> SEQ ID NO 100
<211> LENGTH: 26
<212> TYPE: DNA
<213> ORGANISM: Artificial Sequence
<220> FEATURE:
<223> OTHER INFORMATION: Synthetic Primer

<400> SEQUENCE: 100
cattgtcctt tccttactga ttctcc 26

<210> SEQ ID NO 101
<211> LENGTH: 27
<212> TYPE: DNA
<213> ORGANISM: Artificial Sequence
<220> FEATURE:
<223> OTHER INFORMATION: Synthetic Primer

<400> SEQUENCE: 101
tgactgcatg tatcatgtat gtgaaag 27

<210> SEQ ID NO 102
<211> LENGTH: 24
<212> TYPE: DNA
<213> ORGANISM: Artificial Sequence
<220> FEATURE:
<223> OTHER INFORMATION: Synthetic Primer

<400> SEQUENCE: 102
gattcgatga ggttgtcagg tttc 24

<210> SEQ ID NO 103
<211> LENGTH: 25
<212> TYPE: DNA
<213> ORGANISM: Artificial Sequence
<220> FEATURE:
<223> OTHER INFORMATION: Synthetic Primer

<400> SEQUENCE: 103
cggagaatca gtaaggaaag gacaa 25

<210> SEQ ID NO 104
<211> LENGTH: 25
<212> TYPE: DNA
<213> ORGANISM: Artificial Sequence
<220> FEATURE:
<223> OTHER INFORMATION: Synthetic Primer

<400> SEQUENCE: 104
tgaggttgtt ggataccttg gagta 25

<210> SEQ ID NO 105
<211> LENGTH: 25
<212> TYPE: DNA
<213> ORGANISM: Artificial Sequence
<220> FEATURE:
<223> OTHER INFORMATION: Synthetic Primer

<400> SEQUENCE: 105
accattctgc gctccattat tattt 25

<210> SEQ ID NO 106
<211> LENGTH: 25
<212> TYPE: DNA
<213> ORGANISM: Artificial Sequence
<220> FEATURE:
<223> OTHER INFORMATION: Synthetic Primer

<400> SEQUENCE: 106
agtttcgtca caaccaggaa ttaca 25

<210> SEQ ID NO 107
<211> LENGTH: 25
<212> TYPE: DNA
<213> ORGANISM: Artificial Sequence
<220> FEATURE:
<223> OTHER INFORMATION: Synthetic Primer

<400> SEQUENCE: 107
gtttaaccat tctgcgctcc attat 25

<210> SEQ ID NO 108
<211> LENGTH: 25
<212> TYPE: DNA
<213> ORGANISM: Artificial Sequence
<220> FEATURE:
<223> OTHER INFORMATION: Synthetic Primer

<400> SEQUENCE: 108
gaatatgtca ccctgcttca ggtaa 25

<210> SEQ ID NO 109
<211> LENGTH: 25
<212> TYPE: DNA
<213> ORGANISM: Artificial Sequence
<220> FEATURE:
<223> OTHER INFORMATION: Synthetic Primer

<400> SEQUENCE: 109
tgtaattcct ggttgtgacg aaact 25

<210> SEQ ID NO 110
<211> LENGTH: 25
<212> TYPE: DNA
<213> ORGANISM: Artificial Sequence
<220> FEATURE:
<223> OTHER INFORMATION: Synthetic Primer

<400> SEQUENCE: 110
gtggcctgat aatgctaaga ccttt 25

<210> SEQ ID NO 111
<211> LENGTH: 24
<212> TYPE: DNA
<213> ORGANISM: Artificial Sequence
<220> FEATURE:
<223> OTHER INFORMATION: Synthetic Primer

<400> SEQUENCE: 111
cgttacctga agcagggtga cata 24

<210> SEQ ID NO 112
<211> LENGTH: 26
<212> TYPE: DNA
<213> ORGANISM: Artificial Sequence
<220> FEATURE:
<223> OTHER INFORMATION: Synthetic Primer

<400> SEQUENCE: 112
cacctcttct tctccttctc cttctt 26

<210> SEQ ID NO 113

<211> LENGTH: 25
<212> TYPE: DNA
<213> ORGANISM: Artificial Sequence
<220> FEATURE:
<223> OTHER INFORMATION: Synthetic Primer

<400> SEQUENCE: 113
cttggaacac gaagttagag aagca 25

<210> SEQ ID NO 114
<211> LENGTH: 25
<212> TYPE: DNA
<213> ORGANISM: Artificial Sequence
<220> FEATURE:
<223> OTHER INFORMATION: Synthetic Primer

<400> SEQUENCE: 114
cggttattgt ggttgtaagt gtggt 25

<210> SEQ ID NO 115
<211> LENGTH: 25
<212> TYPE: DNA
<213> ORGANISM: Artificial Sequence
<220> FEATURE:
<223> OTHER INFORMATION: Synthetic Primer

<400> SEQUENCE: 115
cccaatgggt taaactctac aaggt 25

<210> SEQ ID NO 116
<211> LENGTH: 25
<212> TYPE: DNA
<213> ORGANISM: Artificial Sequence
<220> FEATURE:
<223> OTHER INFORMATION: Synthetic Primer

<400> SEQUENCE: 116
attattcttg agctcgctca cttcc 25

<210> SEQ ID NO 117
<211> LENGTH: 22
<212> TYPE: DNA
<213> ORGANISM: Artificial Sequence
<220> FEATURE:
<223> OTHER INFORMATION: Synthetic Primer

<400> SEQUENCE: 117
gtggtgaact cccagggaaa gt 22

<210> SEQ ID NO 118
<211> LENGTH: 27
<212> TYPE: DNA
<213> ORGANISM: Artificial Sequence
<220> FEATURE:
<223> OTHER INFORMATION: Synthetic Primer

<400> SEQUENCE: 118
gaggaaagta caaatagcaa ctgacaa 27

<210> SEQ ID NO 119
<211> LENGTH: 28
<212> TYPE: DNA
<213> ORGANISM: Artificial Sequence
<220> FEATURE:
<223> OTHER INFORMATION: Synthetic Primer

<400> SEQUENCE: 119
cgaagccacc tcacaccatg aacttcat 28

<210> SEQ ID NO 120
<211> LENGTH: 29
<212> TYPE: DNA
<213> ORGANISM: Artificial Sequence
<220> FEATURE:
<223> OTHER INFORMATION: Synthetic Primer

<400> SEQUENCE: 120
cagaagtagg gtgctgagct tgagacatt 29

<210> SEQ ID NO 121
<211> LENGTH: 30
<212> TYPE: DNA
<213> ORGANISM: Artificial Sequence
<220> FEATURE:
<223> OTHER INFORMATION: Synthetic Primer

<400> SEQUENCE: 121
gtccctcatt caccttcctc tcttccctat 30

<210> SEQ ID NO 122
<211> LENGTH: 29
<212> TYPE: DNA
<213> ORGANISM: Artificial Sequence
<220> FEATURE:
<223> OTHER INFORMATION: Synthetic Primer

<400> SEQUENCE: 122
gcttggccat ggtgatgact gatgagtgt 29

<210> SEQ ID NO 123
<211> LENGTH: 28
<212> TYPE: DNA
<213> ORGANISM: Artificial Sequence
<220> FEATURE:
<223> OTHER INFORMATION: Synthetic Primer

<400> SEQUENCE: 123
ctcaatgccc tcaaaccgga taaccgta 28

<210> SEQ ID NO 124
<211> LENGTH: 28
<212> TYPE: DNA
<213> ORGANISM: Artificial Sequence
<220> FEATURE:
<223> OTHER INFORMATION: Synthetic Primer

<400> SEQUENCE: 124
caacaccggc acactggaat ggcttgtt 28

<210> SEQ ID NO 125
<211> LENGTH: 30
<212> TYPE: DNA
<213> ORGANISM: Artificial Sequence
<220> FEATURE:
<223> OTHER INFORMATION: Synthetic Primer

<400> SEQUENCE: 125
gcatgatatt cccgggttgt cctagcacat 30

<210> SEQ ID NO 126
<211> LENGTH: 30
<212> TYPE: DNA

```
<213> ORGANISM: Artificial Sequence
<220> FEATURE:
<223> OTHER INFORMATION: Synthetic Primer

<400> SEQUENCE: 126

ccctctctga agtgatagat cttctggtga                                    30


<210> SEQ ID NO 127
<211> LENGTH: 29
<212> TYPE: DNA
<213> ORGANISM: Artificial Sequence
<220> FEATURE:
<223> OTHER INFORMATION: Synthetic Primer

<400> SEQUENCE: 127

cacttcagag agggtgattt gattgcagt                                     29


<210> SEQ ID NO 128
<211> LENGTH: 30
<212> TYPE: DNA
<213> ORGANISM: Artificial Sequence
<220> FEATURE:
<223> OTHER INFORMATION: Synthetic Primer

<400> SEQUENCE: 128

gttctggaag ctgttggtgt caataagaga                                    30


<210> SEQ ID NO 129
<211> LENGTH: 22
<212> TYPE: DNA
<213> ORGANISM: Artificial Sequence
<220> FEATURE:
<223> OTHER INFORMATION: Synthetic Primer

<400> SEQUENCE: 129

aataaccacg cctcaggttc tc                                            22


<210> SEQ ID NO 130
<211> LENGTH: 25
<212> TYPE: DNA
<213> ORGANISM: Artificial Sequence
<220> FEATURE:
<223> OTHER INFORMATION: Synthetic Primer

<400> SEQUENCE: 130

gagtgtttaa ggaccaatgg agaga                                         25


<210> SEQ ID NO 131
<211> LENGTH: 17
<212> TYPE: DNA
<213> ORGANISM: Artificial Sequence
<220> FEATURE:
<223> OTHER INFORMATION: Synthetic Primer

<400> SEQUENCE: 131

cttcacaact caaacat                                                  17


<210> SEQ ID NO 132
<211> LENGTH: 16
<212> TYPE: DNA
<213> ORGANISM: Artificial Sequence
<220> FEATURE:
<223> OTHER INFORMATION: Synthetic Primer

<400> SEQUENCE: 132

ttcacaacac aaacat                                                   16
```

-continued

<210> SEQ ID NO 133
<211> LENGTH: 24
<212> TYPE: DNA
<213> ORGANISM: Artificial Sequence
<220> FEATURE:
<223> OTHER INFORMATION: Synthetic Primer

<400> SEQUENCE: 133
ccctcaaacc ggataaccgt atag 24

<210> SEQ ID NO 134
<211> LENGTH: 23
<212> TYPE: DNA
<213> ORGANISM: Artificial Sequence
<220> FEATURE:
<223> OTHER INFORMATION: Synthetic Primer

<400> SEQUENCE: 134
cactggaatg gcttgttgtt agg 23

<210> SEQ ID NO 135
<211> LENGTH: 16
<212> TYPE: DNA
<213> ORGANISM: Artificial Sequence
<220> FEATURE:
<223> OTHER INFORMATION: Synthetic Primer

<400> SEQUENCE: 135
atgtctcaat gagccc 16

<210> SEQ ID NO 136
<211> LENGTH: 16
<212> TYPE: DNA
<213> ORGANISM: Artificial Sequence
<220> FEATURE:
<223> OTHER INFORMATION: Synthetic Primer

<400> SEQUENCE: 136
atgtctcaat gaaccc 16

<210> SEQ ID NO 137
<211> LENGTH: 35
<212> TYPE: DNA
<213> ORGANISM: Artificial Sequence
<220> FEATURE:
<223> OTHER INFORMATION: Synthetic Primer

<400> SEQUENCE: 137
cgtacatcat acatgttata aattaagctc aacaa 35

<210> SEQ ID NO 138
<211> LENGTH: 28
<212> TYPE: DNA
<213> ORGANISM: Artificial Sequence
<220> FEATURE:
<223> OTHER INFORMATION: Synthetic Primer

<400> SEQUENCE: 138
gcatatgcaa gtgctaagat aactttgt 28

<210> SEQ ID NO 139
<211> LENGTH: 26
<212> TYPE: DNA
<213> ORGANISM: Artificial Sequence
<220> FEATURE:

-continued

<223> OTHER INFORMATION: Synthetic Primer

<400> SEQUENCE: 139
acacatttta attactatat ataact 26

<210> SEQ ID NO 140
<211> LENGTH: 25
<212> TYPE: DNA
<213> ORGANISM: Artificial Sequence
<220> FEATURE:
<223> OTHER INFORMATION: Synthetic Primer

<400> SEQUENCE: 140
cacattttaa ttactatata tagct 25

<210> SEQ ID NO 141
<211> LENGTH: 22
<212> TYPE: DNA
<213> ORGANISM: Artificial Sequence
<220> FEATURE:
<223> OTHER INFORMATION: Synthetic Primer

<400> SEQUENCE: 141
agagcccttt ttgcatgtgc ta 22

<210> SEQ ID NO 142
<211> LENGTH: 27
<212> TYPE: DNA
<213> ORGANISM: Artificial Sequence
<220> FEATURE:
<223> OTHER INFORMATION: Synthetic Primer

<400> SEQUENCE: 142
tcgttcttat ttattgctac gcacact 27

<210> SEQ ID NO 143
<211> LENGTH: 17
<212> TYPE: DNA
<213> ORGANISM: Artificial Sequence
<220> FEATURE:
<223> OTHER INFORMATION: Synthetic Primer

<400> SEQUENCE: 143
caaaaggaca aaagtgt 17

<210> SEQ ID NO 144
<211> LENGTH: 16
<212> TYPE: DNA
<213> ORGANISM: Artificial Sequence
<220> FEATURE:
<223> OTHER INFORMATION: Synthetic Primer

<400> SEQUENCE: 144
aaaaggacga aagtgt 16

<210> SEQ ID NO 145
<211> LENGTH: 25
<212> TYPE: DNA
<213> ORGANISM: Artificial Sequence
<220> FEATURE:
<223> OTHER INFORMATION: Synthetic Primer

<400> SEQUENCE: 145
ggaaccaaga gcaagagttt ctaca 25

<210> SEQ ID NO 146
<211> LENGTH: 24
<212> TYPE: DNA
<213> ORGANISM: Artificial Sequence
<220> FEATURE:
<223> OTHER INFORMATION: Synthetic Primer

<400> SEQUENCE: 146
cgctttcctt tctggctttg agta 24

<210> SEQ ID NO 147
<211> LENGTH: 15
<212> TYPE: DNA
<213> ORGANISM: Artificial Sequence
<220> FEATURE:
<223> OTHER INFORMATION: Synthetic Primer

<400> SEQUENCE: 147
ctccttgctg cttct 15

<210> SEQ ID NO 148
<211> LENGTH: 16
<212> TYPE: DNA
<213> ORGANISM: Artificial Sequence
<220> FEATURE:
<223> OTHER INFORMATION: Synthetic Primer

<400> SEQUENCE: 148
cctcctttct gcttct 16

<210> SEQ ID NO 149
<211> LENGTH: 25
<212> TYPE: DNA
<213> ORGANISM: Artificial Sequence
<220> FEATURE:
<223> OTHER INFORMATION: Synthetic Primer

<400> SEQUENCE: 149
tccaattcac caactccttc aaact 25

<210> SEQ ID NO 150
<211> LENGTH: 25
<212> TYPE: DNA
<213> ORGANISM: Artificial Sequence
<220> FEATURE:
<223> OTHER INFORMATION: Synthetic Primer

<400> SEQUENCE: 150
caaagggaag aaagagagag agtga 25

<210> SEQ ID NO 151
<211> LENGTH: 20
<212> TYPE: DNA
<213> ORGANISM: Artificial Sequence
<220> FEATURE:
<223> OTHER INFORMATION: Synthetic Primer

<400> SEQUENCE: 151
cttccttagt tcaatatagg 20

<210> SEQ ID NO 152
<211> LENGTH: 18
<212> TYPE: DNA
<213> ORGANISM: Artificial Sequence
<220> FEATURE:
<223> OTHER INFORMATION: Synthetic Primer

<400> SEQUENCE: 152
tccttagttc aatatggg 18

<210> SEQ ID NO 153
<211> LENGTH: 23
<212> TYPE: DNA
<213> ORGANISM: Artificial Sequence
<220> FEATURE:
<223> OTHER INFORMATION: Synthetic Primer

<400> SEQUENCE: 153
cataggagaa cacgagggat gtg 23

<210> SEQ ID NO 154
<211> LENGTH: 24
<212> TYPE: DNA
<213> ORGANISM: Artificial Sequence
<220> FEATURE:
<223> OTHER INFORMATION: Synthetic Primer

<400> SEQUENCE: 154
ggcttctact ttgctcttcc tctt 24

<210> SEQ ID NO 155
<211> LENGTH: 15
<212> TYPE: DNA
<213> ORGANISM: Artificial Sequence
<220> FEATURE:
<223> OTHER INFORMATION: Synthetic Primer

<400> SEQUENCE: 155
aatgcgaaga taaag 15

<210> SEQ ID NO 156
<211> LENGTH: 14
<212> TYPE: DNA
<213> ORGANISM: Artificial Sequence
<220> FEATURE:
<223> OTHER INFORMATION: Synthetic Primer

<400> SEQUENCE: 156
atgcgaaaat aaag 14

<210> SEQ ID NO 157
<211> LENGTH: 5495
<212> TYPE: DNA
<213> ORGANISM: Glycine max
<220> FEATURE:
<221> NAME/KEY: misc_feature
<222> LOCATION: (1)..(5495)
<223> OTHER INFORMATION: k is g or t
<220> FEATURE:
<221> NAME/KEY: misc_feature
<222> LOCATION: (1)..(5495)
<223> OTHER INFORMATION: m is a or c
<220> FEATURE:
<221> NAME/KEY: misc_feature
<222> LOCATION: (1)..(5495)
<223> OTHER INFORMATION: w is a or t
<220> FEATURE:
<221> NAME/KEY: misc_feature
<222> LOCATION: (1)..(5495)
<223> OTHER INFORMATION: y is c or t

<400> SEQUENCE: 157
aaaaccctaa acctaaaccc ccaagcgctg cattggtcat ccattgttgg aacattctct 60
gattaccaac aatgagaccc ccgagaggcg gtggacgcgg cggcggattc agaggtggcc 120

```
gcgacggtgg tggtcgcggc agaggtggtt ttggtcgcgg cggaggtggt tttggtcgcg    180
gcggcggcgg cggatatcgt gacgaaggac caccctccga agtcgtaggt tgtttcttct    240
tccattttga aacttcagaa gcgtttcaat ttctatgttc tctgttgggt atttcatcaa    300
ccgtgtttga agattgaaaa aaaaaatgtg ctttgtggtg tttgctgcta atgacatgat    360
ttygtttctg ggttttgata atttgcaagg aaataacata actttatcta gcttagttaa    420
aaaaagattt ttatttttat ttttgtgttg tttatctttt taattcattt ggtgtatatg    480
cagaggtgtc atcttttatg catgcatgcg agggagatgc agtgacaaag cttacaaatg    540
agaaagttcc ctttttcaat gctcctattt atctgaaaaa catgactcag attgggaaag    600
ttgatgaaat atttggcccc atcaatgaag ctgtgggttt ctctcatttt ttgtttgttt    660
gttttaacat gttggttgct tctgttattt tttttggtct gttatggaac tgggttttga    720
tgttatctgg tgcttcgttg gtgaacatgc agtacttctc aattaagatg atggaaggga    780
ttgttgctac ttcttattca tccggcgaca agttttatat tgatccaagg aaactgttgc    840
ctcttgcaag atttcttcca caacccaagg gacaatcagc tggtagaggt ggaggtggag    900
gtggtcgtgg tggatgtaga ggtggccgtg gaggtggtgg ttttcgtgga aggggcgctc    960
caaggggtgg gagaggtggt cctcccaggg gtggtgcagg ctttttcttt ttcttcttct   1020
tcttcttctt tattttctca ttttgccaaa ctaaaatagt tgtgttggta gctttggcaa   1080
agatgttttc agcaggccat aagatcaaag ggacagtggt gttgatgccc aagaatgagt   1140
tggaagttaa ccctgatggc tcagcagttg acaaccttaa tgctttcttg ggccgwagtg   1200
tctcccttca gctcattagt gctaccaagg ctgatggtta attaatttct tcwtcgtttc   1260
actttttcc atcatcatca tccacaatca tcactttcta tattaaaaat taactttaat    1320
ttctatatac gaaaagtaag tgtaaagagt ttaaataatt tttgtaaaat aktaatttct   1380
gattcaayga tagtatacac attttttaca tttttaattc atagagggtt ttgttttcta   1440
ttagaaatat atcacgtagt aatacataac caaagatatt tatatagttt aaacttactc   1500
ggtacgtacg taacatagta ttattawtat gtgtgtatga tctgtttgta gcamatggaa   1560
aaggaaaagt tggaaaggat acgttcttgg aagggattaa tacttcgtta ccaactttgg   1620
gagcaggaga gtctgcattc aatattcatt ttgaatggga cggaagcatg ggaatccccg   1680
gtgcgtttta cataaagaac tacatgcaag ttgagttctt cctcaagagt ttgactcttg   1740
aagccatttc aaaccaagga accatccgct ttgtttgcaa ctcatgggtt tataacacta   1800
aactttacaa aagcgtgcgc attttctttg ccaaccatgt aagctcttta gcaattagta   1860
gtttaattac aaaagtgtgt gtgtgtgtga aatgtctaat ggcaagttct tcaagtttaa   1920
gctaagaatt aaaaaattca atttaatgta atgtagacat atgtacctag tgagacacca   1980
gcaccacttg tggagtacag agaagaagaa ttgaagagtt taagaggaaa tggaacggga   2040
gagcgcaagg aatatgatag gatctatgat tatgatgtct acaatgattt gggcaaccca   2100
gataagagtg aaaagttagc tcgtccagtt cttggagggt ctagcacctt tccctaccct   2160
cgtaggggaa gaactggtcg aggtccaaca gttacaggtt agtcttctat ggttctatat   2220
aatttaaatg aattgtaaca ttgacttttt ataatgttat ggtcagcgta gtacaacata   2280
ttgcttgggt atatgtgaca cgttataaat taattttgca ctatgattct gattattttt   2340
atttttttg gatgattaag tttttacaca ttgttgtttc ctaatcaatt tcaattcaac    2400
agacccgaat actgagaaac aaggcgaagt attttatgtt ccaagagatg aaaatttagg   2460
```

-continued

```
tcacttgaag tctaaggatg ctcttgagat tggaacaaaa tctttatctc aaattgtcca   2520
gccggcgttc gaatctgcgt tcgatttgaa atccacgcca attgagtttc atagcttcca   2580
agatgtgcat gacttgtatg aaggtggaat taagcttcct agagatgtaa ttagcacaat   2640
tatcccctta ccagtgatca aagaactcta tcgtaccgat ggtcaacaca tcctcaagtt   2700
tccacaacct cacgtcgttc aaggtgtgat aaataaatat aataaaccac tcatacttga   2760
aatcttgaat taatcaatga cataataaat ataataaacc actgatactt gaaatcttga   2820
attaattaat gacattttgg tcatacaaat cgtatcgtat tcacgaacaa attcaaaact   2880
cattatgttt tttatgaaat ggttattcca tttaataagg attttctttt tattattaat   2940
ttgggtagtg agtcagtctg catggatgac tgatgaagaa tttgctagag agatgattgc   3000
tggtgtaaat ccctgcgtaa ttcgtggtct tgaagtaagt tcaaatattt atttataaaa   3060
tcaaatttga tgtccacgta aaattaggta gtatatcgcc agtaataaac taaaatacta   3120
aatggttgtt cttctttaat taaatggatt gtaggagttc cctccaaaaa gtaatctgga   3180
tcctgcaatc tatggtgatc aaagcagtaa gataacagca gattcccttg atctagatgg   3240
gtacacaatg gacgaggtaa acatgcgaag cgaaggaatt gatacaataa ttttcctctt   3300
aaagtaatta attaaaacta attgaatttt gtggtacagg cacttggtag tcgaaggtta   3360
tttatgttag attaccatga tatcttcatg ccatatgtga ggcagataaa tcagctgaat   3420
tctgccaaga cttatgcgac aaggactatc cttttttga gagaagatgg aactttaaag   3480
ccagtggcca tcgaattaag tttgccacat tctgctgggg atctgtcagc tgccgtcagt   3540
caagtcgtct tacctgctaa ggaaggtgtt gagagcacaa tttggctact agccaaagct   3600
tatgtcatcg taaatgactc ttgctaccat caactcatga gccattggta taaattttca   3660
ttttcatttt cattgctata tatcaacata tatagataaa ttcaatctct aatccctctc   3720
tctcaagtgt atattaatta cttttgattt cttcataggt taaatactca tgcggcgatg   3780
gagccattcg tcatagcaac acaccgacat cttagcgtgc ttcacccaat ttacaagctt   3840
ctgactcctc actatcgtaa caacatgaac atcaacgcac ttgccaggca atctctaatt   3900
aatgctaatg gcataataga gacaaccttt ttgccctcaa agtattctgt ggagatgtct   3960
tcggcggttt ataagaattg ggttttcact gatcaagcac tacctgcaga tcttatcaag   4020
aggtaattaa ttaagtaaat ctctctatat cactagaaaa aaaatgtgac ataaaggttt   4080
gaaatatata ggtatacatt ttgttacaaa gcataatgat ggatgcatgt atatattata   4140
ttttgtttga cttagaggag tggcaattaa ggatccatca accccacatg gagttcgtct   4200
tctgatagag gactatcctt atgccgctga tggactggag atatgggctg caattaagac   4260
atgggttcaa gaatatgtgc ccttgtacta tgcaagagat gatgatgtca aaaatgattc   4320
tgaactccaa cattggtgga aagaagctgt agagaaaggc catggtgatt tgaaagacaa   4380
gccatggtgg cctaagttgc agacacttga agaccttgtt gaagtttgcc tcattatcat   4440
atggattgct tcagctctcc atgcagccgt taattttggt cagtatcctt atggaggttt   4500
gataatgaac cgcccaactg cttctagaag gttgcttcct gagaaaggca ccccagaata   4560
tgaagaaatg attaataacc atgaaaaggc ttatttgaga acaattacat caaagttgcc   4620
gactctcatt agcctttcag tgatagagat cttgtcgaca catgcttctg atgaggtcta   4680
ccttggccag agggacaacc cacattggac ctctgattca aaagcattac aagcctttca   4740
aaagtttgga aacaagctca aggaaattga ggaaaaactt gtgaggagga acaatgatcc   4800
gagtctgcag ggcaatcgac ttggcccggt tcaactgcca tacactttgc tttatcctag   4860
```

cagtgaggaa gggttaactt ttaggggaat tccaaatagc atctctatct aagggagcct 4920
gtggtttact ctaattactc tatatatagt gcatgtgtac cttccaataa aaaagatgca 4980
agactagaga tccgataaat cttgcatctt atctaatgtt tcaattatct tgtgttttaa 5040
ttaatgttgt aattgagctc acagtttggt tgtggtttgc aaataataag agcagtgagc 5100
actattagtt tgtgtttagc tcctgtcatc atgtttggta ttatacattt tgcagattac 5160
gtaacacaaa tttatgttat tagtaaaaaa actgtattgt acgaatattt tgtattataa 5220
gtatataaga aataaaaatt attagtatta gtgtttcagg ggaaggggga gatcatagag 5280
caattttatg taatgttttt cacattgctg cagttttttt cctttggaga taacatagat 5340
gttgaattgg ctttttattt cttatgcatc gagttcatgt tggttgatta tgttgttatc 5400
attatgggga agtcgattga tttgtgtagt ctctatagaa attgtgcttg attctatccc 5460
tctcaaatcg aaatggaaag tggaaactgg aaaaa 5495

<210> SEQ ID NO 158
<211> LENGTH: 3856
<212> TYPE: DNA
<213> ORGANISM: Glycine max

<400> SEQUENCE: 158
attttctgat tttagcaaat taaaatagta gtgttattgg taggttttgg caaagatgtt 60
ttcagttcca ggggtgtcgg gaatcctgaa cagaggagga gggcataaga taaaagggac 120
agtggtgttg atgaggaaga atgtgttgga cttcaacagc gtggctgatc ttactaaagg 180
aaatgttggg ggactcatag gcaccggcct caacgttgtt ggctcaacac ttgataacct 240
cactgctttc ttgggccgaa gtgtcgccct acagctcatt agtgctacca aacctcttgg 300
ttcatttctt cttccttcca cacaatcaat aacttctata ttcaaaatta agtgtttaat 360
ctctatactc tcattcattt cattcaatga aaaaaaaatc ataagacttt taactaaaat 420
taacctatgt aaagaatcac aaacaaaaaa ctatataata ttaagtttat ttactttttt 480
tataatgaca aaaaaaatta ttgtatatgg tgcacaaatt tttgtactct taaaaatata 540
tcactttata catagccaaa catatttatt ttgtatagta ttaacttatt tgggtacgta 600
ccttaataat attattatgt gtgtatgtat ggtctgtttg tagcaaatgg aaaaggaaaa 660
gttggaaagg atacgttctt ggaagggatt attgtgtcgt taccaacttt gggagcaggg 720
gagtctgcat tcaatattca gtttgaatgg gacgaaagca tgggaatccc cggtgcgttt 780
tacataaaga actacatgca agttgagttt tacctcaaga gtttgactct tgaagacgtt 840
ccaaaccaag gaaccattcg ctttgtttgc aactcatggg tttataacac taaactttac 900
aaaagcgtgc gcattttctt tgccaaccat gtaagctatt tatattacgt acttagctag 960
tagtttataa ttaaaattca gtatgtatat atatatatag ttcatttgtc cgtctctaat 1020
ggcaagatct ttaatacgtt aatttaatga attgtagaca tatgttccaa gtgagacacc 1080
agcagcactt gtggggtaca gagaagaaga attgaagaat ttaagaggag atggaaaagg 1140
agagcgcaaa gaacatgata ggatctatga ttatgatgtc tacaatgatt tgggcaatcc 1200
agatcacggt gaaaattttg ctcgcccaat tcttggaggg tctagcactc atccctaccc 1260
tcgtagggga agaactggtc gatatccaac aaggaaaggt tagttttcta tatatgcttc 1320
tatttgttta agtgaattga tattatatgt gtgaagctaa tttaatttat tttagcattg 1380
ttcttttacg atgttatggc cagccaggtt caaacaagtg aaagtatcta tgcgtacata 1440

-continued

```
tttatttttt attaaaatga ttttatgtat ataagttatt ttgtgctatg attctgattt   1500
atttttccta atcaatttca acagatcaga attctgagaa gccaggcgaa gtttatgttc   1560
caagagatga aaattttggt cacttgaagt cctcggattt tcttgcatat ggaataaaat   1620
ctttatctca atatgtctta ccggcgttcg aatctgtttt cgatttgaac ttcacgccaa   1680
atgagtttga tagcttccaa gatgtgcgtg acctccacga aggtggaatt aagcttccta   1740
cagaagtaat tagcacaatt atgcccttac cggtggtcaa agaactcttt cgtacagatg   1800
gtgaacaagt cctcaagttt ccaccacctc atgtcattca agtgagtaag tctgcatgga   1860
tgaccgatga agaatttgca agagagatgg ttgcgggtgt aaatccatgc gtaattcgtg   1920
gtcttcaaga gtttcctcca aaaagcaatc tggatcctac aatctatggt gagcaaacca   1980
gtaagataac agcagatgcc cttgatctag atggatacac agtggacgag gtaaacatat   2040
tcaagtctca taatttaacc acaggaagaa ggaactttaa gtaattaaaa gtgcttgtgt   2100
atgatctgat tacaataaat ttaatttgtg gcacaggcac tagcaagtcg gaggttattt   2160
atgttagatt accatgatgt attcatgcca tatataaggc ggataaatca gacatatgcc   2220
aaggcttatg cgacaaggac tatccttttt ctgagagaaa atggaacctt aaagccagtg   2280
gccatcgaat taagtttgcc acatcctgct ggggacctgt caggtgctgt cagtcaagtc   2340
atcttacctg caaaagaagg tgttgaaagt acaatttggc tactggccaa agcttatgtg   2400
gtcgtaaatg actcttgcta tcatcaactc atgagccatt ggtatataaa acaattcaat   2460
tcaatctcca tctatgatgt atgttatgtc tcaattttat tttattttta tttttttattt   2520
tgttcatagg ttaaatactc aagcggtgat tgagccattc atcatagcaa caaaccgaca   2580
ccttagtgct cttcacccaa tttataagct tctaactcct cactaccgtg acaccatgaa   2640
catcaacgca cttgctaggc aatctctcat taatgctgat ggcataatag agaaatcttt   2700
tttgccctca aagcattccg ttgagatgtc ttcagcggtt tataagaatt gggttttcac   2760
tgatcaagca ctacctgcag atcttatcaa gaggtaatta atctctctaa actctaaaca   2820
taaaactatg aaatataggt acatagtttg ttattgattt atattttgtt tgattcagag   2880
gagtggcaat taaggatcca tctgccccac atggacttcg acttctgata gaggactacc   2940
cttatgctgt tgatgggcta gagatatggg ctgcaattaa gacatgggtc caagaatatg   3000
tgtccttgta ctatgcaaga gatgatgatg tcaaacctga ttctgaactc caacagtggt   3060
ggaaagaagc tgtagagaaa ggtcatggtg atctgaaaga caagccatgg tggcctaagt   3120
tgcaaacaat tgaagagctt gttgaaattt gcaccattat catatggact gcttcagccc   3180
tccatgcagc cgttaacttt ggtcaatatc catatggagg tttcattctg aatcgcccaa   3240
cttcttctag aaggttgctt cctgagaaag gcaccccaga atatgaagaa atggtgaaaa   3300
gtcatcaaaa ggcttatttg agaactatta catcaaagtt tcaaactcta gttgaccttt   3360
cagtgataga gatcttgtca aggcatgctt ctgatgaggt ctaccttggc caaagggaca   3420
acccacattg gacctctgac tcaaaagcat tacaagcctt tcaaaaattt ggaaacaagc   3480
tcaaagaaat tgaggaaaaa cttgcaagga agaacaatga tcaaagtctc tccaatcgac   3540
ttgggccggt tcaactgcca tacactttgc tccatcctaa cagtgaggaa gggttgactt   3600
gcagggggat tcctaatagc atctctatct aagggagcat gtggtctact ttaattacag   3660
tactgtacct accttccaat aaaaaagatg caaggctaga gatccaataa atcttgcatc   3720
ctatctaatg tttcaattat cttgtgtttt aatgctgtaa tggagcctac aatttgcaaa   3780
ttaattaaga gcaccgagca ctattagttt gcgtttagct tctgtcatgt ttattaagat   3840
```

atatttcgca gattgt 3856

<210> SEQ ID NO 159
<211> LENGTH: 25
<212> TYPE: DNA
<213> ORGANISM: Artificial Sequence
<220> FEATURE:
<223> OTHER INFORMATION: Synthetic Primer

<400> SEQUENCE: 159
gctatcatca actcatgagc cattg 25

<210> SEQ ID NO 160
<211> LENGTH: 25
<212> TYPE: DNA
<213> ORGANISM: Artificial Sequence
<220> FEATURE:
<223> OTHER INFORMATION: Synthetic Primer

<400> SEQUENCE: 160
gtgtcggttt gttgctatga tgaat 25

<210> SEQ ID NO 161
<211> LENGTH: 18
<212> TYPE: DNA
<213> ORGANISM: Artificial Sequence
<220> FEATURE:
<223> OTHER INFORMATION: Synthetic Primer

<400> SEQUENCE: 161
caatcaccgc ttgagtat 18

<210> SEQ ID NO 162
<211> LENGTH: 17
<212> TYPE: DNA
<213> ORGANISM: Artificial Sequence
<220> FEATURE:
<223> OTHER INFORMATION: Synthetic Primer

<400> SEQUENCE: 162
aatcaccgca tgagtat 17

<210> SEQ ID NO 163
<211> LENGTH: 3524
<212> TYPE: DNA
<213> ORGANISM: Glycine max
<220> FEATURE:
<221> NAME/KEY: misc_feature
<222> LOCATION: (1)..(3524)
<223> OTHER INFORMATION: k is g or t
<220> FEATURE:
<221> NAME/KEY: misc_feature
<222> LOCATION: (1)..(3524)
<223> OTHER INFORMATION: r is a or g
<220> FEATURE:
<221> NAME/KEY: misc_feature
<222> LOCATION: (1)..(3524)
<223> OTHER INFORMATION: w is a or t
<220> FEATURE:
<221> NAME/KEY: misc_feature
<222> LOCATION: (1)..(3524)
<223> OTHER INFORMATION: y is c or t

<400> SEQUENCE: 163
tagcctaagt acgtactcaa aatgccaaca aataaaaaaa aagttgcttt aataatgcca 60
aaacaaatta ataaaacact tacaacaccg gatttttttt aattaaaatg tgccatttag 120

-continued

```
gataaatagt taatattttt aataattatt taaaaagccg tatctactaa aatgattttt    180
atttggttga aaatattaat atgtttaaat caacacaatc tatcaaaatt aaactaaaaa    240
aaaaataagk gkacgkggtt aacattagta cagtaatata agaggaaaat gagaaattaa    300
gaaattgaaa gcgagtctaa tttttaaatt atgaacctgc atatataaaa ggaaagaaag    360
aatccaggaa gaaaagaaat gaawccatgc atggtcccct cgtcatcacg agtttctgcc    420
atttgcaata gaaacactga aacacctttc tctttgtcac ttaattgaga tgccgaagcc    480
acctcacacc atgaacttca tgaggtgtag cacccaaggc ttccatagcc atgcatactg    540
aagaatgtct caagctcagc accctacttc tgtgacgtgt ccctcattca ccttcctctc    600
ttccctataa ataaccacgc ctcaggttct ccgcttcaca actcaaacat tctctccatt    660
ggtccttaaa cactcatcag tcatcaccat ggccaagcta gtttttttccc tttgttttct    720
gcttttcagt ggctgctgct tcgctttcag ttccagagag cagcctcagc aaaacgagtg    780
ccagatccaa aaactcaatg ccctcaaacc ggataaccgt atagagtcag aaggagggct    840
cattgagaca tggaacccta acaacaagcc attccagtgt gccggtgttg ccctctctcg    900
ctgcaccctc aaccgcaacg cccttcgtag accttcctac accaacggtc cccaggaaat    960
ctacatccaa caaggtccat cttgtccaaa cttcacatat aaatatataa tagacttaaa   1020
tatgtttaag ggtttgataa atgagggaat tttattttag atttttaata attttttttg   1080
ttttgagttt ttatatatta aaatttttgt tttgatttct tccatatgac gtaacataat   1140
catatcattg ataatgttgg gttcctaatt tttgtttgtt tgttgttttg taatatgaat   1200
aggtaagggt atttttggca tgatataccc gggttgtcct agcacatttg aagagcctca   1260
acaacctcaa caaagaggac aaagcagcag accacaagac cgtcaccaga agatctataa   1320
cttcagagag ggtgatttga tcgcagtgcc tactggtgtt gcatggtgga tgtacaacaa   1380
tgaagacact cctgttgttg ccgtttctat tattgacacc aacagcttgg agaaccagct   1440
cgaccagatg cctagggtga gccacatagc aatattagat attataattc tttaaaggtt   1500
taaatatcat tttagttcgt ggagttgcac tttctaattt agtacctata gattaaaata   1560
tgccaattga atccttatag ttgtgttttt ttatccaatt tggttcttgt cttgaaataa   1620
atggacaata ttgtagctga taaaaaaagg aaactggact acattgtaac gttaagatta   1680
gaattcttaa gttctaatac tagctggtta cagattgaca actatttgtt ttgacaattc   1740
ttggcagaga ttctatcttg ctgggaacca agagcaagag tttctaaaat atcagcaaga   1800
gcaaggaggt catcaaagcc agaaaggaaa gcatcagcaa gaagaagaaa acgaaggagg   1860
cagcatattg agtggcttca ccctggaatt cttggaacat gcattcagcg tggacaagca   1920
gatagcgaaa aacctacaag gagagaacga aggggaagac aagggagcca ttgtgacagt   1980
gaaaggaggt ctgagcgtga taaaaccacc cacggacgag cagcaacaaa gaccccagga   2040
agaggaagaa gaagaagagg atgagaagcc acagtgcaag ggtaaagaca aacactgcca   2100
acgcccccga ggaagccaaa gcaaaagcag aagaaatggc attgacgaga ccatatgcac   2160
catgagactt cgccacaaca ttggccagac ttcatcacct gacatctaca accctcaagc   2220
cggtagcgtc acaaccgcca ccagccttga cttcccagcc ctctcgtggc tcagactcag   2280
tgctgagttt ggatctctcc gcaaggtacg tacatcattc atcaaagatc aacatacatt   2340
tatacattaa actaatattt gttgccaaat atttattaat tttattgata attaattttt   2400
ttagaaaatt tgtttgatca cttttaatgg agtctttcat cttaattaca ttatttatac   2460
ttagactaat gatttattga ttaataataa tcttagatac actataaaat gtgtgacgga   2520
```

gttatcttaa cacttgcatg gattctatct tttctgtctt tatatataga aatagagaga 2580
aaaaaaaaga aaagattgat gaaaaaagca aaacaaaaaa tagtattatt ataaaaatat 2640
tggatgaatt tgttgtgact cttgcatgca ttgatgtayg rtgcagaatg catgttcgtg 2700
ccacactaca acctgaacgc gaacagcata atatacgcat tgaatggacg ggcattgata 2760
caagtggtga attgcaacgg tgagagagtg tttgatggag agctgcaaga gggacgggtg 2820
ctgatcgtgc cacaaaactt tgtggtggct gcaagatcac agagtgacaa cttcgagtat 2880
gtgtcattca agaccaatga tacacccatg atcggcactc ttgcaggggc aaactcattg 2940
ttgaacgcat taccagagga agtgattcag cacactttca acctaaaaag ccagcaggcc 3000
aggcagataa agaacaacaa ccctttcaag ttcctggttc cacctcagga gtctcagaag 3060
agagctgtgg cttagagccc tttttgtatg tgctacccca cttttgtctt tttggcaata 3120
gtgctagcaa ccaataaata ataataataa taatgaataa gaaaacaaag gctttagctt 3180
gccttttgtt cactgtaaaa taataatgta agtactctct ataatgagtc acgaaacttt 3240
tgcgggaata aaaggagaaa ttccaatgag ttttctgtca aatcttcttt tgtctctctc 3300
tctctctctt tttttttct ttcttctgag cttcttgcaa aacaaaaggc aaacaataac 3360
gattggtcca atgatagtta gcttgatcga tgatatcttt aggaagtgtt ggcaggacag 3420
gacatgatgt agaagactaa aattgaaagt attgcagacc caatagttga agattaactt 3480
taagaatgaa gacgtcttat caggttcttc atgacttgga gctc 3524

<210> SEQ ID NO 164
<211> LENGTH: 3640
<212> TYPE: DNA
<213> ORGANISM: Glycine max
<220> FEATURE:
<221> NAME/KEY: misc_feature
<222> LOCATION: (1)..(3640)
<223> OTHER INFORMATION: d is a or g or t
<220> FEATURE:
<221> NAME/KEY: misc_feature
<222> LOCATION: (1)..(3640)
<223> OTHER INFORMATION: r is a or g
<220> FEATURE:
<221> NAME/KEY: misc_feature
<222> LOCATION: (1)..(3640)
<223> OTHER INFORMATION: w is a or t

<400> SEQUENCE: 164
tgaaaggaaa gaaagaagca gaggaagaaa agaaatgaaa ccatgcatgg tccccacccc 60
aggacatcat gggtttctgc catttgcaat acaaacactg aaacaccttt ctctttgtca 120
cgtaatcgag attccgaagc caccttacac cattaactta atagtgtaag acagaagggt 180
tccatagcca tgcatactga agaatgtctt aagctcagca ccccacttct gagacgtgtc 240
cctcattcac cttcctctct tccctataaa taaccacgcc tcaggttctc cgcttcacaa 300
cacaaacatt ctctccattt gtccttgaat ataatactca gcatggctaa gcttgttctt 360
tccctttgtt ttctgctttt cagtggctgc tgcttcgctt tcagtttcag agagcagcca 420
cagcaaaacg agtgccagat ccaacgcctc aatgccctca aaccggataa ccgtatagag 480
tcagaaggtg gcttcattga gacatggaac cctaacaaca agccattcca gtgtgccggt 540
gttgccctct ctcgctgcac cctcaaccgc aacgcccttc gcagaccttc ctacaccaac 600
gctccccagg agatctacat ccaacaaggt ttttttattt tatcatcaaa tattagttta 660
ttagttttat taaaaatatt aatcgaaaaa aatccaactt acaaccttta ttcaacaagg 720

-continued

```
ttcattttat ccacacttta taatacatac atacatatat atatatatat atatatatat    780
atatatatat atatatatat atatatatat atatatatat atatatatat atatatgtat    840
gtatgtatga ttgatttact aacgtatata cctatatttt tttagcagag gactgttatt    900
tagtacaaca aatcattgca caaattgcaa gaaaagaaac atcaacggct gaacttttgt    960
tcaaaacaaa tacttaattg gaaaataata aaataaaaac tggaaattga cttaatgcac   1020
tcttcatgcg ttttttaact aaaactgttt cctacattaa caaatacttg cgggatttat   1080
caacttacat attcttatct ttttagtatg aatacattag caaattatat cattgtatat   1140
tttaagatat tctttatcta taattcactg gtaaaaaaac catattagca aaaccctcaa   1200
gagtaacgtt aaggacatcg ataatgtttt gtttgtatca gttttcagaa ttaaaacatt   1260
ttgaaacgaa aatggttatt atagtaatgt ttttgtgatt gtttaatgtg aataggtagt   1320
ggtatttttg gcatgatatt cccgggttgt cctagcacat ttgaagagcc tcaacaaaaa   1380
ggacaaagca gcaggcccca agaccgtcac cagaagatct atcacttcag agagggtgat   1440
ttgattgcag tgccaaccgg ttttgcatac tggatgtaca acaatgaaga cactcctgtt   1500
gttgccgttt ctcttattga caccaacagc ttccagaacc agctcgacca gatgcctagg   1560
gtacgtgagc cacatatata gcattagata ttagaattct ttaaagattt aaatatcttt   1620
ttggtttgtt tgcagttgca ctttttaatt tagtatctat agattaaatg tcaattttat   1680
cttcataatt gtgttttttt atgcaatttg gtcctcgtgg tgaaatcact ttaaataact   1740
ggaaaaaatt gtagctgata aaaaaaagaa attggacaac gttgtaacat gcattaagat   1800
tagaactctt aagttctaat actggttaca gaattaacaa gtatttgttt tgataaaata   1860
tacacttggc agagattcta tcttgctggg aaccaagagc aagagtttct acagtatcag   1920
ccacagaagc agcaaggagg tactcaaagc cagaaaggaa agcgtcagca agaagaagaa   1980
aacgaaggag gcagcatatt gagtggcttc gccccggaat tcttggaaca tgcgttcgtc   2040
gtggacaggc agatagtgag aaagctacaa ggtgagaacg aagaggaaga gaagggtgcc   2100
attgtgacag tgaaaggagg tctcagcgtg ataagcccac ccacggaaga gcagcaacaa   2160
agacccgagg aagaggagaa gccagattgt gacgagaaag acaaacattg ccaaagccaa   2220
agcagaaatg gcattgacga gaccatttgc acaatgagac ttcgccacaa cattggccag   2280
acttcatcac ctgacatctt caaccctcaa gctggtagca tcacaaccgc taccagcctc   2340
gacttcccag ccctctcgtg gctcaaactc agtgcccagt ttggatcact ccgcaaggta   2400
cttacatcat taattcatgt tataaaagct caaaaaatgt taaaatgata ctaatagtta   2460
tatatagtaa ttaaaatgtg tgacaaaatc atcttaacac ctgcatgcat atgcattatt   2520
ttttgtcttt ttttggtgca aatatgcgct gtatgtctat atatatatat gttatggaaa   2580
atgttaacca gttttttttgg atattggtta aggaatgaga aataatttta ctaagattra   2640
gttttaatat gatcttcata ataaacattt ttwaaatttt tttaattaat gtacttagta   2700
cactaattaa caaaatcata tatatatgat tttcatagga ttgcaaagaa aagagatatg   2760
attgagagat ggaataatta ctgtgataat aaaaagatat gttatgatta acgtacactt   2820
gatgtatggt gcagaatgct atgttcgtgc cacactacaa cctgaacgca aacagcataa   2880
tatacgcatt gaatggacgg gcattggtac aagtggtgaa ttgcaatggt gagagagtgt   2940
ttgatggaga gctgcaagag ggacaggtgt taattgtgcc acaaaacttt gcggtggctg   3000
caagatcaca gagcgacaac ttcgagtatg tttcattcaa gaccaatgat agaccctcga   3060
tcggcaacct tgcaggtgca aactcattgt tgaacgcatt gccggaggaa gtgattcagc   3120
```

aaacttttaa cctaaggagg cagcaggcca ggcaggtcaa gaacaacaac cctttcagct 3180
tcctggttcc acctaaggag tctcagagga gagttgtggc ttagagccct ttttgcatgt 3240
gctaccacac tttcgtcctt ttgggcacta gttagtgtgc gtagcaataa ataagaacga 3300
ataaaacaac aaaggctttg ctgccctttg ttaagtataa aataacgggt aatgtaattg 3360
tacccttgtg taatgagtca ctcaagtacc tatgcgggaa aatcataaat taaaagagaa 3420
atttcaatga attttctgtc aaatctcttt tctttttatt cttttgtttc tttcttatcc 3480
ttcttgcaga acaaaataag gaaaatagta ttgaaaacaa ttggtccaaa tgatagctag 3540
ctttgacaat gatatataat agtttttatt gtagaatttc gtgacatgtt gtgcgctcta 3600
atttatttgt aagaaccttc attggtttcg tatgcgtttd 3640

<210> SEQ ID NO 165
<211> LENGTH: 3544
<212> TYPE: DNA
<213> ORGANISM: Glycine max
<220> FEATURE:
<221> NAME/KEY: misc_feature
<222> LOCATION: (1)..(3544)
<223> OTHER INFORMATION: r is a or g
<220> FEATURE:
<221> NAME/KEY: misc_feature
<222> LOCATION: (1)..(3544)
<223> OTHER INFORMATION: s is c or g

<400> SEQUENCE: 165
ctatacaata taagatcata gtactgacaa aatgcacagt aaaacagttc aaattgagaa 60
ggattsttaa cacaccatag tatttaatat atatctttac agagacaatt atgctggagg 120
attcaggcaa agattatata ttgtggattt gttttttaat aattaacgca tcatatgaaa 180
gatcgatgat atatactaat ggttataaga aaaatattta acagtttcta taaccttttt 240
cttttatctt ttactgtaat attatttatt ttatttcaca tttttaatca gcttatctca 300
tttataaacg aaattgtata aaaatataca tgatgaactg aatagaacaa tattgatctg 360
atattctcat attgtataag aggatagact ttgagacgcg gagaatctgt aggaggggac 420
cattcagagt gcctccaatt ttggtgttgt tcattgtacc attgcaaata taaacgaagc 480
atgcatgctt atgtatgagg tgtaacaaaa ttggaaacaa tagccatgca aggtgaagaa 540
tgtcacaaac tcagcaaccc ttattcattg acgtgtccct cagtcactct cctctcatac 600
ctataaatca ccactcctca tgttctttcc aattcaccaa ctccttcaaa cttaattatt 660
aacacttcct tagttcaata trgggaagcc cttcactctc tctctttctt ccctttgctt 720
gctactcttg tcgagtgcat gctttgctat tagctccagc aagctcaacg agtgccaact 780
caacaacctc aacgcgttgg aacccgacca ccgcgttgag tccgaaggtg gtttgattca 840
aacatggaac tctcaacacc ctgagctgaa atgcgccggt gtcactgttt ccaaactcac 900
cctcaaccgc aatggcctcc acttgccatc ttactcacct tatccccgga tgatcatcat 960
cgcccaaggt aatcatatat aaggagtgct tctaacacac atatcagaaa gagtatcacc 1020
agcatttctc agtgtatatt aatccatttg tcaccacttg ttcaaatttc aacatcacat 1080
taccatagat catttactaa agataataat gatttaagta aatagtatct ctatagtaaa 1140
ttttacatga ttatttaact acaaattatt attattatat atagaatgac tttgttgaca 1200
tatcaatcac cttaaaagtt ttattaagtt atatatatca actaagatat ctgattaaat 1260
aaaaatgtga ttgttttgtt tggtgatgat tgatgtacag ggaaaggagc acttggagtt 1320

-continued

```
gcaattccag gatgtcctga gacgtttgag gagccacaag aacaatcaaa cagaagaggc   1380
tcaaggtcgc agaagcagca gctacaggac agtcaccaga agattcgtca cttcaatgaa   1440
ggagacgtac tcgtgattcc tcctggtgtt ccttactgga cctataacac tggcgatgaa   1500
ccagttgttg ccatcagtct tcttgacacc tctaacttca ataaccagct tgatcaaacc   1560
cctagggtaa ttatcaattc aatttcattt actattaaca aaaaccatgt tctcctcact   1620
tgttaatttt ttcactttca ggtattttac cttgctggga acccagatat agagtaccca   1680
gagaccatgc aacaacaaca acagcagaaa agtcatggtg gacgcaagca ggggcaacac   1740
cagcaggagg aagaggaaga aggtggcagc gtgctcagtg gcttcagcaa acacttcttg   1800
gcacaatcct tcaacaccaa cgaggacata gctgagaaac ttcagtctcc agacgacgaa   1860
aggaagcaga tcgtgacagt ggaaggaggt ctcagcgtta tcagccccaa gtggcaagaa   1920
caacaagatg aagatgaaga tgaagacgaa gatgatgaag atgaacaaat tccctctcac   1980
cctcctcgcc gaccaagcca tggaaagcgt gaacaagacg aggacgagga cgaagatgaa   2040
gataaacctc gtcctagtcg accaagccaa ggaaagcgtg aacaagacca ggaccaggac   2100
gaggacgaag atgaagatga agatcaacct cgcaagagcc gcgaatggag atcgaaaaag   2160
acacaaccca gaagacctag acaagaagaa ccacgtgaaa gaggatgcga gacaagaaac   2220
ggggttgagg aaaatatctg caccttgaag cttcacgaga acattgctcg cccttcacgc   2280
gctgacttct acaaccctaa agctggtcgc attagtaccc tcaacagcct caccctccca   2340
gccctccgcc aattccaact cagtgcccaa tatgttgtcc tctacaaggt atgtaattca   2400
cctcattcat attactaagt aatcaacatg aaactaatat acgtacatac ttacacatct   2460
accagtaatt tttccgtgga tattcaattg tcaattagtc tatcttgaga aaattaagaa   2520
ataaaaagaa agcacaaaag ggaaaaatct ttatgtcata aatcatatga tataataatt   2580
tagaagacat ataaaaatgt cagtaagtat gttgtagggt tggattcctt taaatgtcat   2640
taaaatatca tttgatatgg gtaattcttt agtgattctc taggggtagt tgaactgtaa   2700
tgtattataa ttgtgcattg atttttatga gttactttaa catgtcaatg aagacttatt   2760
tgataataat tatagttact tgttggttct actactttta ataaaaaaat aataaaaata   2820
ttggtgtaaa tatataatat ataataataa tgatgatgat acgtaacaca tgttattata   2880
tccatgcaga atggaattta ctctccacat tggaatctga atgcaaacag tgtgatctat   2940
gtgactcgag gacaaggaaa ggttagagtt gtgaactgcc aagggaatgc agtgttcgac   3000
ggtgagctta ggaggggaca attgctggtg gtaccacaga acttcgtggt ggcggagcaa   3060
gccggagaac aaggattcga atacatagta ttcaagacac accacaacgc agtcactagc   3120
tacttgaagg atgtgtttag ggcaattccc tcagaggttc ttgcccattc ttacaacctt   3180
cgacagagtc aagtgtctga gcttaagtat gaaggaaatt ggggtccttt ggtcaaccct   3240
gagtctcaac aaggctcacc ccgtgttaaa gtcgcataaa tgacaagcat gatggtgtga   3300
ggatgaggcc atcttatgaa ataataacaa ataaataaat tttgtatgat aataaaaagt   3360
atggcccatg taccatccca gcgagcctat gtttatatct gagtggcgtt gtacctttca   3420
atcgccttaa taaaatgtca gtcttcacgt tttgtcttta ttctgtgttt attttctttt   3480
ttgtgggcaa gctagctttt atctactttt aaatgagtaa tactgattat atgtttactg   3540
gasg                                                                3544
```

<210> SEQ ID NO 166
<211> LENGTH: 3355

<212> TYPE: DNA
<213> ORGANISM: Glycine max
<220> FEATURE:
<221> NAME/KEY: misc_feature
<222> LOCATION: (1)..(3355)
<223> OTHER INFORMATION: r is a or g

<400> SEQUENCE: 166
ccaactcctt caaacttatt aacactttcc ttagttcaat atggggaagc ccttcttcac 60
tctctctctt tcttcccttt gcttgctact cttgtcgagt gcatgctttg ctattacctc 120
cagcaagttc aacgagtgcc aactcaacaa cctcaacgcg ttggaacccg accaccgcgt 180
tgagtccgaa ggtggtctta ttgaaacatg gaactctcaa caccctgagc tgcaatgcgc 240
cggtgtcact gtttccaaac gcaccctcaa ccgcaacggc ctccacttgc catcttactc 300
accttatccc caaatgatca ttgtcgttca aggtgcgtaa tattagtaag aagtatttat 360
cagcttaacg tgataacaat aatagtaata tgaaatattt attaaatttt ttataattaa 420
tctctgctag aaaatttgat taatcatttt tagtagaatt tgtttttctc aactaggttt 480
taaacaccac attatggcat agtatcatct aataaaacta ataataataa taataataat 540
aatactatat atctatatgt ctaatcacaa tttgatgact aactatctta caagttatat 600
gaatgaactc ttaacaatta tgatgactaa agagtgttaa ttagttgata attaatgtga 660
ttgttttgct tgatgatgat tgatgcacag ggaagggagc aattggattt gcatttccgg 720
gatgtcctga gacgtttgag aagccacaac arcaatcaag cagaagaggc tcaaggtcgc 780
agcagcaact acaagacagt caccagaaga ttcgtcactt caatgaagga gacgtactag 840
tgattcctcc tggtgttcct tactggacct ataacactgg cgatgaacca gttgttgcca 900
tcagtcttct tgacacctcc aacttcaaca atcagcttga tcaaaacccc agagtacgta 960
attataatga gcagtgatac acatgtcact gcatagtatc atacacactt aaaaagacac 1020
ctaacaaaat atttttattt attattttct tttattaaat atactaagta ataaaataat 1080
taatatactt tatatcacat catttggatg ttatgtttta ttatttatga aaaatgtttg 1140
aagaacacta tcttatatct agagggagaa atgaaaaaga aaaaaataca tataaatagg 1200
atagaattta taatgtgata agaaaagaga aataagttat attaatggag tgtttaaaat 1260
agttggatat atacttgtat catgattgga tatcaattga acttcattta ctattaacta 1320
ttattttatt attaaaaaaa acatgttctc ctcacatgtt aattttttta attactttca 1380
aggtatttta ccttgctggg aacccagata tagagcaccc agagaccatg caacaacagc 1440
agcagcagaa gagtcatggt ggacgcaagc aggggcaaca ccagcagcag gaggaagaag 1500
gtggcagtgt gctcagtggc ttcagcaaac atttcttagc acaatccttc aacaccaacg 1560
aggacacagc tgagaaactt cggtctccag atgacgaaag gaagcagatc gtgacagtgg 1620
agggaggcct cagcgttatc agccccaagt ggcaagaaca agaagacgaa gacgaagatg 1680
aagacgaaga atatgaacaa actccctctt atcctccacg acgaccaagc catggaaagc 1740
atgaagatga cgaggacgag gacgaagaag aagatcaacc tcgtcctgat caccctccac 1800
agcgaccaag caggcccgaa caacaagaac cacgtggaag aggatgtcag actagaaatg 1860
gggttgagga aaatatttgc accatgaagc ttcacgagaa cattgctcgc ccttcacgtg 1920
ctgacttcta caacccaaaa gctggtcgca ttagcaccct caacagtctc accctcccag 1980
ccctccgcca attcggactc agtgcccaat atgttgtcct ctacagggta tgtaattcac 2040
ttcattcata ttacaagtaa tcaacatgaa actaatatac gtgcatactt gcacatctac 2100
catagtagtg tttttgtgga ttttcagtgt taattagtgt atcttcagag aaagaaataa 2160
aagaaagcac taaaagaggg ggaaaatcat aattcatagg tcatatacga tacaataaga 2220
agacataaaa atgttaacaa gtatgttgta gggttgggtt ccttttaatg tcatttaaat 2280
taaatctcac tttgatagat aactgatttt tagaggttat gtagaggtaa ttttatagtt 2340
ataatggagt aaaattgttt gtattctaaa tttgtgcatt gattttttaa agtgagtttc 2400
gacatataat ttaaaatata tcattacctc ttatttgata ataattaaac atttatcatt 2460
tatataataa taataataat atgtaacatg tattattata tccatgcatg cagaatggaa 2520
tttactctcc acattggaac ttgaacgcga acagtgtgat ctatgtgact cgagggaagg 2580
aagagttaga gtggtgaact gccaagggaa tgcagtgttc gacggtgagc taaggagggg 2640
acaattgcta gtggtgccgc agaactttgt ggtggctgag caagggggag aacaaggatt 2700
ggaatacgta gtgttcaaga cacaccacaa cgccgtgagc agctacatta aggatgtgtt 2760
tagggcaatc ccttcggagg ttctttccaa ttcttacaac cttggccaga gtcaagtgcg 2820
tcagctcaag tatcaaggaa actccggccc tttggtcaac ccataaataa caacaagcat 2880
atatgaaggt gtggtgaggc catcttatat gaaataatat caaaatatat tttgtgtaat 2940
aataaaacta tggcctatgt atttaccacc ctccgaccca gcctatgtta atatctgagt 3000
ggcgttgtac ctttgaatcg ccttaataaa atgtcagtct taaaaaaaaa aaaaattttc 3060
tgtcttccat cgctcaagtt gtgtgcttta attgcttata actcgagatg tctgtctatt 3120
aacgaaaatc aatattaaca actgaacttc tgctcccatt aaaggttgaa aaaaaatgct 3180
tttattgtgt aattaatttt atatataagt aactttttta agtaatcaaa ttaatgatta 3240
tataaattaa tctttttaag taagatacaa atttgatatt ttattaattg aatttgaatt 3300
tattacgata gaagttatga ttataatagt aattaaatta attattataa aatta 3355

<210> SEQ ID NO 167
<211> LENGTH: 1011
<212> TYPE: DNA
<213> ORGANISM: Glycine max

<400> SEQUENCE: 167
gtacttcctt tattcctgac gtttttatat caagtggaca tacgtgaaga ttttaattat 60
cagtctaaat atttcattag cacttaatac ttttctgttt tattcctatc ctataagtag 120
tcccgattct cccaacattg cttattcaca caactaacta agaaagtctt ccatagcccc 180
ccaaaaatga agagcaccat cttctttgct ctctttctct tttgtgcctt caccacctca 240
tacctacctt cagccatcgc tgatttcgtg ctcgataatg aaggtaaccc tcttgaaaat 300
ggtggcacat attatatctt gtcagacata acagcatttg gtggaataag agcagcccca 360
acgggaaatg aaagatgccc tctcactgtg gtgcaatctc gcaatgagct cgacaaaggg 420
attggaacaa tcatctcgtc cccatatcga atccgtttta tcgccgaagg ccatcctttg 480
agccttaagt tcgattcatt tgcagttata atgctgtgtg ttggaattcc taccgagtgg 540
tctgttgtgg aggatctacc agaaggacct gctgttaaaa ttggtgagaa caaagatgca 600
atggatggtt ggtttagact tgagagagtt tctgatgatg aattcaataa ctataagctt 660
gtgttctgtc cacagcaagc tgaggatgac aaatgtgggg atattgggat tagtattgat 720
catgatgatg gaaccaggcg tttggtggtg tctaagaaca aaccgttagt ggttcagttt 780
caaaaacttg ataaagaatc actggccaag aaaaatcatg gcctttctcg cagtgagtga 840
gacacaagtg tgagagtact aaataaatgc tttggttgta cgaaatcatt acactaaata 900
aaataatcaa agcttatata tgccttccgc taaggccgaa tgcaaagaaa ttggttcttt 960
ctcgttatct tttgccactt ttactagtac gtattaatta ctacttaatc a 1011

<210> SEQ ID NO 168
<211> LENGTH: 25
<212> TYPE: DNA
<213> ORGANISM: Artificial Sequence
<220> FEATURE:
<223> OTHER INFORMATION: Synthetic Primer

<400> SEQUENCE: 168
gagaacaaag atgcaatgga tggtt 25

<210> SEQ ID NO 169
<211> LENGTH: 25
<212> TYPE: DNA
<213> ORGANISM: Artificial Sequence
<220> FEATURE:
<223> OTHER INFORMATION: Synthetic Primer

<400> SEQUENCE: 169
gctgtggaca gaacacaagc ttata 25

<210> SEQ ID NO 170
<211> LENGTH: 18
<212> TYPE: DNA
<213> ORGANISM: Artificial Sequence
<220> FEATURE:
<223> OTHER INFORMATION: Synthetic Primer

<400> SEQUENCE: 170
agaaactctc tcaagtct 18

<210> SEQ ID NO 171
<211> LENGTH: 19
<212> TYPE: DNA
<213> ORGANISM: Artificial Sequence
<220> FEATURE:
<223> OTHER INFORMATION: Synthetic Primer

<400> SEQUENCE: 171
catcagaaac tctaagtct 19

<210> SEQ ID NO 172
<211> LENGTH: 77
<212> TYPE: DNA
<213> ORGANISM: Glycine max
<220> FEATURE:
<221> NAME/KEY: misc_feature
<222> LOCATION: (41)..(41)
<223> OTHER INFORMATION: k is g or t

<400> SEQUENCE: 172
gtgagaacaa agatgcaatg gatggttggt ttagacttga kagagtttct gatgatgaat 60
tcaataacta taaggct 77

<210> SEQ ID NO 173
<211> LENGTH: 75
<212> TYPE: DNA
<213> ORGANISM: Glycine max

<400> SEQUENCE: 173
gtgagaacaa agatgcaatg gatggttggt ttagacttta gagtttctga tgatgaattc 60

-continued

```
aataactata aggct                                                       75


<210> SEQ ID NO 174
<211> LENGTH: 77
<212> TYPE: DNA
<213> ORGANISM: Glycine max

<400> SEQUENCE: 174

gtgagaacaa agatgcaatg gatggttggt ttagacttga gagagtttct gatgatgaat     60

tcaataacta taaggct                                                     77


<210> SEQ ID NO 175
<211> LENGTH: 34
<212> TYPE: DNA
<213> ORGANISM: Glycine max

<400> SEQUENCE: 175

gtgagaacaa agatgcaatg gatggttggt ttag                                  34


<210> SEQ ID NO 176
<211> LENGTH: 30
<212> TYPE: DNA
<213> ORGANISM: Glycine max

<400> SEQUENCE: 176

gtgagaacaa agatgcaatg gatggttggt                                       30


<210> SEQ ID NO 177
<211> LENGTH: 29
<212> TYPE: DNA
<213> ORGANISM: Glycine max

<400> SEQUENCE: 177

gtgagaacaa agatgcaatg gatggttgg                                        29
```

AGRONOMICALLY ELITE SOYBEANS WITH HIGH β-CONGLYCININ CONTENT

This application is a divisional of U.S. application Ser. No. 11/517,186, filed Sep. 7, 2006, which claims the benefit of priority of U.S. Provisional Application Ser. No. 60/714,779, field Sep. 7, 2005, and U.S. Provisional Application Ser. No. 60/722,493, filed Sep. 30, 2005; each of the entire disclosures of which are incorporated herein by reference in their entireties.

INCORPORATION BY REFERENCE OF SEQUENCE LISTING SUBMITTED ON A COMPACT DISC

The Sequence Listing is submitted on one compact disc (Copy 1), together with a duplicate thereof (Copy 2), each created on Sep. 7, 2006, and each containing one—79 kb file entitled "MSUT015US.APP.TXT." The material contained on the compact disc is specifically incorporated herein by reference.

BACKGROUND OF THE INVENTION

1. Field of the Invention

The present invention relates generally to the field of plant breeding and molecular biology. In particular, the invention relates to agronomically elite soybean varieties with increased beta-conglycinin content and materials for making such plants.

2. Description of Related Art

Glycinin and β-Conglycinin are two major storage proteins in soybeans, accounting for approximately 70% of total proteins or 40% of total seed weight. The glycinin (11s globulin) is composed of five different subunits, designated A1aB2, A2B1a, A1bB1b, A5A4B3, A3B4, respectively. Each subunit is composed of two polypeptides, one acidic and one basic, covalently linked through a disulfide bond. The two polypeptide chains result from post-translational cleavage of proglycinin precursors, a step that occurs after the precursor enters the protein bodies (Chrispeels et al., 1982). Five major genes have been identified to encode these polypeptide subunits. They are designated as Gy1, Gy2, Gy3, Gy4 and Gy5, respectively (Nielsen et al., 1997). In addition, a pseudogene, gy6, and minor gene, Gy7, were also reported (Beilinson et al., 2002). Genetic mapping of these genes has been reported by various groups (Diers et al., 1993, Chen and Shoemaker 1998, Beilinson et al., 2002). Gy1 and Gy2 were located 3 kb apart and mapped to linkage group N (Nielsen et al., 1989), Gy3 was mapped to linkage group L (Beilinson et al., 2002). Gy4 and Gy5 were mapped to linkage groups O and F, respectively. All of these genes were mapped using RFLP probes on Southern Blots.

β-conglycinin, on the other hand, is composed of α (~67 kda), α' (~71 kDa) and β (~50 kDa) subunits and each subunit is processed by co- and post-translational modifications (Ladin et al., 1987; Utsumi, 1992). The β-conglycinin subunits are encoded by the genes Cgy1, Cgy2 and Cgy3, respectively. Genetic analysis indicated that Cgy2 is tightly linked to Cgy3, whereas Cgy1 segregates independently of the other two. The β-conglycinin gene family contains at least 15 members divided into two major groups, which encode the 2.5 kb and 1.7 kb embryo mRNA, respectively (Harada et al., 1989).

Soybean plants with increased β-conglycinin levels and decreased glycinin levels would provide substantial benefit. One reason for this is that β-conglycinin is a soluble protein whereas glycinin is much less soluble. It has also been found that β-conglycinin, especially the α' subunit, has significantly higher nutritional value and a positive impact on human health as compared to glycinin (Baba et al., 2004). A number of experiments using animal models have indicated that α' subunit from soybean β-conglycinin could lower plasma triglycerides, and also increase LDL ("bad" cholesterol) removal from blood (Duranti et al., 2004, Moriyama et al., 2004, Adams et al., 2004, Nishi et al., 2003). Therefore, soybean varieties with an increased β-conglycinin content will have higher value than traditional varieties and will be suitable for use in nutrition drinks and other food products.

Interestingly, mutations in the glycinin genes have a direct impact on β-conglycinin content in soybean seeds. Mutant soybean plants with decreased glycinin content have increased β-conglycinin content. However, since multiple glycinin alleles are involved in glycinin subunit production, breeding plants with reduced expression from multiple Gy subunits has proved difficult since such plants have other attributes, such as low yield, excessive lodging and green seed that render them commercially nonviable. Previous methods for determining the inheritance of mutations resulting in decreased glycinin content did not enable high-throughput techniques required to select for these phenotypes while introducing agronomically superior characteristics. For example, previous assessment of Gy inheritance was dependent upon analysis of protein expression, which is costly, labor intensive and cannot track the inheritance of recessive mutations. The possibility of producing such plants regardless of labor was also unknown, due to additional complications such as linkage drag and epistasis associated with attempts to introgress a mutant Gy allele. The combination of alleles are also unpredictable with respect to the phenotype obtained. Thus, there is a long-standing but unfilled need in the art for agronomically elite soybean plants with reduced expression of multiple Gy protein subunits and methods for production of such plants.

Lipoxygenases are enzymes that catalyze the dioxygenation of polyunsaturated fatty acids. Soybean seeds contain three lipoxygenase isozymes—lipoxygenases 1, 2, and 3. These isozymes contribute to the production of unpleasant flavors in soybean seeds. The unpleasant flavors are absent or less pronounced in seeds deficient in these isozymes, particularly those lacking lipoxygenase-2. Accordingly, soybean seeds lacking one or more lipoxygenase isozymes are desirable for use in making drink and food products. Genetic studies of Lipoxygenase 1, 2, and 3 deficient lines demonstrated that the absence of each was due to single recessive alleles—lx1, lx2, and lx3, respectively. The loci defined by lx1 and lx2 are closely linked and are not genetically linked to lx3 (Kitamura, 1984; Kitamura et al, 1985; Hajika et al., 1992; Hildebrand et al., 1982). The structural genes encoding Lipoxygenases 1, 2, and 3 have been cloned and designated Lox1, Lox2, and Lox3, respectively (Shibata et al., 1987; Shibata et al., 1988; Yenofsky et al., 1988).

Kunitz Trypsin inhibitor (KTI) is an antinutritional and allergenic factor in soybeans that interferes with digestion and absorption of proteins when present in a diet. Thus, soybean varieties with a KTI-null mutant trait have a higher commercial value than traditional varieties. Genetic and biochemical studies of KTI production in soybean lines have been carried out (e.g. de Moraes et al., 2006; Natarajan et al., 2006), and three related genes have been identified, with KTI3 encoding the predominant Kunitz Trypsin Inhibitor Protein in cultivated soybean genotypes (Natarajan et al., 2006). Some specific DNA markers associated with loss of KTI production in certain soybean lines have been reported (de Moraes et al., 2006).

SUMMARY OF THE INVENTION

The current invention provides, in one embodiment, a plant of an agronomically elite soybean variety with an increased seed β-conglycinin content, comprising non-transgenic mutations providing a null phenotype of at least two of the glycinin subunits selected from the group consisting of Gy1, Gy2, Gy3, Gy4, and Gy5. An increased seed β-conglycinin content may be measured, for example, with respect to a plant of the same genotype as said plant but lacking the mutations. In specific embodiments, the non-transgenic mutations may confer a Gy2, and Gy4 null phenotype and increased seed β-conglycinin content. Thus, the plants of the current invention comprise, in one aspect, seeds with low glycinin content and high β-conglycinin content. In certain embodiments, the seed β-conglycinin content for plants of the invention is about or at least about 34, 35, 36, 37, 38, 39, 40, 41, 42, 43, 44, 45, 46, 47, 48, 49, 50 percent or more of the total protein content. In some embodiments, a plant of the invention has a seed glycinin content of about or less than about 15, 14, 13, 12, 11, 10, 9, 8, 7, 6, 5, 4, 3, 2, 1, or 0 percent of the total protein. In some cases, plants of the invention may comprise a mutant Gy4 allele. For example, a mutant Gy4 allele may comprise a point mutation at nucleotide 682, such that the translation initiation codon is abrogated. In still further embodiments, plants provided by the invention may comprise Gy1 and Gy2 null alleles. In one embodiment of the invention, one or more of any of the Gy1, Gy2, Gy3 and/or Gy4 alleles may be the same as the null alleles in line B2G2, a representative sample of seeds of which have been deposited under ATCC Accession No. PTA-6893.

In certain embodiments of the invention, soybean plants are provided that further comprise a mutation that confers reduced levels of Gy1/Gy3 protein. As used herein "reduced levels of Gy1/Gy3 protein" means seed from plants comprising the non-transgenic mutation have reduced Gy1/Gy3 protein levels as compared to plants with an identical genetic background that lack the mutation. For example plants comprising a non-transgenic mutation that confers reduced Gy1/Gy3 may have a Gy1/Gy3 protein content of less than about 3.1% of total seed protein. In certain cases, the mutation conferring reduced Gy1/Gy3 protein content may be a non-transgenic mutation. In some aspects of the invention, a plant of the invention comprises a mutant Gy1 allele. For example, the mutant Gy1 allele may comprise a deletion spanning the upstream promoter region, exon I and intron I.

In certain embodiments, a plant of the invention may further comprise mutations conferring reduced Gy5 protein levels. In certain cases, the mutation conferring reduced Gy5 protein content is a non-transgenic mutation. Thus in some aspects, plants of the invention comprise mutations conferring reduced Gy1, Gy2, Gy3, Gy4 and Gy5 protein levels. In certain aspects, plants of the invention may comprise non-transgenic mutations conferring a decreased Gy1, Gy2 Gy3, Gy4, and Gy5 phenotype. The seed of these plants may have a glycinin content of about or less than about 15, 14, 13, 12, 11, 10, 9, 8, 7, 6, 5, 4, 3, 2, 1, or 0 percent of the total protein. Thus plants of the invention comprising a decreased Gy1, Gy2, Gy3, Gy4 and Gy5 phenotype may comprise seed with a β-conglycinin content of about or at least about 34, 35, 36, 37, 38, 39, 40, 41, 42, 43, 44, 45, 46, 47, 48, 49, 50 percent or greater of the total protein content.

In certain embodiments, a plant of the invention may further comprise mutations conferring a lx1, lx2, and/or lx3 phenotype. In certain cases, the mutation conferring the lx1, lx2, and/or lx3 phenotype is a non-transgenic mutation. Thus in some aspects, plants of the invention comprise mutations conferring a reduced Gy2 and Gy4 phenotype and mutations conferring of one or more of a lx1, lx2, and/or lx3 phenotype. In one embodiment of the invention, such plants may further comprise mutations conferring a reduced Gy1, Gy3, and Gy5 phenotype.

Plant parts are also provided by the invention. Parts of a plant of the invention include, but are not limited to, pollen, ovules, meristems, cells, and seed. Cells of the invention may further comprise, regenerable cells, such as embryos meristematic cells, pollen, leaves, roots, root tips, and flowers. Thus, these cells could be used to regenerate plants of the invention.

Also provided herein are parts of the seeds of a plant according to the invention. Thus, crushed seed, and meal or flour made from seed according to the invention is also provided as part of the invention. The invention further comprises, a method for making soy meal or flour comprising crushing or grinding seed according to the invention. Such soy flour or meal according to the invention may comprise genomic material of plants of the invention. In one embodiment, the food may be defined as comprising the genome of such a plant. In further embodiments soy meal or flour of the invention may be defined as comprising increased β-conglycinin and decreased glycinin content, as compared to meal or flour made from seeds of a plant with an identical genetic background, but not comprising the non-transgenic, mutant Gy2 and Gy4 null phenotype.

In yet a further aspect of the invention there is provided a method for producing a soybean seed, comprising crossing the plant of the invention with itself or with a second soybean plant. Thus, this method may comprise preparing a hybrid soybean seed by crossing a plant of the invention with a second, distinct, soybean plant.

Still yet another aspect of the invention is a method of producing a food product for human or animal consumption comprising: (a) obtaining a plant of the invention; (b) cultivating the plant to maturity; and (c) preparing a food product from the plant. In certain embodiments of the invention, the food product may be protein concentrate, protein isolate, meal, oil, flour or soybean hulls. In some embodiments, the food product may comprise beverages such as soymilk and other nutritional beverages, infused foods, sauces, condiments, salad dressings, fruit juices, syrups, desserts, icings and fillings, soft frozen products, confections or intermediate foods. Foods produced from the plants of the invention may comprise increased β-conglycinin content and thus be of greater nutritional value foods made with typical soybean varieties. Additionally, plants of the invention comprising decreased glycinin content may be used in food compositions requiring low amounts of insoluble protein.

In further embodiments, a plant of the invention may further comprise a transgene. For example, a plant may comprise transgenes conferring herbicide tolerance, disease resistance, insect and pest resistance, altered fatty acid, protein or carbohydrate metabolism, increased grain yield, altered plant maturity and/or altered morphological characteristics. For example, a herbicide tolerance transgene may comprise a glyphosate resistance gene.

In certain embodiments, a plant of the invention may be defined as prepared by a method wherein a plant comprising non-transgenic mutations conferring a Gy2 and Gy4 null phenotype and increased β-conglycinin content is crossed with a plant comprising agronomically elite characteristics. The progeny of this cross may be assayed for agronomically elite characteristics and Gy2 and Gy4 protein content, and progeny plants selected based on these characteristics, thereby generating the plant of the invention. Thus in certain embodiments, a plant of the invention may be produced by crossing a selected starting variety with a second soybean plant comprising agronomically elite characteristics. In some embodiments, a plant of the invention may be defined as prepared by a method wherein a plant comprising a non-transgenic mutation conferring a lx1, lx2, and/or lx3 phenotype is crossed with a plant comprising reduced Gy2 and Gy4 protein content, and increased β-conglycinin content.

The current invention also provides a method of plant breeding wherein a plant is assayed for the presence of a polymorphism in a soybean plant genomic region associated with Gy1/Gy2, Gy3, and Gy4 alleles, comprising selecting the plant and crossing the plant with a second soybean plant to produce progeny. In some embodiments, the method of the invention may comprise selecting a progeny plant by assaying the plant for a polymorphism associated with a decreased Gy2 or Gy4 phenotype and crossing the plant with a second soybean plant to produce further progeny plants. In certain embodiments of the invention, the second soybean plant may comprise agronomically elite characteristics. The method of the invention may also further comprise selecting a soybean plant comprising the polymorphism and agronomically elite characteristics. Thus, the invention enables the introduction of non-transgenic mutations conferring a Gy1/Gy3 and/or Gy2 and Gy4 phenotype and increased seed β-conglycinin content into agronomically elite soybean plants. A method of the invention may be repeated 1, 2, 3, 4, 5, 10, 15, 20, or more times as desired to select agronomically elite progeny with polymorphisms indicative of non-transgenic mutations at Gy1/Gy2 and/or Gy3 and/or Gy4 alleles at each step. In certain embodiments of invention, the first soybean plant may be a plant of line B2G2, a representative sample of seed of which have been deposited under ATCC Accession No. PTA-6893. In a further embodiment, a method of the invention may further comprise selecting a plant comprising polymorphisms indicative of a non-transgenic mutation in Gy1/Gy2, Gy3, and Gy4 alleles.

In some embodiments, a method of the invention may further comprise selecting plants with markers indicative of reduced Gy1/Gy3 and/or Gy5 content. Thus, methods of marker assisted plant breeding according to the invention may be used to breed soybeans that have reduced Gy1, Gy2, Gy3, Gy4, and Gy5 content.

In some embodiments of the current invention, non-transgenic mutations conferring a decreased Gy1, Gy2, Gy3, or Gy4 phenotype may comprise mutations in Gy1, Gy2, Gy3, or Gy4 alleles. In certain embodiments, the mutant Gy alleles are detected using genetic markers comprising polymorphisms within 50 cM of a Gy allele. In further, aspects of the invention, plants with a decreased Gy1/Gy2 phenotype comprise a mutant Gy1 allele. In some cases, the mutant Gy1 allele comprises a deletion, such as a deletion of the promoter region, exon I and intron I. In other embodiments, mutant Gy1 alleles can be detected using markers NS0199002 or NS0199008. In certain aspects of the invention, mutant Gy1 alleles may be detected with markers of Gy2, since the two genes are closely linked. Thus, in other aspects of the invention, mutant Gy2 alleles may be detected with markers to Gy1. In certain embodiments of the invention, phenotypically Gy4 null plants comprise mutant Gy4 alleles. In further embodiments, mutant Gy4 alleles comprise point mutations such as an SNP that abrogates the translation initiation codon. In additional aspects of the invention, the Gy4 null allele may be detected with the NS0199003 marker. SNP markers may be detected, for example using fluorescently labeled oligonucleotides.

In some embodiments, a method of the invention may further comprise selecting plants with markers indicative of reduced lipoxygenase 1, 2, and/or 3 content. Thus, methods of marker assisted plant breeding according to the invention may be used to produce soybeans that have reduced lipoxygenase 1, 2, and/or 3 content.

In particular embodiments of the invention, non-transgenic mutations conferring a lx1, lx2, and/or lx3 phenotype may comprise mutations in Lox1, Lox2, and/or Lox3 alleles. In one embodiment of the invention, the mutant alleles conferring a lx1, lx2, and/or lx3 phenotype are detected using genetic markers comprising polymorphisms within 50 cM of a Lox allele. In certain embodiments, lx1 alleles are detected using one or more of INDEL 178-180, SNP 326, SNP 363, SNP 380, SNP 713, SNP 1196, SNP 1253, SNP 1372, SNP 1388, SNPR 1527, SNP 1554, SNP 2267, SNP 3088, SNP 3125, SNP 3139, INDEL 3832-3905, SNP 4043, SNP 4057, SNP 4193, SNP 4225, SNP 4247, SNP 4267, or SNP 4439 as shown below in Table 14. In some embodiments, lx2 alleles can be detected using one or more of SNP 323, SNP 439, SNP 1390, SNP 1431, SNP 1458, INDEL 2486-87, or SNP 2542 as shown below in Table 15. SNP 2542 is also referred to as the NS0203296 marker.

In some embodiments, a method of the invention may further comprise selecting plants with markers indicative of a KTI-null or KTI-reduced trait. Thus, methods of marker assisted plant breeding according to the invention may be used to produce soybeans that have reduced or undetectable Kunitz Trypsin Inhibitor content.

In certain embodiments of the invention, mutations conferring a KTI-null phenotype may comprise mutations in a gene encoding KTI. In a particular embodiment, mutations conferring a KTI-null phenotype comprise mutations in the KTI3 gene, also termed "KTIA". In one embodiment of the invention, the mutant alleles conferring a KTI-null phenotype are detected using genetic markers comprising polymorphisms within 50 cM of a KTI allele. In certain embodiments, KTI alleles are detected using one or more INDELs or SNPs located within the KTI3 gene, for instance as shown below in Table 18. Such selection may thus be based on marker information (plant genotype) rather than on enzymatic analysis of Trypsin activity or analysis of KTI content.

Embodiments discussed in the context of a method and/or composition of the invention may be employed with respect to any other method or composition described herein. Thus, an embodiment pertaining to one method or composition may be applied to other methods and compositions of the invention as well.

As used in the specification or claims, "a" or "an" may mean one or more. As used herein in the claim(s), when used in conjunction with the word "comprising", the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

As shown in FIG. 8, this marker allowed a clear distinction between the "A" allele from the lx2 mutant and the "T" allele from wild type as described in Example 13 and Table 15.

DESCRIPTION OF ILLUSTRATIVE EMBODIMENTS

The present invention provides plants and methods for producing plants comprising non-transgenic mutations that confer a Gy2 and Gy4 null phenotype and agronomically elite characteristics. These mutations confer low glycinin and high β-conglycinin content to seed of mutant plants. Thus, plants of the invention will be of great value as β-conglycinin provides improved nutritional characteristics and solubility as compared to glycinin. Additionally, plants provided herein comprise agronomically elite characteristics, enabling a commercially significant yield of high β-conglycinin, low glycinin, soybeans. In certain aspects of the invention, plants with increased β-conglycinin contents comprise non-transgenic null alleles for Gy2 and/or Gy4 and therefore have the additional advantage of reduced governmental regulation as compared to soybean varieties containing corresponding transgenic alleles at these loci. Also provided are plants that further comprise non-transgenic Gy1 and Gy3 null alleles and also provide such benefits.

The invention also provides plants and methods for producing plants comprising non-transgenic mutations that confer a lipoxygenase-2 null phenotype. The combination of a lipoxygenase-2 null and glycinin null phenotype provides an increased content of the highly functional and healthful β-conglycinin protein. β-conglycinin in particular contains bioactive peptides that are responsible for cholesterol-lowering and weight management (through satiety effects and reduction in fat deposits) benefits.

Another valuable combination in accordance with the invention is a lipoxygenase-2 null and mid-oleic content (e.g., 40-65% oleic). This soybean will produce low levels of off-flavors because it lacks the main catalyst of lipid oxidation (lipoxygenase-2) and has much lower levels of the substrate (linoleic acid). In addition, such soybeans will have an improved (lower) ratio of omega-6 to omega-3 fatty acids, a benefit for cardiovascular health.

Figure 4:
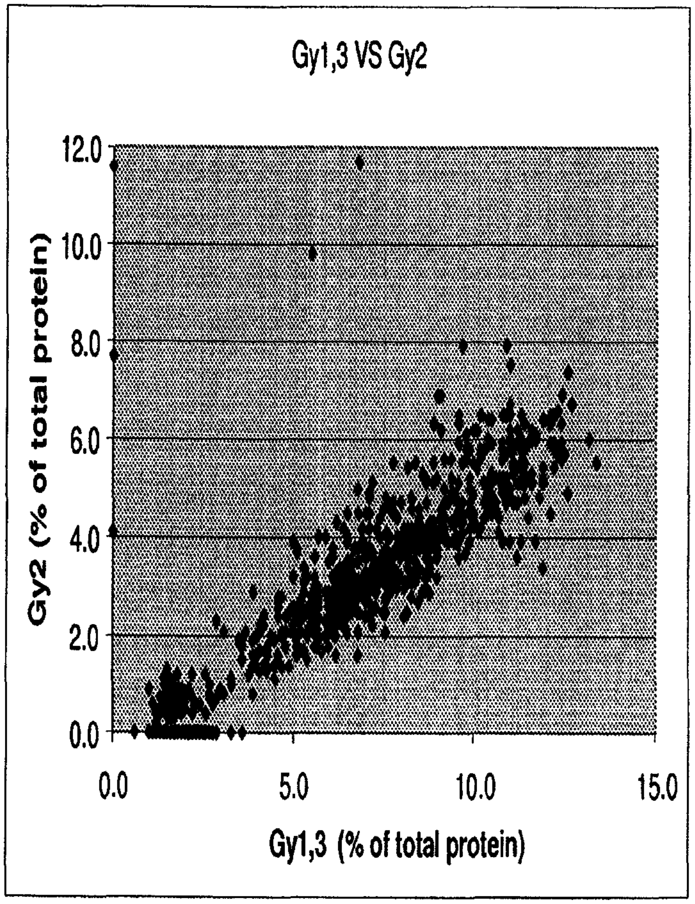
FIG. 4: The amount of Gy2 encoded protein is positively correlated with the amount of Gy1 and Gy3 encoded protein. Panel A. Graph plots the observed amount of Gy1 and Gy3 encoded acidic protein (x axis) versus the amount of Gy2 encoded protein (y axis). Panel B. Table shows correlation coefficients between the expression levels of the Gy1, Gy2, Gy3, Gy4 and Gy5 encoded proteins.

Also provided herein is a method for breeding soybean plants that comprise non-transgenic mutations conferring a decreased Gy1, Gy2, Gy3 and Gy4 phenotype and agronomically elite characteristics. Studies detailed below identify polymorphisms that can be used to identify plants with decreased Gy1, Gy2, Gy3 and Gy4 protein content. Three of the markers identified herein, NS0199002, NS0199003, and NS0199008, can be used to accurately predict a decreased Gy1, Gy2, Gy3, and Gy4 phenotype of soybean plants. As demonstrated below, the inheritance of Gy1 and Gy2 is genetically linked, thus markers to either Gy1 (NS0199008) or Gy2 (NS0199002) may be used to track the inheritance of the decreased Gy1 and Gy2 phenotype. Additionally, as shown in FIG. 4 the reduced Gy1,3 phenotype closely correlates with a decreased Gy2 phenotype. It is also shown that markers can be used to identify plants that are phenotypically null for Gy4 encoded proteins. For example, the NS0199003 marker was used in studies to accurately determine the Gy4 phenotype of soybean plants. Thus, by use of a Gy1,2,3 marker in combination with a Gy4 genetic marker the invention enables the high throughput screening and marker assisted breeding of plants with non-transgenic mutations conferring a decreased Gy1, Gy2, Gy3 and Gy4 phenotype, and high seed β-conglycinin content. Sequencing studies were also undertaken herein that have identified markers that may be used to determine the inheritance of the decreased Gy5 phenotype and to directly select for a decreased Gy2 phenotype.

Also provided is a method for breeding soybean plants comprising non-transgenic mutations conferring a decreased lipoxygenase-2 phenotype. For example, studies described below identified sequence variations associated with the lipoxygenase-2 null (lx2) phenotype in soybeans. Molecular markers have been developed out of these sequence variations for the lx2 phenotypes. Using these markers associated with lipoxygenase-2 null trait, breeders can make selections based on marker information, or genotypes, rather than on lipoxygenase analysis by SDS-PAGE. Marker data is more cost effective, faster and reliable, enabling one to test greater numbers and identify elite lines with multiple traits (e.g. Lipoxygenase-2 null and glycinin-null).

I. PLANTS OF THE INVENTION

The invention provides, for the first time, plants and derivatives thereof of soybean varieties that combine non-transgenic mutations conferring a Gy2, and Gy4 null phenotype and increased β-conglycinin content with an agronomically elite phenotype. In some embodiments such plants may further comprise non-transgenic Gy1 and Gy2 null alleles. Such plants may be defined as having a commercially significant yield, for example, that is defined as a yield of at least 103% of the check lines AG2703 and DKB23-51. In certain further embodiments, plants are provided comprising the non-transgenic Gy1-4 mutant alleles and increased beta-conglycinin content and a grain yield of at least about 90%, 94%, 98%, 100%, 105% or about 110% of these lines. Such plants may be defined, in certain embodiments of the invention, as having a yield a yield in excess of about 35, 37, 39, 41, 43 or 45 bushels per acre over at least 10 environments. In certain embodiments, the β-conglycinin content of the seeds of plants of the invention may be greater than about 34%, 35%, 36%, 37%, 38%, 39%, 40%, 41%, 42%, 43%, 44%, 45%, 46%, 47%, 48%, 49%, or even 50% or any range derivable therein. In certain embodiments, the plants of the invention may further comprise mutations conferring a lx1, lx2, and/or lx3 phenotype.

One aspect of the current invention is therefore directed to the aforementioned plants and parts thereof and methods for using these plants and plant parts. Plant parts include, but are not limited to, pollen, an ovule and a cell. The invention further provides tissue cultures of regenerable cells of these plants, which cultures regenerate soybean plants capable of expressing all the physiological and morphological characteristics of the starting variety. Such regenerable cells may include embryos, meristematic cells, pollen, leaves, roots, root tips or flowers, or protoplasts or callus derived therefrom. Also provided by the invention are soybean plants regenerated from such a tissue culture, wherein the plants are capable of expressing all the physiological and morphological characteristics of the starting plant variety from which the regenerable cells were obtained.

II. MARKER ASSISTED SELECTION FOR PRODUCTION OF SOYBEAN VARIETIES WITH NON-TRANSGENIC MUTANT GY ALLELES AND AN AGRONOMICALLY ELITE PHENOTYPE

The current invention provides genetic markers and methods for the introduction of non-transgenic, mutant Gy alleles into agronomically elite soybean plants. The invention therefore allows, for the first time, the creation of plants that combine these mutant Gy alleles that confer high seed β-conglycinin content with a commercially significant yield and an agronomically elite genetic background. Using the methods of the invention, loci conferring the "11S null" phenotype may be introduced into a desired soybean genetic background, for example, in the production of new varieties with commercially significant yield and high seed β-conglycinin content.

Marker assisted introgression involves the transfer of a chromosome region defined by one or more markers from one germplasm to a second germplasm. The initial step in that process is the localization of the trait by gene mapping, which is the process of determining the position of a gene relative to other genes and genetic markers through linkage analysis. The basic principle for linkage mapping is that the closer together two genes are on the chromosome, the more likely they are to be inherited together. Briefly, a cross is generally made between two genetically compatible but divergent parents relative to traits under study. Genetic markers can then be used to follow the segregation of traits under study in the progeny from the cross, often a backcross (BC1), $F_2$, or recombinant inbred population.

The term quantitative trait loci, or QTL, is used to describe regions of a genome showing quantitative or additive effects upon a phenotype. The Gy loci represent exemplary QTL since multiple mutant Gy alleles result in increasing reduction in total seed glycinin content and important concomitant increases in β-conglycinin content. Herein identified are genetic markers for non-transgenic, mutant Gy alleles that enable breeding of soybean plants comprising the non-transgenic, mutant Gy alleles with agronomically superior plants, and selection of progeny that inherited the mutant Gy alleles. Thus, the invention allows the use of molecular tools to combine these QTLs with desired agronomic characteristics.

Also identified are genetic markers for non-transgenic, mutant lx1 and lx2 alleles that enable the breeding of soybean plants comprising one or both of the non-transgenic, mutant lx1 and lx2 alleles, and selection of progeny that inherited the mutant lx allele or alleles. Soybean plants having reduced lipoxygenase are useful in themselves and are useful in combination with other agronomic characteristics. For example, reduced lipoxygenase and reduced glycinin is a valuable trait combination. Another valuable combination is reduced lipoxygenase and mid-oleic content (e.g., 40-65% oleic). Thus, the invention allows the use of molecular tools to combine lx alleles with, for example, mutant Gy alleles in agronomically superior plants as described above.

A. Development and Use of Linked Genetic Markers

A sample first plant population may be genotyped for an inherited genetic marker to form a genotypic database. As used herein, an "inherited genetic marker" is an allele at a single locus. A locus is a position on a chromosome, and allele refers to conditions of genes; that is, different nucleotide sequences, at those loci. The marker allelic composition of each locus can be either homozygous or heterozygous. In order for information to be gained from a genetic marker in a cross, the marker must be polymorphic; that is, it must exist in different forms so that the chromosome carrying the mutant gene can be distinguished from the chromosome with the normal gene by the form of the marker it also carries.

Formation of a phenotypic database can be accomplished by making direct observations of one or more traits on progeny derived from artificial or natural self-pollination of a sample plant or by quantitatively assessing the combining ability of a sample plant. By way of example, a plant line may be crossed to, or by, one or more testers. Testers can be inbred lines, single, double, or multiple cross hybrids, or any other assemblage of plants produced or maintained by controlled or free mating, or any combination thereof. For some self-pollinating plants, direct evaluation without progeny testing is preferred.

The marker genotypes may be determined in the testcross generation and the marker loci mapped. To map a particular trait by the linkage approach, it is necessary to establish a positive correlation in inheritance of a specific chromosomal locus with the inheritance of the trait. In the case of complex inheritance, such as with quantitative traits, including specifically glycinin content and yield, linkage will generally be much more difficult to discern. In this case, statistical procedures may be needed to establish the correlation between phenotype and genotype. This may further necessitate examination of many offspring from a particular cross, as individual loci may have small contributions to an overall phenotype.

Coinheritance, or genetic linkage, of a particular trait and a marker suggests that they are physically close together on the chromosome. Linkage is determined by analyzing the pattern of inheritance of a gene and a marker in a cross. The unit of genetic map distance is the centimorgan (cM), which increases with increasing recombination. Two markers are one centimorgan apart if they recombine in meiosis about once in every 100 opportunities that they have to do so. The centimorgan is a genetic measure, not a physical one. Those markers located less then 50 cM from a second locus are said to be genetically linked, because they are not inherited independently of one another. Thus, the percent of recombination observed between the loci per generation will be less than 50%. In particular embodiments of the invention, a marker used may be defined as located less than about 45, 35, 25, 15, 10, 5, 4, 3, 2, or 1 or less cM apart from a locus. In certain embodiments of the invention, markers may be used for detecting polymorphisms within the contributing loci themselves and thus located at 0 cM respective to the loci, for example, comprising a mutation within a Gy1, Gy2, Gy3, Gy3, Gy4, or Gy5 coding sequence or regulatory element.

During meiosis, pairs of homologous chromosomes come together and exchange segments in a process called recombination. The further a marker is from a gene, the more chance there is that there will be recombination between the gene and the marker. In a linkage analysis, the coinheritance of marker and gene or trait are followed in a particular cross. The probability that their observed inheritance pattern could occur by chance alone, i.e., that they are completely unlinked, is calculated. The calculation is then repeated assuming a particular degree of linkage, and the ratio of the two probabilities (no linkage versus a specified degree of linkage) is determined. This ratio expresses the odds for (and against) that degree of linkage, and because the logarithm of the ratio is used, it is known as the logarithm of the odds, e.g. an lod score. A lod score equal to or greater than 3, for example, is taken to confirm that gene and marker are linked. This represents 1000:1 odds that the two loci are linked. Calculations of linkage is greatly facilitated by use of statistical analysis employing programs.

The genetic linkage of marker molecules can be established by a gene mapping model such as, without limitation, the flanking marker model reported by Lander and Botstein (1989), and the interval mapping, based on maximum likelihood methods described by Lander and Botstein (1989), and implemented in the software package MAPMAKER/QTL. Additional software includes Qgene, Version 2.23 (1996) (Department of Plant Breeding and Biometry, 266 Emerson Hall, Cornell University, Ithaca, N.Y.).

B. Inherited Markers

Genetic markers comprise detected differences (polymorphisms) in the genetic information carried by two or more plants. Genetic mapping of a locus with genetic markers typically requires two fundamental components: detectably polymorphic alleles and recombination or segregation of those alleles. In plants, the recombination measured is virtually always meiotic, and therefore, the two inherent requirements of plant gene mapping are polymorphic genetic markers and one or more plants in which those alleles are segregating.

Markers are preferably inherited in codominant fashion so that the presence of both alleles at a diploid locus is readily detectable, and they are free of environmental variation, i.e., their heritability is 1. A marker genotype typically comprises two marker alleles at each locus in a diploid organism such as soybeans. The marker allelic composition of each locus can be either homozygous or heterozygous. Homozygosity is a condition where both alleles at a locus are characterized by the same nucleotide sequence. Heterozygosity refers to different conditions of the gene at a locus.

A number of different marker types are available for use in genetic mapping. Exemplary genetic marker types for use with the invention include, but are not limited to, restriction fragment length polymorphisms (RFLPs), simple sequence length polymorphisms (SSLPs), amplified fragment length polymorphisms (AFLPs), single nucleotide polymorphisms (SNPs), nucleotide insertions and/or deletions (INDELs) and isozymes. Polymorphisms comprising as little as a single nucleotide change can be assayed in a number of ways. For example, detection can be made by electrophoretic techniques including a single strand conformational polymorphism (Orita et al., 1989), denaturing gradient gel electrophoresis (Myers et al., 1985), or cleavage fragment length polymorphisms (Life Technologies, Inc., Gathersberg, Md. 20877), but the widespread availability of DNA sequencing machines often makes it easier to just sequence amplified products directly. Once the polymorphic sequence difference is known, rapid assays can be designed for progeny testing, typically involving some version of PCR amplification of specific alleles (PASA, Sommer, et al., 1992), or PCR amplification of multiple specific alleles (PAMSA, Dutton and Sommer, 1991).

One method for detection of SNPs in DNA samples is by use of PCR in combination with fluorescent probes for the polymorphism, as described in Livak et al., 1995 and U.S. Pat. No. 5,604,099, incorporated herein by reference. Briefly, two probe oligonucleotides, one of which anneals to the SNP site and the other which anneals to the wild type sequence, are synthesized. It is preferable that the site of the SNP be near the 5' terminus of the probe oligonucleotides.

Each probe is then labeled on the 3' end with a non-fluorescent quencher and a minor groove binding moiety which lower background fluorescence and lower the $T_m$ of the oligonucleotide, respectively. The 5' ends of each probe are labeled with a different fluorescent dye wherein fluorescence is dependent upon the dye being cleaved from the probe. Some non-limiting examples of such dyes include VIC™ and 6-FAM™. DNA suspected of comprising a given SNP is then subjected to PCR using a polymerase with 5'-3' exonuclease activity and flanking primers. PCR is performed in the presence of both probe oligonucleotides. If the probe is bound to a complimentary sequence in the test DNA then exonuclease activity of the polymerase releases a fluorescent label activating its fluorescent activity. Therefore, test DNA that contains only wild type sequence will exhibit fluorescence associated with the label on the wild type probe. On the other hand, DNA containing only the SNP sequence will have fluorescent activity from the label on the SNP probe. However, in the case that the DNA is from heterogeneous sources, significant fluorescence of both labels will be observed. This type of indirect genotyping at known SNP sites enables high throughput, inexpensive screening of DNA samples. Thus such a system is ideal for the identification of progeny soybean plants comprising mutant Gy alleles.

Restriction fragment length polymorphisms (RFLPs) are genetic differences detectable by DNA fragment lengths, typically revealed by agarose gel electrophoresis, after restriction endonuclease digestion of DNA. There are large numbers of restriction endonucleases available, characterized by their nucleotide cleavage sites and their source, e.g., EcoRI. RFLPs result from both single-bp polymorphisms within restriction site sequences and measurable insertions or deletions within a given restriction fragment. RFLPs are easy and relatively inexpensive to generate (require a cloned DNA, but no sequence) and are co-dominant. RFLPs have the disadvantage of being labor-intensive in the typing stage, although this can be alleviated to some extent by multiplexing many of the tasks and reutilization of blots. Most RFLP are biallelic and of lesser polymorphic content than microsatellites. For these reasons, the use of RFLP in plant genetic maps has waned.

One of skill in the art would recognize that many types of molecular markers are useful as tools to monitor genetic inheritance and are not limited to RFLPs, SSRs and SNPs, and one of skill would also understand that a variety of detection methods may be employed to track the various molecular markers. One skilled in the art would also recognize that markers of different types may be used for mapping, especially as technology evolves and new types of markers and means for identification are identified.

For purposes of convenience, inherited marker genotypes may be converted to numerical scores, e.g., if there are 2 forms of an SNP, or other marker, designated A and B, at a particular locus using a particular enzyme, then diploid complements may be converted to a numerical score, for example, are AA=2, AB=1, and BB=0; or AA=1, AB=0 and BB=−1. The absolute values of the scores are not important. What is important is the additive nature of the numeric designations. The above scores relate to codominant markers. A similar scoring system can be given that is consistent with dominant markers.

C. Marker Assisted Selection

The invention provides soybean plants with increased β-conglycinin content in combination with a commercially significant yield and agronomically elite characteristics. Such plants may be produced in accordance with the invention by marker assisted selection methods comprising assaying genomic DNA for the presence of markers that are genetically linked to the non-transgenic, mutant Gy1, Gy2, Gy3, Gy4, or Gy5 alleles, including all possible combinations thereof. The invention also provides soybean plants with reduced lipoxygenase content. Such plants may be produced in accordance with the invention by marker assisted selection methods comprising assaying genomic DNA for the presence of markers that are genetically linked to the non-transgenic, mutant Lox1, Lox2, or Lox3 alleles, including all possible combinations thereof.

In certain embodiments of the invention, it may be desired to obtain additional markers linked to Gy alleles. This may be carried out, for example, by first preparing an $F_2$ population by selfing an $F_1$ hybrid produced by crossing inbred varieties only one of which comprises mutant Gy allele conferring decreased glycinin content. Recombinant inbred lines (RIL) (genetically related lines; usually >$F_5$, developed from continuously selfing $F_2$ lines towards homozygosity) can then be prepared and used as a mapping population. Information obtained from dominant markers can be maximized by using RIL because all loci are homozygous or nearly so. It may also be desired to obtain additional markers linked to Lox alleles. This may be carried out, for example, by first preparing an $F_2$ population by selfing an $F_1$ hybrid produced by crossing inbred varieties only one of which comprises a mutant Lox allele conferring decreased lipoxygenase content. As above, recombinant inbred lines can then be prepared and used as a mapping population, and information obtained from dominant markers can be maximized by using RIL because all loci are homozygous or nearly so.

Figure 9:
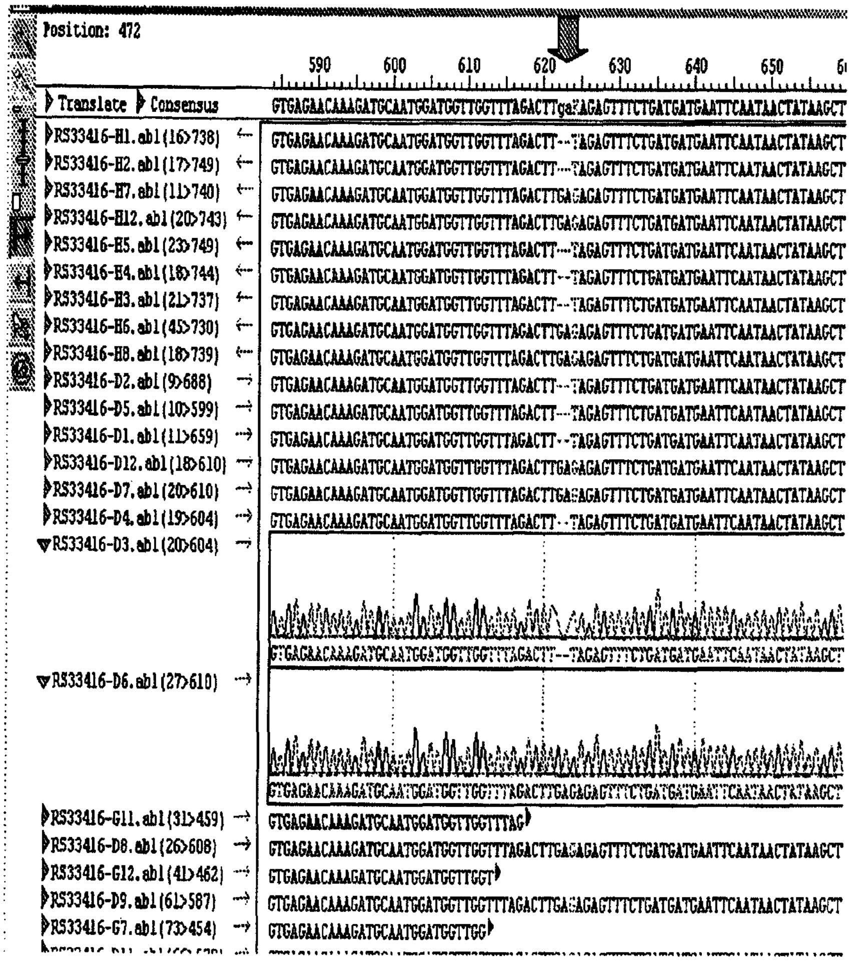
FIG. 9: Alignment of sequences for Kunitz Trypsin inhibitor showing deletion/insertion in Kunitz null mutant lines.

The invention also provides soybean plants with reduced content of KTI, such as a KTI-null trait, which may be obtained by marker assisted selection and provided in combination with commercially significant yield and agronomically elite characteristics. Such plants may be defined, in certain embodiments of the invention, as having a yield in excess of about 35, 37, 39, 41, 43 or 45 bushels per acre over at least 10 environments. In certain embodiments of the invention, the markers used for such marker assisted selection may include SNPs or INDELs. In specific embodiments of the invention, the one or more INDEL(s) may be found in a gene encoding Kunitz Trypsin inhibitor. In one embodiment of the invention, the marker may comprise a deletion at position 622-623 and/or an insertion at position 664 in a gene encoding Kunitz Trypsin Inhibitor (SEQ ID NO:167) as shown in FIG. 9, and the plants may be produced in accordance with the invention by marker assisted selection methods comprising assaying genomic DNA for the presence of such markers.

Backcross populations (e.g., generated from a cross between a desirable variety (recurrent parent) and another variety (donor parent)) carrying a trait not present in the former can also be utilized as a mapping population. A series of backcrosses to the recurrent parent can be made to recover most of its desirable traits. Thus a population is created consisting of individuals similar to the recurrent parent but each individual carries varying amounts of genomic regions from the donor parent. Backcross populations can be useful for mapping dominant markers if all loci in the recurrent parent are homozygous and the donor and recurrent parent have contrasting polymorphic marker alleles (Reiter et al., 1992).

Useful populations for mapping purposes are near-isogenic lines (NIL). NILs are created by many backcrosses to produce an array of individuals that are nearly identical in genetic composition except for the desired trait or genomic region can be used as a mapping population. In mapping with NILs, only a portion of the polymorphic loci are expected to map to a selected region. Mapping may also be carried out on transformed plant lines.

D. Plant Breeding Methods

Certain aspects of the invention provide methods for marker assisted breeding of plants that enable the introduction of non-transgenic, mutant Gy alleles into a heterologous soybean genetic background. Certain aspects of the invention also provide methods for marker assisted breeding of plants that enable the introduction of non-transgenic, mutant Lox alleles into a heterologous soybean genetic background. In general, breeding techniques take advantage of a plant's method of pollination. There are two general methods of pollination: self-pollination which occurs if pollen from one flower is transferred to the same or another flower of the same plant, and cross-pollination which occurs if pollen comes to it from a flower on a different plant. Plants that have been self-pollinated and selected for type over many generations become homozygous at almost all gene loci and produce a uniform population of true breeding progeny, homozygous plants.

In development of suitable varieties, pedigree breeding may be used. The pedigree breeding method for specific traits involves crossing two genotypes. Each genotype can have one or more desirable characteristics lacking in the other; or, each genotype can complement the other. If the two original parental genotypes do not provide all of the desired characteristics, other genotypes can be included in the breeding population. Superior plants that are the products of these crosses are selfed and are again advanced in each successive generation. Each succeeding generation becomes more homogeneous as a result of self-pollination and selection. Typically, this method of breeding involves five or more generations of selfing and selection: $S_1 \rightarrow S_2$; $S_2 \rightarrow S_3$; $S_3 \rightarrow S_4$; $S_4 \rightarrow S_5$, etc. A selfed generation (S) may be considered to be a type of filial generation (F) and may be named F as such. After at least five generations, the inbred plant is considered genetically pure.

Each breeding program should include a periodic, objective evaluation of the efficiency of the breeding procedure. Evaluation criteria vary depending on the goal and objectives. Promising advanced breeding lines are thoroughly tested and compared to appropriate standards in environments representative of the commercial target area(s) for generally three or more years. Identification of individuals that are genetically superior is difficult because genotypic value can be masked by confounding plant traits or environmental factors. One method of identifying a superior plant is to observe its performance relative to other experimental plants and to one or more widely grown standard varieties. Single observations can be inconclusive, while replicated observations provide a better estimate of genetic worth.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued. Descriptions of other breeding methods that are commonly used for different traits and crops can be found in one of several reference books (e.g., Allard, 1960; Simmonds, 1979; Sneep et al., 1979; Fehr, 1987a,b).

The effectiveness of selecting for genotypes with traits of interest (e.g., high yield, disease resistance, fatty acid profile) in a breeding program will depend upon: 1) the extent to which the variability in the traits of interest of individual plants in a population is the result of genetic factors and is thus transmitted to the progenies of the selected genotypes; and 2) how much the variability in the traits of interest among the plants is due to the environment in which the different genotypes are growing. The inheritance of traits ranges from control by one major gene whose expression is not influenced by the environment (i.e., qualitative characters) to control by many genes whose effects are greatly influenced by the environment (i.e., quantitative characters). Breeding for quantitative traits such as yield is further characterized by the fact that: 1) the differences resulting from the effect of each gene are small, making it difficult or impossible to identify them individually; 2) the number of genes contributing to a character is large, so that distinct segregation ratios are seldom if ever obtained; and 3) the effects of the genes may be expressed in different ways based on environmental variation. Therefore, the accurate identification of transgressive segregates or superior genotypes with the traits of interest is extremely difficult and its success is dependent on the plant breeder's ability to minimize the environmental variation affecting the expression of the quantitative character in the population.

The likelihood of identifying a transgressive segregant is greatly reduced as the number of traits combined into one genotype is increased. For example, if a cross is made between cultivars differing in three complex characters, such as yield, β-conglycinin content and at least a first agronomic trait, it is extremely difficult without molecular tools to recover simultaneously by recombination the maximum number of favorable genes for each of the three characters into one genotype. Consequently, all the breeder can generally hope for is to obtain a favorable assortment of genes for the first complex character combined with a favorable assortment of genes for the second character into one genotype in addition to a selected gene.

Backcrossing is an efficient method for transferring specific desirable traits. This can be accomplished, for example, by first crossing a superior variety inbred (A) (recurrent parent) to a donor inbred (non-recurrent parent), which carries the appropriate gene(s) for the trait in question (Fehr, 1987). The progeny of this cross are then mated back to the superior recurrent parent (A) followed by selection in the resultant progeny for the desired trait to be transferred from the non-recurrent parent. Such selection can be based on genetic assays, as mentioned below, or alternatively, can be based on the phenotype of the progeny plant. After five or more backcross generations with selection for the desired trait, the progeny are heterozygous for loci controlling the characteristic being transferred, but are like the superior parent for most or almost all other genes. The last generation of the backcross is selfed, or sibbed, to give pure breeding progeny for the gene(s) being transferred, for example, loci providing the plant with decreased seed glycinin content.

In one embodiment of the invention, the process of backcross conversion may be defined as a process including the steps of:

(a) crossing a plant of a first genotype containing one or more desired gene, DNA sequence or element, such as mutant Gy1, Gy2, Gy3, Gy4, and/or Gy5 alleles associated with decreased seed glycinin content, to a plant of a second genotype lacking said desired gene, DNA sequence or element;

(b) selecting one or more progeny plant(s) containing the desired gene, DNA sequence or element;

(c) crossing the progeny plant to a plant of the second genotype; and (d) repeating steps (b) and (c) for the purpose of transferring said desired gene, DNA sequence or element from a plant of a first genotype to a plant of a second genotype.

Introgression of a particular DNA element or set of elements into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid. During breeding, the genetic markers linked to decreased glycinin content may be used to assist in breeding for the purpose of producing soybean plants with decreased glycinin content and preferably increased β-conglycinin content. Backcrossing and marker assisted selection in particular can be used with the present invention to introduce the decreased glycinin content trait in accordance with the current invention into any variety by conversion of that variety with non-transgenic, mutant Gy1, Gy2, Gy3, Gy4, and/or Gy5 alleles associated.

The selection of a suitable recurrent parent is an important step for a successful backcrossing procedure. The goal of a backcross protocol is to alter or substitute a trait or characteristic in the original inbred. To accomplish this, one or more loci of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross, which in the case of the present invention may be to add one or more allele(s) conferring decreased glycinin content. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred. In the case of the present invention, one may test the glycinin content of progeny lines generated during the backcrossing program, for example by SDS-PAGE/Coomassie staining as well as using the marker system described herein to select lines based upon markers rather than visual traits.

Soybean plants (*Glycine max* L.) can be crossed by either natural or mechanical techniques (see, e.g., Fehr, 1980). Natural pollination occurs in soybeans either by self pollination or natural cross pollination, which typically is aided by pollinating organisms. In either natural or artificial crosses, flowering and flowering time are an important consideration. Soybean is a short-day plant, but there is considerable genetic variation for sensitivity to photoperiod (Hamner, 1969; Criswell and Hume, 1972). The critical day length for flowering ranges from about 13 h for genotypes adapted to tropical latitudes to 24 h for photoperiod-insensitive genotypes grown at higher latitudes (Shibles et al., 1975). Soybeans seem to be insensitive to day length for 9 days after emergence. Photoperiods shorter than the critical day length are required for 7 to 26 days to complete flower induction (Borthwick and Parker, 1938; Shanmugasundaram and Tsou, 1978).

Either with or without emasculation of the female flower, hand pollination can be carried out by removing the stamens and pistil with a forceps from a flower of the male parent and gently brushing the anthers against the stigma of the female flower. Access to the stamens can be achieved by removing the front sepal and keel petals, or piercing the keel with closed forceps and allowing them to open to push the petals away. Brushing the anthers on the stigma causes them to rupture, and the highest percentage of successful crosses is obtained when pollen is clearly visible on the stigma. Pollen shed can be checked by tapping the anthers before brushing the stigma. Several male flowers may have to be used to obtain suitable pollen shed when conditions are unfavorable, or the same male may be used to pollinate several flowers with good pollen shed.

Genetic male sterility is available in soybeans and may be useful to facilitate hybridization in the context of the current invention, particularly for recurrent selection programs (Brim and Stuber, 1973). The distance required for complete isolation of a crossing block is not clear; however, outcrossing is less than 0.5% when male-sterile plants are 12 m or more from a foreign pollen source (Boerma and Moradshahi, 1975). Plants on the boundaries of a crossing block probably sustain the most outcrossing with foreign pollen and can be eliminated at harvest to minimize contamination.

Once harvested, pods are typically air-dried at not more than 38° C. until the seeds contain 13% moisture or less, then the seeds are removed by hand. Seed can be stored satisfactorily at about 25° C. for up to a year if relative humidity is 50% or less. In humid climates, germination percentage declines rapidly unless the seed is dried to 7% moisture and stored in an air-tight container at room temperature. Long-term storage in any climate is best accomplished by drying seed to 7% moisture and storing it at 10° C. or less in a room maintained at 50% relative humidity or in an air-tight container.

III. TRAITS FOR MODIFICATION AND IMPROVEMENT OF SOYBEAN VARIETIES

In certain embodiments, a soybean plant provided by the invention may comprise one or more transgene(s). One example of such a transgene confers herbicide resistance. Common herbicide resistance genes include an EPSPS gene conferring glyphosate resistance, a neomycin phosphotransferase II (nptII) gene conferring resistance to kanamycin (Fraley et al., 1983), a hygromycin phosphotransferase gene conferring resistance to the antibiotic hygromycin (Vanden Elzen et al., 1985), genes conferring resistance to glufosinate or broxynil (Comai et al., 1985; Gordon-Kamm et al., 1990; Stalker et al., 1988) such as dihydrofolate reductase and acetolactate synthase (Eichholtz et al., 1987, Shah et al., 1986, Charest et al., 1990). Further examples include mutant ALS and AHAS enzymes conferring resistance to imidazalinone or a sulfonylurea (Lee et al., 1988; Miki et al., 1990), a phosphinothricin-acetyl-transferase gene conferring phosphinothricin resistance (European Appln. 0 242 246), genes conferring resistance to phenoxy proprionic acids and cycloshexones, such as sethoxydim and haloxyfop (Marshall et al., 1992); and genes conferring resistance to triazine (psbA and gs+ genes) and benzonitrile (nitrilase gene) (Przibila et al., 1991).

A plant of the invention may also comprise a gene that confers resistance to insect, pest, viral or bacterial attack. For example, a gene conferring resistance to a pest, such as soybean cyst nematode was described in PCT Application WO96/30517 and PCT Application WO93/19181. Jones et al., (1994) describe cloning of the tomato Cf-9 gene for resistance to *Cladosporium flavum*); Martin et al., (1993) describe a tomato Pto gene for resistance to *Pseudomonas syringae* pv. and Mindrinos et al., (1994) describe an *Arabidopsis* RSP2 gene for resistance to *Pseudomonas syringae. Bacillus thuringiensis* endotoxins may also be used for insect resistance. (See, for example, Geiser et al., (1986). A vitamin-binding protein such as avidin may also be used as a larvicide (PCT application US93/06487).

The use of use of viral coat proteins in transformed plant cells is known to impart resistance to viral infection and/or disease development affected by the virus from which the coat protein gene is derived, as well as by related viruses. (See Beachy et al., 1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id. Developmental-arrestive proteins produced in nature by a pathogen or a parasite may also be used. For example, Logemann et al., (1992), have shown that transgenic plants expressing the barley ribosome-inactivating gene have an increased resistance to fungal disease.

Transgenes may also be used conferring increased nutritional value or another value-added trait. One example is modified fatty acid metabolism, for example, by transforming a plant with an antisense gene of stearoyl-ACP desaturase to increase stearic acid content of the plant. (See Knutzon et al., 1992). A sense desaturase gene may also be introduced to alter fatty acid content. Phytate content may be modified by introduction of a phytase-encoding gene to enhance breakdown of phytate, adding more free phosphate to the transformed plant. Modified carbohydrate composition may also be affected, for example, by transforming plants with a gene coding for an enzyme that alters the branching pattern of starch. (See Shiroza et al., 1988) (nucleotide sequence of *Streptococcus mutans* fructosyltransferase gene); Steinmetz et al., (1985) (nucleotide sequence of *Bacillus subtilis* levansucrase gene); Pen et al., (1992) (production of transgenic plants that express *Bacillus licheniformis* α-amylase); Elliot et al., (1993) (nucleotide sequences of *tomato* invertase genes); Søgaard et al., (1993) (site-directed mutagenesis of barley α-amylase gene); and Fisher et al., (1993) (maize endosperm starch branching enzyme II)).

Transgenes may also be used to alter protein metabolism. For example, U.S. Pat. No. 5,545,545 describes lysine-insensitive maize dihydrodipicolinic acid synthase (DHPS), which is substantially resistant to concentrations of L-lysine which otherwise inhibit the activity of native DHPS. Similarly, EP 0640141 describes sequences encoding lysine-insensitive aspartokinase (AK) capable of causing a higher than normal production of threonine, as well as a subfragment encoding antisense lysine ketoglutarate reductase for increasing lysine.

In another embodiment, a transgene may be employed that alters plant carbohydrate metabolism. For example, fructokinase genes are known for use in metabolic engineering of fructokinase gene expression in transgenic plants and their fruit (see U.S. Pat. No. 6,031,154). A further example of transgenes that may be used are genes that alter grain yield. For example, U.S. Pat. No. 6,486,383 describes modification of starch content in plants with subunit proteins of adenosine diphosphoglucose pyrophosphorylase ("ADPG PPase"). In EP0797673, transgenic plants are discussed in which the introduction and expression of particular DNA molecules results in the formation of easily mobilized phosphate pools outside the vacuole and an enhanced biomass production and/or altered flowering behavior. Still further known are genes for altering plant maturity. U.S. Pat. No. 6,774,284 describes DNA encoding a plant lipase and methods of use thereof for controlling senescence in plants. U.S. Pat. No. 6,140,085 discusses FCA genes for altering flowering characteristics, particularly timing of flowering. U.S. Pat. No. 5,637,785 discusses genetically modified plants having modulated flower development such as having early floral meristem development and comprising a structural gene encoding the LEAFY protein in its genome.

Genes for altering plant morphological characteristics are also known and may be used in accordance with the invention. U.S. Pat. No. 6,184,440 discusses genetically engineered plants which display altered structure or morphology as a result of expressing a cell wall modulation transgene. Examples of cell wall modulation transgenes include a cellulose binding domain, a cellulose binding protein, or a cell wall modifying protein or enzyme such as endoxyloglucan transferase, xyloglucan endo-transglycosylase, an expansin, cellulose synthase, or a novel isolated endo-1,4-β-glucanase.

Methods for introduction of a transgene are well known in the art and include biological and physical, plant transformation protocols. See, for example, Miki et al. (1993).

Once a transgene is introduced into a variety it may readily be transferred by crossing. By using backcrossing, essentially all of the desired morphological and physiological characteristics of a variety are recovered in addition to the locus transferred into the variety via the backcrossing technique. Backcrossing methods can be used with the present invention to improve or introduce a characteristic into a plant (Poehlman et al., 1995; Fehr, 1987a,b).

IV. TISSUE CULTURES AND IN VITRO REGENERATION OF SOYBEAN PLANTS

A further aspect of the invention relates to tissue cultures of a soybean variety of the invention. As used herein, the term "tissue culture" indicates a composition comprising isolated cells of the same or a different type or a collection of such cells organized into parts of a plant. Exemplary types of tissue cultures are protoplasts, calli and plant cells that are intact in plants or parts of plants, such as embryos, pollen, flowers, leaves, roots, root tips, anthers, and the like. In a preferred embodiment, the tissue culture comprises embryos, protoplasts, meristematic cells, pollen, leaves or anthers.

Exemplary procedures for preparing tissue cultures of regenerable soybean cells and regenerating soybean plants therefrom, are disclosed in U.S. Pat. No. 4,992,375; U.S. Pat. No. 5,015,580; U.S. Pat. No. 5,024,944, and U.S. Pat. No. 5,416,011, each of the disclosures of which is specifically incorporated herein by reference in its entirety.

An important ability of a tissue culture is the capability to regenerate fertile plants. This allows, for example, transformation of the tissue culture cells followed by regeneration of transgenic plants. For transformation to be efficient and successful, DNA must be introduced into cells that give rise to plants or germ-line tissue.

Soybeans typically are regenerated via two distinct processes; shoot morphogenesis and somatic embryogenesis (Finer, 1996). Shoot morphogenesis is the process of shoot meristem organization and development. Shoots grow out from a source tissue and are excised and rooted to obtain an intact plant. During somatic embryogenesis, an embryo (similar to the zygotic embryo), containing both shoot and root axes, is formed from somatic plant tissue. An intact plant rather than a rooted shoot results from the germination of the somatic embryo.

Shoot morphogenesis and somatic embryogenesis are different processes and the specific route of regeneration is primarily dependent on the explant source and media used for tissue culture manipulations. While the systems are different, both systems show variety-specific responses where some lines are more responsive to tissue culture manipulations than others. A line that is highly responsive in shoot morphogenesis may not generate many somatic embryos. Lines that produce large numbers of embryos during an 'induction' step may not give rise to rapidly-growing proliferative cultures. Therefore, it may be desired to optimize tissue culture conditions for each soybean line. These optimizations may readily be carried out by one of skill in the art of tissue culture through small-scale culture studies. In addition to line-specific responses, proliferative cultures can be observed with both shoot morphogenesis and somatic embryogenesis. Proliferation is beneficial for both systems, as it allows a single, transformed cell to multiply to the point that it will contribute to germ-line tissue.

Shoot morphogenesis was first reported by Wright et al. (1986) as a system whereby shoots were obtained de novo from cotyledonary nodes of soybean seedlings. The shoot meristems were formed subepidermally and morphogenic tissue could proliferate on a medium containing benzyl adenine (BA). This system can be used for transformation if the subepidermal, multicellular origin of the shoots is recognized and proliferative cultures are utilized. The idea is to target tissue that will give rise to new shoots and proliferate those cells within the meristematic tissue to lessen problems associated with chimerism. Formation of chimeras, resulting from transformation of only a single cell in a meristem, are problematic if the transformed cell is not adequately proliferated and does not give rise to germ-line tissue. Once the system is well understood and reproduced satisfactorily, it can be used as one target tissue for soybean transformation.

Somatic embryogenesis in soybean was first reported by Christianson et al. (1983) as a system in which embryogenic tissue was initially obtained from the zygotic embryo axis. These embryogenic cultures were proliferative but the repeatability of the system was low and the origin of the embryos was not reported. Later histological studies of a different proliferative embryogenic soybean culture showed that proliferative embryos were of apical or surface origin with a small number of cells contributing to embryo formation. The origin of primary embryos (the first embryos derived from the initial explant) is dependent on the explant tissue and the auxin levels in the induction medium (Hartweck et al., 1988). With proliferative embryonic cultures, single cells or small groups of surface cells of the 'older' somatic embryos form the 'newer' embryos.

Embryogenic cultures can also be used successfully for regeneration, including regeneration of transgenic plants, if the origin of the embryos is recognized and the biological limitations of proliferative embryogenic cultures are understood. Biological limitations include the difficulty in developing proliferative embryogenic cultures and reduced fertility problems (culture-induced variation) associated with plants regenerated from long-term proliferative embryogenic cultures. Some of these problems are accentuated in prolonged cultures. The use of more recently cultured cells may decrease or eliminate such problems.

V. UTILIZATION OF SOYBEAN PLANTS

A soybean plant provided by the invention may be used for any purpose deemed of value. Common uses include the preparation of food for human consumption, feed for non-human animal consumption and industrial uses. As used herein, "industrial use" or "industrial usage" refers to non-food and non-feed uses for soybeans or soy-based products.

Soybeans are commonly processed into two primary products, soybean protein (meal) and crude soybean oil. Both of these products are commonly further refined for particular uses. Refined oil products can be broken down into glycerol, fatty acids and sterols. These can be for food, feed or industrial usage. Edible food product use examples include coffee creamers, margarine, mayonnaise, pharmaceuticals, salad dressings, shortenings, bakery products, and chocolate coatings.

Soy protein products (e.g., meal), can be divided into soy flour concentrates and isolates which have both food/feed and industrial use. Soy flour and grits are often used in the manufacturing of meat extenders and analogs, pet foods, baking ingredients and other food products. Food products made from soy flour and isolate include baby food, candy products, cereals, food drinks, noodles, yeast, beer, ale, etc. Soybean meal in particular is commonly used as a source of protein in livestock feeding, primarily swine and poultry. Feed uses thus include, but are not limited to, aquaculture feeds, bee feeds, calf feed replacers, fish feed, livestock feeds, poultry feeds and pet feeds, etc.

Whole soybean products can also be used as food or feed. Common food usage includes products such as the seed, bean sprouts, baked soybean, full fat soy flour used in various products of baking, roasted soybean used as confectioneries, soy nut butter, soy coffee, and other soy derivatives of oriental foods. For feed usage, hulls are commonly removed from the soybean and used as feed.

Soybeans additionally have many industrial uses. One common industrial usage for soybeans is the preparation of binders that can be used to manufacture composites. For example, wood composites may be produced using modified soy protein, a mixture of hydrolyzed soy protein and PF resins, soy flour containing powder resins, and soy protein containing foamed glues. Soy-based binders have been used to manufacture common wood products such as plywood for over 70 years. Although the introduction of urea-formaldehyde and phenol-formaldehyde resins has decreased the usage of soy-based adhesives in wood products, environmental concerns and consumer preferences for adhesives made from a renewable feedstock have caused a resurgence of interest in developing new soy-based products for the wood composite industry.

Preparation of adhesives represents another common industrial usage for soybeans. Examples of soy adhesives include soy hydrolyzate adhesives and soy flour adhesives. Soy hydrolyzate is a colorless, aqueous solution made by reacting soy protein isolate in a 5 percent sodium hydroxide solution under heat (120° C.) and pressure (30 psig). The resulting degraded soy protein solution is basic (pH 11) and flowable (approximately 500 cps) at room temperature. Soy flour is a finely ground, defatted meal made from soybeans. Various adhesive formulations can be made from soy flour, with the first step commonly requiring dissolving the flour in a sodium hydroxide solution. The strength and other properties of the resulting formulation will vary depending on the additives in the formulation. Soy flour adhesives may also potentially be combined with other commercially available resins.

Soybean oil may find application in a number of industrial uses. Soybean oil is the most readily available and one of the lowest-cost vegetable oils in the world. Common industrial uses for soybean oil include use as components of anti-static agents, caulking compounds, disinfectants, fungicides, inks, paints, protective coatings, wallboard, anti-foam agents, alcohol, margarine, paint, ink, rubber, shortening, cosmetics, etc. Soybean oils have also for many years been a major ingredient in alkyd resins, which are dissolved in carrier solvents to make oil-based paints. The basic chemistry for converting vegetable oils into an alkyd resin under heat and pressure is well understood to those of skill in the art.

Soybean oil in its commercially available unrefined or refined, edible-grade state, is a fairly stable and slow-drying oil. Soybean oil can also be modified to enhance its reactivity under ambient conditions or, with the input of energy in various forms, to cause the oil to copolymerize or cure to a dry film. Some of these forms of modification have included epoxidation, alcoholysis or transesterification, direct esterification, metathesis, isomerization, monomer modification, and various forms of polymerization, including heat bodying. The reactive linoleic-acid component of soybean oil with its double bonds may be more useful than the predominant oleic- and linoleic-acid components for many industrial uses.

Solvents can also be prepared using soy-based ingredients. For example, methyl soyate, a soybean-oil based methyl ester, is gaining market acceptance as an excellent solvent replacement alternative in applications such as parts cleaning and degreasing, paint and ink removal, and oil spill remediation. It is also being marketed in numerous formulated consumer products including hand cleaners, car waxes and graffiti removers. Methyl soyate is produced by the transesterification of soybean oil with methanol. It is commercially available from numerous manufacturers and suppliers. As a solvent, methyl soyate has important environmental- and safety-related properties that make it attractive for industrial applications. It is lower in toxicity than most other solvents, is readily biodegradable, and has a very high flash point and a low level of volatile organic compounds (VOCs). The compatibility of methyl soyate is excellent with metals, plastics, most elastomers and other organic solvents. Current uses of methyl soyate include cleaners, paint strippers, oil spill cleanup and bioremediation, pesticide adjuvants, corrosion preventives and biodiesel fuels additives.

VI. DEPOSIT INFORMATION

Deposits of at least 2500 seeds of the soybean lines B2G2 and Pedigree 3 disclosed herein have been made with the American Type Culture Collection (ATCC), 10801 University Boulevard, Manassas, Va. 20110-2209 USA on Jul. 28, 2005. The deposits were assigned ATCC Accession Nos. PTA-6893, and PTA-6892, respectively. The seeds were deposited with the ATCC. Access to this deposit will be available during the pendency of the application in accordance with the Budapest Treaty. The deposits will be maintained in the ATCC Depository, which is a public depository, for a period of 30 years, or 5 years after the most recent request, or for the enforceable life of the patent, whichever is longer, and will be replaced if it becomes nonviable during that period.

VII. KITS

Any of the compositions described herein may be comprised in a kit. In a non-limiting example, a composition for the detection of a polymorphism as described herein and/or additional agents, may be comprised in a kit. The kits may thus comprise, in suitable container means, a probe or primer for detection of the polymorphism and/or an additional agent of the present invention. In specific embodiments, the kit will allow detection of at least one non-transgenic Gy null allele, and may further provide for the detection of a lipoxygenase and/or KTI null allele, for example, by detection of polymorphisms in such alleles and/or otherwise in linkage disequilibrium with the allele(s).

The kits may comprise a suitably aliquoted agent composition(s) of the present invention, whether labeled or unlabeled for any assay format desired to detect such alleles. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the detection composition and any other reagent containers in close confinement for commercial sale. Such containers may include injection or blow-molded plastic containers into which the desired vials are retained.

When the components of the kit are provided in one and/or more liquid solutions, the liquid solution may be an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means. The container means will generally include at least one vial, test tube, flask, bottle, syringe and/or other container means, into which the composition for detecting a null allele are placed, preferably, suitably allocated. The kits may also comprise a second container means for containing a sterile buffer and/or other diluent.

The kits of the present invention will also typically include a means for containing the vials in close confinement for commercial sale, such as, e.g., injection and/or blow-molded plastic containers into which the desired vials are retained. Irrespective of the number and/or type of containers, the kits of the invention may also comprise, and/or be packaged with, an instrument for assisting with the use of the detection compositions.

VIII. DEFINITIONS

In the description and tables which follow, a number of terms are used. In order to provide a clear and consistent understanding of the specification and claims, the following definitions are provided:

A: When used in conjunction with the word "comprising" or other open language in the claims, the words "a" and "an" denote "one or more."

Agronomically Elite: As used herein, means a genotype that has a culmination of many distinguishable traits such as seed yield, emergence, vigor, vegetative vigor, disease resistance, seed set, standability and threshability which allows a producer to harvest a product of commercial significance.

Allele: Any of one or more alternative forms of a gene locus, all of which alleles relate to a trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Commercially Significant Yield: A yield of grain having commercial significance to the grower represented by an actual grain yield of at least 95% of the check lines AG2703 and DKB23-51 when grown under the same conditions.

Crossing: The mating of two parent plants.

Cross-pollination: Fertilization by the union of two gametes from different plants.

Down-regulatory mutation: For the purposes of this application a down regulatory mutation is defined as a mutation that reduces the expression levels of a protein from a given gene. Thus a down-regulatory mutation comprises null mutations.

$F_1$ Hybrid: The first generation progeny of the cross of two nonisogenic plants.

Genotype: The genetic constitution of a cell or organism.

INDEL: Genetic mutations resulting from insertion or deletion of nucleotide sequence.

Industrial use: A non-food and non-feed use for a soybean plant. The term “soybean plant” includes plant parts and derivatives of a soybean plant.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Non-transgenic mutation: A mutation that is naturally occurring, or induced by conventional methods (e.g. exposure of plants to radiation or mutagenic compounds), not including mutations made using recombinant DNA techniques.

Null phenotype: A null phenotype as used herein means that a given protein is not expressed at levels that can be detected. In the case of the Gy subunits, expression levels are determined by SDS-PAGE and Coomassie staining.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

SNP: Refers to single nucleotide polymorphisms, or single nucleotide mutations when comparing two homologous sequences.

Stringent Conditions: Refers to nucleic acid hybridization conditions of 5×SSC, 50% formamide and 42° C.

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant.

Transgene: A genetic locus comprising a sequence which has been introduced into the genome of a soybean plant by transformation.

IX. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Soybean Varieties Used in Studies

The B2G2 or “11S null” soybean variety has a unique seed composition including high level of β-conglycinin and low amount of glycinin. However, the B2G2 variety exhibits agronomically inferior characteristics such as low yield, excessive lodging and green seed. A number of breeding lines were developed, which carried all or parts of the mutations present in the B2G2 lines. Fifteen such lines together with B2G2 lines were used as mutant lines in resequencing panel. Eight wild types were used for comparison in this study. Table 1 lists all the lines used in the sequencing panel.

TABLE 1

| Line Name or Symbol | Pedigree |
|---|---|
| JB1 | AH_(A3244/(B2G2/A1923: .077.): 0001.0097.0015.)/ DJW2500C0R: @.0042.0006.@. |
| JB2 | AH_(A3244/(B2G2/A1923: .077.): 0001.0064.0001.)/ DKB19-51: @.0232.0002.@. |
| JB3 | AH_(A3244/(B2G2/A1923: .077.): 0001.0064.0001.)/ DKB19-51: @.0228.0015.@. |
| JB4 | AH_(A3244/(B2G2/A1923: .077.): 0001.0097.0011.)/ DAK2501A0R: @.0314.0009.@. |
| JB5 | AH_(A3244/(B2G2/A1923: .077.): 0001.0097.0015.)/ DJW2500C0R: @.0042.0012.@. |
| JB6 | AH_(A3244/(B2G2/A1923: .077.): 0001.0011.0008.)/ AG2402: @.0028.0010.@. |
| JB7 | AH_(A3244/(B2G2/A1923: .077.): 0001.0008.0016.)/ DBL3201A0X: @.0256.0014.@. |
| JB8 | AH_(A3244/(B2G2/A1923: .077.): 0001.0097.0015.)/ DJW2500C0R: @.0234.0019.@. |
| JB9 | AH_704416-24/((A3244/(B2G2/A1923: .077.): 0001.0097.0015.)/ DJW2500C0R: @.0005.): @.0067.0016. |
| JB10 | AH_704416-24/((A3244/(B2G2/A1923: .077.): 0001.0097.0015.)/DJW2500C0R: @.0005.): @.0067.0007. |
| JB11 | AH_704416-24/((A3244/(B2G2/A1923: .077.): 0001.0097.0015.)/DJW2500C0R: @.0005.): @.0067.0003. |
| JB12 | AH_704416-24/((A3244/(B2G2/A1923: .077.): 0001.0097.0015.)/DJW2500C0R: @.0005.): @.0067.0002. |
| JB13 | AH_DAK2301A1R/((A3244/(B2G2/A1923: .077.): 0001.0097.0015.)/DJW2500C0R: @.0013.): @.0018.0001. |
| JB14 | AH_DAK2301A1R/((A3244/(B2G2/A1923: .077.): 0001.0097.0015.)/DJW2500C0R: @.0013.): @.0114.0011. |
| JB15 | AH_DAK2301A1R/((A3244/(B2G2/A1923: .077.): 0001.0097.0015.)/DJW2500C0R: @.0013.): @.0130.0001. |
| B2G2 | |
| A1923 | A1923 |
| A3244 | A3244 |
| AG2403 | AG2403 |
| AG2703 | AG2703 |
| AG3201 | AG3201 |
| AG3202 | AG3202 |

TABLE 1-continued

| Line Name or Symbol | Pedigree |
|---|---|
| DKB 17-51 | DKB 17-51 |
| DKB 19-51 | DKB 19-51 |

Example 2

Design of Markers for Gy Alleles

DNA sequences for all the glycinin genes are available in GenBank (NCBI). These sequences were used as queries to blast against a Monsanto sequence database. Using "blastn" programs, a number of high score hits were obtained. The resulting sequences from the blast search were aligned to provide a high quality consensus sequences for use in primer design. Nested primers were designed to completely cover the entire gene at each locus and amplicons were generated from different lines. Sequences of these amplicons were aligned to identify SNPs and INDELs associated with high β-conglycinin phenotypes. Initially 10 pairs of primers were designed for Gy1, 7 pairs each for Gy2 and Gy3, 14 pairs for Gy4, 10 pairs for Gy5 and 11 pairs for Gy7. Additional primers were designed once their sequences were known from this study. Table 2 lists the primers used in the study.

DNA was isolated with Qiagen Plant DNA kits, and PCR was performed with KOD protocol (EMD Biosciences, Inc, Madison, Wis.). The reaction mix included 3.4 µl 5M Betaine, 2 µl 10×KOD buffer, 2 µl of 2 mM dNTPs, 0.8 µl 25 mM $MgSO_4$, 0.2 µl KOD enzyme (1 U/µl), 1.6 µl primers (5 µM) and 10 µl DNA template (2 ng/µl). PCR cycles were as follows: 94° C. 5 mins; 8 cycles of 94° C. 40 sec, 62° C. 40 sec, 72° C. 1 min, 94° C. 40 sec, 60° C. 40 sec, 72° C. 1 min, 94° C. 40 sec, 58° C. 40 sec, 72° C. 1 min, 94° C. 40 sec, 56° C. 40 sec, 72° C. 1 min; 3 cycles of 94° C. 40 sec, 55° C. 40 sec, 72° C. 1 min; hold at 72° C. for 7 min. PCR products were analyzed by electrophoresis in 1% agarose gels. For sequencing, 5 µl PCR products were removed to a new tube and 1 µl Exonuclease I (1:10 diluted) and 1 µl Shrimp Alkaline Phosphatase (1:100 diluted). The mix was incubated at 37° C. for 20 min and then 80° C. for 20 min to inactivate the enzyme. 40 µl $H_2O$ was added and 6 µl were used as template with 1 µl sequencing primer. Sequencing was performed using a Capillary Sequencer AB13730. Sequences were assembled and aligned using SeqMan II program of the DNAStar™ (LaserGene).

End point SNP/Taqman® assays, were designed and manufactured by Applied Biosystems based on the SNPs sequences provided to them. SNP detection was carried out according to supplied instructions (Applied Biosystems). Taqman® assays, or Real Time PCR, detect the accumulation of a specific PCR product by hybridization and cleavage of a double-labeled fluorogenic probe during the amplification reaction. A Taqman assay includes four oligonucleotides, two of which serve as PCR primers and generate a PCR product encompassing the polymorphism to be detected. The other two are allele-specific fluorescence-resonance-energy-transfer (FRET) probes; each probe has a unique fluorophore that is released upon probe degradation by Taq DNA polymerase, effectively signalling the amount of each allele present in the sample.

TABLE 2

| Primer Name | Forward Primer | Reverse Primer |
|---|---|---|
| Gy1_1 | SEQ ID NO: 1<br>GCCTAAGTACGTACTCAAAATGCCAA | SEQ ID NO: 2<br>CTACACCTCATGAAGTTCATGGTGTGA |
| Gy1_2 | SEQ ID NO: 3<br>CCATGCATGGTCCCCTCGTCATCACGA | SEQ ID NO: 4<br>CCCTCATTTATCAAACCCTTAAACATATT |
| Gy1_3 | SEQ ID NO: 5<br>GAACTTCATGAGGTGTAGCACCCAAGGCTT | SEQ ID NO: 6<br>GATTATGTTACGTCATATGGAAGAAATCAA |
| Gy1_4 | SEQ ID NO: 7<br>CCATATGACGTAACATAATCATATCATTGAT | SEQ ID NO: 8<br>GAATTATAATATCTAATATTGCTATGTGGC |
| Gy1_5 | SEQ ID NO: 9<br>CTCAACAAAGAGGACAAAGCAGCAGACCA | SEQ ID NO: 10<br>GATGACCTCCTTGCTCTTGCTGATATTT |
| Gy1_6 | SEQ ID NO: 11<br>CACCCTGGAATTCTTGGAACATGCATTCA | SEQ ID NO: 12<br>GGAGAGATCCAAACTCAGCACTGAGTC |
| Gy1_7 | SEQ ID NO: 13<br>GCGTGGACAAGCAGATAGCGAA | SEQ ID NO: 14<br>CTTGCGGAGAGATCCAAACTCA |
| Gy1_8 | SEQ ID NO: 15<br>GAGGATGAGAAGCCACAGTGCAAGGG | SEQ ID NO: 16<br>GTATGTTGATCTTTGATGAATGATGTACGTA |
| Gy1_9 | SEQ ID NO: 17<br>GGATGAATTTGTTGTGACTCTTGCATGCA | SEQ ID NO: 18<br>CTGAGACTCCTGAGGTGGAACCAGGAACT |
| Gy1_10 | SEQ ID NO: 19<br>GCAGATAAAGAACAACAACCCTTTCAAG | SEQ ID NO: 20<br>CAACACTTCCTAAAGATATCATCGATCAA |
| Gy2_1 | SEQ ID NO: 21<br>GCAATTGCATGCAATACAAACACACTT | SEQ ID NO: 22<br>GCCACAGTTTCAATCAATTTTACTAACAA |
| Gy2_2 | SEQ ID NO: 23<br>CCATGAACTTAATGAGGTGTAACACACAA | SEQ ID NO: 24<br>AAGATAGGTTGGACGGTTAAGAAGAA |

TABLE 2-continued

| Primer Name | Forward Primer | Reverse Primer |
|---|---|---|
| Gy2_3 | SEQ ID NO: 25<br>ACCGTCCAACCTATCTTATATATTCAA | SEQ ID NO: 26<br>CACCCTCTCTGAAGCGATGTACCTTT |
| Gy2_4 | SEQ ID NO: 27<br>CCTAGCACTTATCAAGAGCCGCAAGAAT | SEQ ID NO: 28<br>CTGCATGTTCACGCCGAACGCTTCTTT |
| Gy2_5 | SEQ ID NO: 29<br>ATATCAGCAGCAGCAGCAAGGAGGTTCC | SEQ ID NO: 30<br>GCAAGTGCTAAGATAACTTTGTCGTCA |
| Gy2_6 | SEQ ID NO: 31<br>CTTGAAAGAAGCGTTCGGCGTGAACAT | SEQ ID NO: 32<br>GCAAGTGCTAAGATAACTTTGTCGTCA |
| Gy2_7 | SEQ ID NO: 33<br>GGATGAATAACATGTTGTGATTAACGTA | SEQ ID NO: 34<br>CAAGGAAGCTGAAAGGGTTGTTGTTCTTC |
| Gy3_1 | SEQ ID NO: 35<br>CACCATTAACTTAATAGTGTAAGACAG | SEQ ID NO: 36<br>CCTTGTTGAATAAAGGTTGTAAGTTGGATT |
| Gy3_2 | SEQ ID NO: 37<br>GATTCCGAAGCCACCTTACACCATTAACTTA | SEQ ID NO: 38<br>GGATAAAATGAACCTTGTTGAATAAAGGTT |
| Gy3_3 | SEQ ID NO: 39<br>GTCTTAAGCTCAGCACCCCACTTCTGAGT | SEQ ID NO: 40<br>GGATAAAATGAACCTTGTTGAATAAAGGTT |
| Gy3_4 | SEQ ID NO: 41<br>CCTCAAGAGTAACGTTAAGGACATCGATA | SEQ ID NO: 42<br>CAGTTATTTAAAGTGATTTCACCACGAGG |
| Gy3_5 | SEQ ID NO: 43<br>AAGAAATTGGACAACGTTGTAACATGCA | SEQ ID NO: 44<br>CAATGTTTGTCTTTCTCGTCACAATCTGG |
| Gy3_6 | SEQ ID NO: 45<br>AAGAAATTGGACAACGTTGTAACATGCA | SEQ ID NO: 46<br>GCTTTTATAACATGAATTAATGATGTAAGTA |
| Gy3_7 | SEQ ID NO: 47<br>GATTAACGTACACTTGATGTATGGTGCA | SEQ ID NO: 48<br>GCATAGGTACTTGAGTGACTCATTACACAA |
| Gy4_1 | SEQ ID NO: 49<br>GCACAGTAAAACAGTTCAAATTGAGAA | SEQ ID NO: 50<br>CATTCTTCACCTTGCATGGCTATTGTT |
| Gy4_2 | SEQ ID NO: 51<br>GCAAGGTGAAGAATGTCACAAACTCAGCAA | SEQ ID NO: 52<br>GGTGACAAATGGATTAATATACACTGAGAA |
| Gy4_3 | SEQ ID NO: 53<br>GGATGATCATCATCGCCCAAGGTAAT | SEQ ID NO: 54<br>CTGGTGACTGTCCTGTAGCTGCTGCTT |
| Gy4_4 | SEQ ID NO: 55<br>TCAAGGTCGCAGAAGCAGCAGCTACAG | SEQ ID NO: 56<br>TGAGAGGGAATTTGTTCATCTTCATCAT |
| Gy4_5 | SEQ ID NO: 57<br>GATGATGAAGATGAACAAATTCCCTCTCAC | SEQ ID NO: 58<br>GTAGAGGACAACATATTGGGCACTGAGTTG |
| Gy4_6 | SEQ ID NO: 59<br>CACCCTCCCAGCCCTCCGCCAATTCCA | SEQ ID NO: 60<br>GTCACATAGATCACACTGTTTGCATTCAGA |
| Gy4_7 | SEQ ID NO: 61<br>TTACTCTCCACATTGGAATCTGAATGCA | SEQ ID NO: 62<br>GCCACTCAGATATAAACATAGGCTCGCTG |
| Gy4_8 | SEQ ID NO: 63<br>CATAAATGACAAGCATGATGGTGTGAGGA | SEQ ID NO: 64<br>CCAGTAAACATATAATCAGTATTACTCATTT |
| Gy4_9 | SEQ ID NO: 65<br>AGCCATGCAAGGTGAAGAATGTCACAAA | SEQ ID NO: 66<br>AAGAGTATCACCAGCATTTCTCAGTGT |
| Gy4_10 | SEQ ID NO: 67<br>CTTTGTTGACATATCAATCACCTTAA | SEQ ID NO: 68<br>GTGAAAGAATTAACAAGTAAGGAGAACA |
| Gy4_11 | SEQ ID NO: 69<br>GTTCTCCTTACTTGTTAATTCTTTCACTT | SEQ ID NO: 70<br>GTCCTGGTCCTGGTCTTGTTCACGCTT |
| Gy4_12 | SEQ ID NO: 71<br>GAAGATCAACCTCGCAAGAGCCGCGAAT | SEQ ID NO: 72<br>CAACTACCCCTAGAGAATCACTAAAGAAT |
| Gy4_13 | SEQ ID NO: 73<br>GTCAGTAAGTATGTTGTAGGGTTGGATT | SEQ ID NO: 74<br>CCATCATGCTTGTCATTTATGCGACTTT |
| Gy4_14 | SEQ ID NO: 75<br>CAAGGCTCACCCCGTGTTAAAGTCGCAT | SEQ ID NO: 76<br>GAATAAAGACAAAACGTGAAGACTGACAT |

TABLE 2-continued

| Primer Name | Forward Primer | Reverse Primer |
|---|---|---|
| Gy5_1 | SEQ ID NO: 77<br>CTCCTTCAAACTTATTAACACTTT | SEQ ID NO: 78<br>CCTTGAACGACAATGATCATTT |
| Gy5_2 | SEQ ID NO: 79<br>CTCAAGGTCGCAGCAGCAACTACAA | SEQ ID NO: 80<br>GAGGGAGTTTGTTCATATTCTTCG |
| Gy5_3 | SEQ ID NO: 81<br>GAAGAATATGAACAAACTCCCTCTT | SEQ ID NO: 82<br>GGACAACATATTGGGCACTGAGTCC |
| Gy5_4 | SEQ ID NO: 83<br>CTCCCAGCCCTCCGCCAATTCGG | SEQ ID NO: 84<br>CACATAGATCACACTGTTCGCGTTCAAG |
| Gy5_5 | SEQ ID NO: 85<br>TACTCTCCACATTGGAACTTGAACGCG | SEQ ID NO: 86<br>CACTCAGATATTAACATAGGCTGGGTC |
| Gy5_6 | SEQ ID NO: 87<br>GGCCCTTTGGTCAACCCATAAATAA | SEQ ID NO: 88<br>AAGACTGACATTTTATTAAGGCGATTC |
| Gy5_7 | SEQ ID NO: 89<br>CATGGAACTCTCAACACCCTGAGCTGCAA | SEQ ID NO: 90<br>CCTCTAGATATAAGATAGTGTTCTTCAA |
| Gy5_8 | SEQ ID NO: 91<br>GTCACTGTTTCCAAACGCACCCTCAA | SEQ ID NO: 92<br>GGGTTCCCAGCAAGGTAAAATACCTT |
| Gy5_9 | SEQ ID NO: 93<br>GTGTTCCTTACTGGACCTATAACACT | SEQ ID NO: 94<br>GGGTGATCAGGACGAGGTTGATCTT |
| Gy5_10 | SEQ ID NO: 95<br>GTCACTGCATAGTATCATACACACTT | SEQ ID NO: 96<br>GTCTGACATCCTCTTCCACGTGGTT |
| Gy7_1 | SEQ ID NO: 97<br>CGAGAACAATAGAAATAGACCATCAGG | SEQ ID NO: 98<br>CCTCTTCACACAATGATCCAAACTC |
| Gy7_2 | SEQ ID NO: 99<br>GTCCAGGGTCCATGTTATCGTCT | SEQ ID NO: 100<br>CATTGTCCTTTCCTTACTGATTCTCC |
| Gy7_3 | SEQ ID NO: 101<br>TGACTGCATGTATCATGTATGTGAAAG | SEQ ID NO: 102<br>GATTCGATGAGGTTGTCAGGTTTC |
| Gy7_4 | SEQ ID NO: 103<br>CGGAGAATCAGTAAGGAAAGGACAA | SEQ ID NO: 104<br>TGAGGTTGTTGGATACCTTGGAGTA |
| Gy7_5 | SEQ ID NO: 105<br>ACCATTCTGCGCTCCATTATTATTT | SEQ ID NO: 106<br>AGTTTCGTCACAACCAGGAATTACA |
| Gy7_6 | SEQ ID NO: 107<br>GTTTAACCATTCTGCGCTCCATTAT | SEQ ID NO: 108<br>GAATATGTCACCCTGCTTCAGGTAA |
| Gy7_7 | SEQ ID NO: 109<br>TGTAATTCCTGGTTGTGACGAAACT | SEQ ID NO: 110<br>GTGGCCTGATAATGCTAAGACCTTT |
| Gy7_8 | SEQ ID NO: 111<br>CGTTACCTGAAGCAGGGTGACATA | SEQ ID NO: 112<br>CACCTCTTCTTCTCCTTCTCCTTCTT |
| Gy7_9 | SEQ ID NO: 113<br>CTTGGAACACGAAGTTAGAGAAGCA | SEQ ID NO: 114<br>CGGTTATTGTGGTTGTAAGTGTGGT |
| Gy7_10 | SEQ ID NO: 115<br>CCCAATGGGTTAAACTCTACAAGGT | SEQ ID NO: 116<br>ATTATTCTTGAGCTCGCTCACTTCC |
| Gy7_11 | SEQ ID NO: 117<br>GTGGTGAACTCCCAGGGAAAGT | SEQ ID NO: 118<br>GAGGAAAGTACAAATAGCAACTGACAA |
| Gy1_473 | SEQ ID NO: 119<br>CGAAGCCACCTCACACCATGAACTTCAT | SEQ ID NO: 120<br>CAGAAGTAGGGTGCTGAGCTTGAGACATT |
| Gy1_579 | SEQ ID NO: 121<br>GTCCCTCATTCACCTTCCTCTCTTCCCTAT | SEQ ID NO: 122<br>GCTTGGCCATGGTGATGACTGATGAGTGT |
| Gy1_794 | SEQ ID NO: 123<br>CTCAATGCCCTCAAACCGGATAACCGTA | SEQ ID NO: 124<br>CAACACCGGCACACTGGAATGGCTTGTT |
| Gy3_1264 | SEQ ID NO: 125<br>GCATGATATTCCCGGGTTGTCCTAGCACAT | SEQ ID NO: 126<br>CCCTCTCTGAAGTGATAGATCTTCTGGTGA |

TABLE 2-continued

| Primer Name | Forward Primer | Reverse Primer |
|---|---|---|
| Gy3_1356 | SEQ ID NO: 127<br>CACTTCAGAGAGGGTGATTTGATTGCAGT | SEQ ID NO: 128<br>GTTCTGGAAGCTGTTGGTGTCAATAAGAGA |

Example 3

Methods for Gy Expression Analysis

Genetic conformation of the Gy markers was carried out in two F2 populations designated JB0305602 and JB0305605, which were derived from the crosses between AAH3504T0C/AH0209439-130 and AAH2104J0C/AH0209439-130, respectively. Four hundred F2 individual plants were sampled and 372 plants were genotyped with SNP markers.

Figure 1:
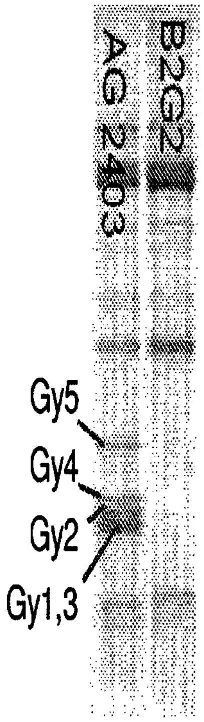
FIG. 1: Protein extracted from the seed of indicated soybean varieties was resolved by SDS-PAGE and visualized by Coomassie staining. The mobility of acidic glycinin subunits encoded by each gene is indicated. Gel resolution was insufficient to separate Gy1 from Gy3 encoded protein subunits.

Protein analysis was carried out as follows: Eight soybean seeds were pooled and ground using the CAT Mega-Grinder (SOP Asci-01-0002). Ground samples were stored at 4° C. For analysis, ~30 mg of flour from each was weighed into one well of a 96 well 2 ml microtiter plate. Protein was extracted for 1 hour with shaking in 1.0 ml 1× Laemmli SDS buffer pH 6.8 containing 0.1M dithiothreitol (DTT) as a reductant. Following centrifugation, a portion of each extract was further diluted in SDS buffer to yield 0.2-0.5 μg/μL total protein, heated to 90-100° C. for 10 min, and cooled. For each sample, 1-2 μg total protein was loaded using a 12 channel pipet onto a 26 lane 15% T gradient Tris/HCl Criterion gel. Molecular weight standards and a parental control were included in two of the lanes in each gel. The gels were electrophoresed until the tracking dye reached the bottom of the gel ~1.2 hrs, then stained overnight in Colloidal Coomassie Blue G-250, destained in DI water, and imaged using the GS800 Calibrated Densitometer. An exemplary image of a stained gel is shown in FIG. 1 and the protein bands associated with Gy alleles are indicated to the left of the figure. Quantitation was performed using Bio-Rad Quantity One™ Software. The software was used to determine the relative quantity of each band in the sample lane. The percent acidic glycinin and percent β-conglycinin protein sub-unit bands are reported as the relative percent of the total protein in the lane. The sample identities and weights are tracked using Master LIMS™.

Example 4

Mutations in Gy1 and Gy3

Figure 2:
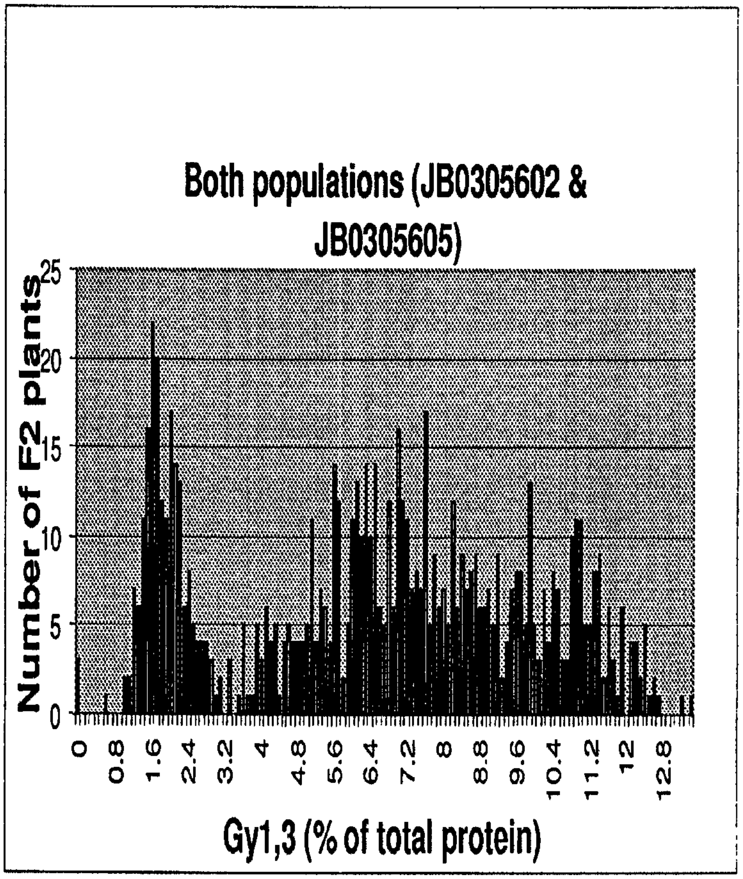
FIG. 2: Progeny plants comprising mutant Gy1 and Gy3 alleles are distributed in two phenotypic groups based Gy1 and Gy3 encoded protein content of seed. Panel A. Graph shows the number of F2 plants (y axis) compared to the percentage of total protein that is constituted by Gy1 and Gy3 encoded acidic proteins (x axis). Panel B. Data from F2 progeny plants indicates that mutant Gy1 and Gy3 alleles, from B2G2 soybeans, are recessive. The number of progeny plants with Gy1 and Gy3 encoded protein levels in the two classes were subjected to chi square analysis and probability values were determined in each case.

F2 progeny plants were analyzed for total content of Gy1 and Gy3 encoded protein. As shown in FIG. 2, the plants were distributed into two phenotypic groups, one group with less than 3% Gy1,3 encoded protein and another with 3.1% greater Gy1,3 encoded protein. Chi square analysis (FIG. 2B) was consistent with the comigrating mutant Gy1 and 3 proteins as recessive traits.

Good sequence coverage was obtained in most parts of the Gy1 gene. Two small gaps exist due to the failures of two primer pairs. The consensus sequence is listed as SEQ ID NO: 163. The allelic scores at some selected nucleotide positions in Gy1 are given in Table 3. There are three SNPs at positions 643, 835 and 839 between JB7/JB8 and other lines. Because no sequence was recovered from B2G2 lines at these positions, it was not determined if the SNPs were inherited from the B2G2 mutant line. No amplicon or sequence at the 5'end of the Gy1 gene were obtained from mutant line B2G2 and its derived lines JB3, JB4, JB13, JB14 and JB15, indicating a possible sequence deletion in the mutant lines. Additional PCR reactions were carried out with the first three pairs of primers and consistent results were obtained. This confirmed the deletion in the mutant lines. The deletion spans the upstream promoter regions, Exon I and Intron I. The junctions of the deletion have not yet been precisely determined. A dominant marker was designed on the deletion for use as diagnostic marker for Gy1 locus.

DNA sequence variations at the Gy3 locus were determined by resequencing of the entire gene on multiples lines. The consensus sequence obtained is listed as SEQ ID NO: 164. Allelic scores of polymorphisms at this locus are given in Table 4. Five SNPs and two INDELs were detected among mutants and wild types. The original mutant line, B2G2, carried an insertion (TGAT) at positions 848-851 while all other lines carried a deletion at this location. B2G2 also carried rare alleles on three SNPs at position 1083, 1120 and 1866 while all other lines carried the abundant allele. None of the B2G2 derived lines used in this study inherited the B2G2 alleles at Gy3 locus.

TABLE 3

| | Position/Allele | | | | | | | | | | |
|---|---|---|---|---|---|---|---|---|---|---|---|
| Lines | 195 | 450 | 600 | 643 | 800 | 835 | 839 | 1000 | 1300 | 2762 | 27703 |
| JB1 | | | C | T | G | A | C | T | C | G | G |
| JB2 | | C | C | T | G | A | C | T | | G | G |
| JB3 | | | | | | | | | | | G |
| JB4 | | | | | | | | | | | |
| JB5 | A | | C | T | | | | | | G | G |
| JB6 | A | C | C | T | G | A | C | T | C | | |
| JB7 | | | C | A | G | T | T | T | | | G |
| JB8 | | | | A | | T | T | | | | |
| JB9 | | | | A | G | A | C | T | | A/G | A/G |
| JB10 | A | C | C | T | G | A | C | T | | G | G |
| JB11 | | | | | | | | | | G | G |
| JB12 | A | | C | T | G | A | | T | | G | G |
| JB13 | | | | | | | | | | G | G |
| JB14 | | | | | | | | | | G | G |
| JB15 | | | | | | | | | | G | G |
| A1923 | | | C | N | G | A | C | T | | G | G |
| A3244 | A | C | C | T | G | A | C | T | C | G | |
| AG2403 | A | C | C | T | G | A | C | T | C | G | G |
| AG2703 | A | C | C | T | G | A | C | T | C | G | G |
| AG3201 | | N | C | T | G | A | C | T | C | | |
| AG3202 | A | C | C | T | G | A | C | T | C | G | G |
| DKB17-51 | | C | C | T | G | A | C | T | C | | |
| DKB19-51 | | C | C | T | G | A | C | T | | G | G |
| B2G2 | | | | | | | | | C | G | G |

TABLE 4

| | Position/Allele | | | | | | | | |
|---|---|---|---|---|---|---|---|---|---|
| Lines | 234 | 1318 | 1600 | 1866 | 2200 | 2504-2505 | 2574 | 2850 | 3189 |
| JB1 | A | A | A | C | A | — | G | | C |
| JB2 | A | A | A | C | A | | | G | C |
| JB3 | A | A | A | C | | — | G | G | |
| JB4 | A | A | A | C | A | | | G | C |
| JB5 | A | A | A | C | A | | | G | C |
| JB6 | A | A | A | C | A | — | G | G | C |
| JB7 | A | A | A | C | A | | | G | C |
| JB8 | A | A | A | C | A | | | G | C |
| JB9 | A | | | | | | | G | C |
| JB10 | A | A | A | C | | | | | |
| JB11 | A | A | A | C | | | | G | |
| JB12 | A | A | A | C | A | | | G | C |
| JB13 | A | A | A | C | A | | | | |
| JB14 | A | A | A | C | | | | G | |
| JB15 | A | A | A | C | | | | G | |
| A1923 | A | A | A | C | | | | G | |
| A3244 | A | A | A | C | A | — | G | | C |
| AG2403 | A | A | A | C | | | | G | |
| AG2703 | A | A | A | C | A | AT | A | G | T |
| AG3201 | A | A | A | C | A | — | G | | |
| AG3202 | A | A | A | C | A | | | G | C |
| DKB17-51 | A | A | A | C | A | — | G | | |
| DKB19-51 | A | A | A | C | A | | | G | T |
| B2G2 | A | | | A | A | | | G | |

Example 5

Mutations in Gy2

Figure 3:
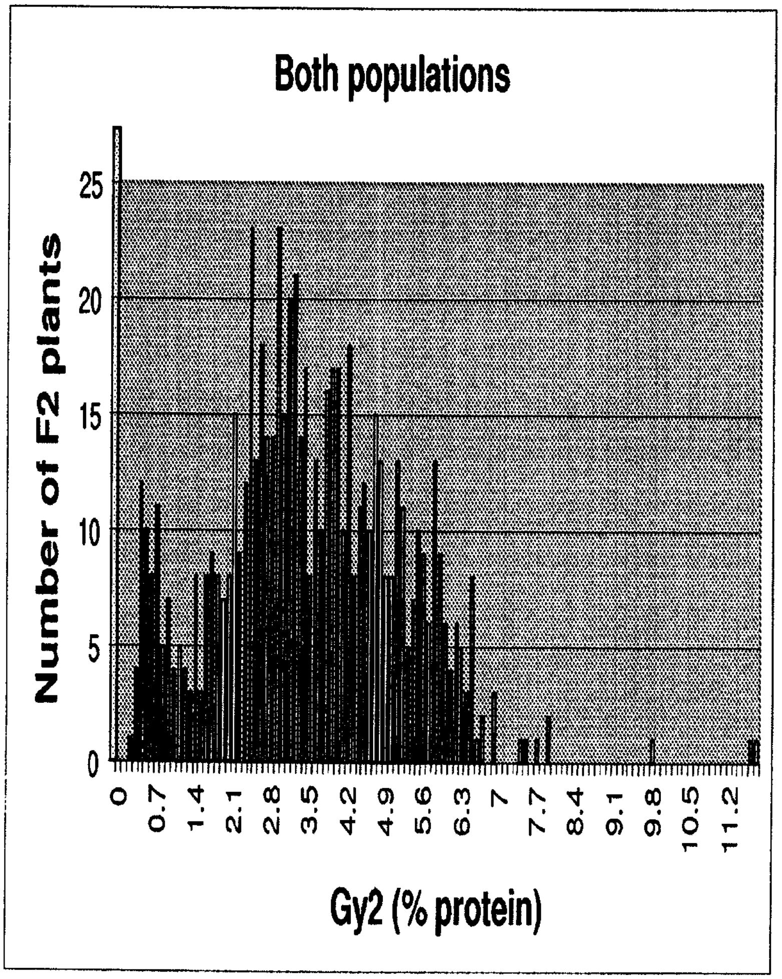
FIG. 3: Progeny of "11S null" plants are distributed into two populations based on the percentage of total protein in the seed that is Gy2. Panel A. Graph shows the number of F2 plants (y axis) compared to the percentage of total protein that is constituted by Gy2 encoded proteins (x axis). Panel B. Data from progeny plants indicates that the mutant Gy2 allele from B2G2 soybeans is recessive. The number of progeny plants with Gy2 encoded protein levels in the two classes were subjected to chi square analysis and probability values were determined in each case.

F2 progeny plants were analyzed for total content of Gy2 encoded protein. As shown in FIG. 3, the plants were distributed into two phenotypic groups, one group with less than 1% Gy2 encoded protein and another with 1.1% or greater Gy2 encoded protein. Chi square analysis (FIG. 3B) was consistent with the reduced Gy2 expression as a recessive trait.

When the expression levels of Gy1,3 and Gy2 subunits were compared (FIG. 4) it was found that expression of the Gy1,3 encoded proteins positively correlated with expression of Gy2 encoded protein, with a correlation coefficient of 0.88, see FIG. 4B. This data indicated that expression of low Gy2 encoded protein levels could be determined based upon the Gy1, and/or Gy3 genotype.

Sequencing of the Gy2 gene indicated only three identifiable SNPs and the rare allele all came from JB7 line. All other lines were identical. Because of high sequence homology among Gy1, Gy2 and Gy3, occasional cross contaminations do occur even with locus specific primers, thus other variations may exist that were not identified.

Example 6

Mutations in Gy4

Figure 5:
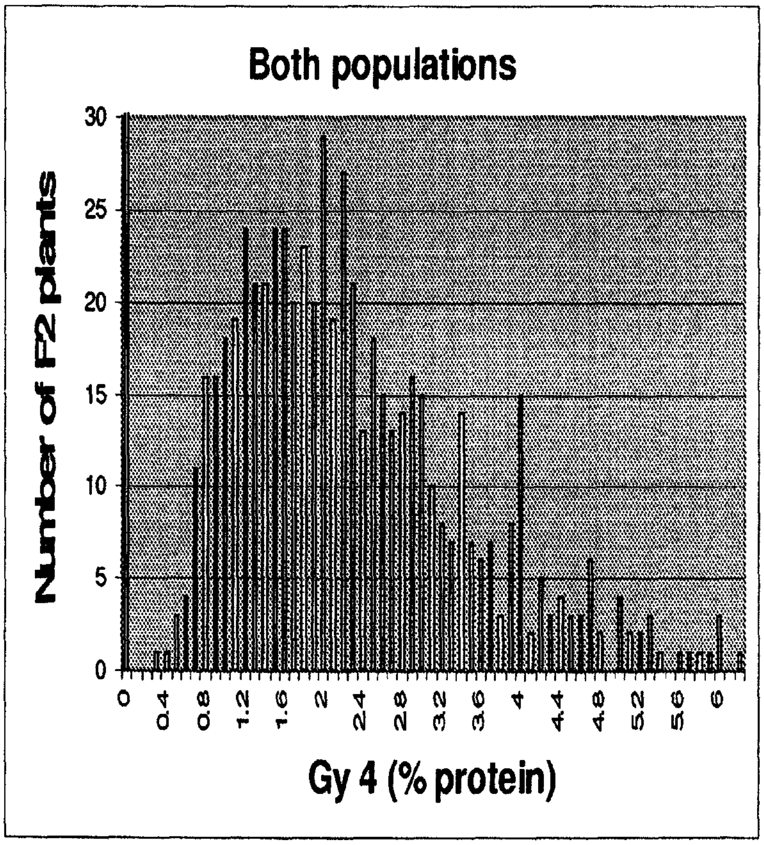
FIG. 5: Progeny of 11S null plants are distributed into two populations based on the percentage of total protein in the seed that is Gy4. Panel A. Graph shows the number of F2 plants (y axis) compared to the percentage of total protein that is constituted by Gy4 encoded acidic protein (x axis). Panel B. Data from progeny plants indicates that the mutant Gy4 allele from B2G2 soybeans is recessive. The number of progeny plants with Gy4 encoded protein levels in the two classes were subjected to chi square analysis and probability values were determined in each case.

Progeny plants were subjected to protein analysis to determine the amount of Gy4 encoded polypeptides that were expressed. As shown in FIG. 5, the plants were distributed in two phenotypic groups, one group that was null for Gy4 and another group that demonstrated expression of Gy4 encoded polypeptides. Chi square analysis (FIG. 5B) was consistent with the Gy4 null allele as a recessive trait.

Sequence analysis of the Gy4 alleles revealed a mutation at the translation initiation codon in mutant line B2G2 and its derived lines (Table 5, position 682, SEQ ID NO:165). The mutation changes ATG to ATA. Since the translation initiation codon was lost, the peptide subunit encoded by this gene is most likely unable to translate. This SNP is ideal for use as molecular marker indicative of Gy4 loss. The sequence obtained was used to design primers for detection of this marker, termed NS0199003 (see Table 8).

Additional polymorphisms at position 1620 and 1632 were also observed in some sequence reads from B2G2 and certain progeny lines, but these did not correlate with the loss of the Gy4 encoded protein subunits. Thus, these inconsistencies may be caused by nonspecific amplification with the primers at this region.

TABLE 5

| | Position/Allele | | |
|---|---|---|---|
| Lines | 682 | 1620 | 1632 |
| JB1 | A | C | T |
| JB2 | A | C | T/C |
| JB3 | A | C | T |
| JB4 | G | C | T |
| JB5 | A | C | T |
| JB6 | G | C | T |
| JB7 | G | C | T |
| JB8 | G | C | T |
| JB9 | A | C | T |
| JB10 | A | C | T/C |
| JB11 | A | C | T |
| JB12 | A | C | T |
| JB13 | A | C | T |
| JB14 | A | C | T |
| JB15 | A | C | T |
| A1923 | G | C | T |
| A3244 | G | C | T |
| AG2403 | G | C | T |
| AG2703 | G | C | T |
| AG3201 | | | |
| AG3202 | G | C | T |
| DKB 17-51 | | | |
| DKB 19-51 | G | C | T |
| B2G2 | A | T/C | T/C |

Example 7

Mutations in Gy5

Sequence analysis of the Gy5 alleles indicated there are two SNPs (positions 363 and 612 on SEQ ID NO: 166) and two INDELs (positions 447-453, 519-524) in B2G2 plants as compared to other parental varieties (Table 6). Additionally, a SNP was identified at position 752 in Exon II which changes the amino acid residue from Serine to Asparagine. All five SNPs or INDELs form into two haplotypes in the lines tested. Mutant line B2G2 and its derived lines JB1, JB5 and JB8 shared one haplotype while others lines shares another haplotype. These SNPs/INDELs appear to be in linkage disequilibrium and are associated with the "11s null" phenotypes. It is still unknown if these SNPs or INDELs actually caused the loss of A3 subunit in B2G2 as shown on FIG. 1. Since these are all sequence variations detected in the coding region there may be some other variations residing in the promoter regions which caused the loss of the A3 band as seen on the protein gel.

TABLE 6

| Lines | Position/Allele 363 | 447-453 | 519-524 | 612 | 752 |
|---|---|---|---|---|---|
| JB1 | C | ******* | ****** | A | A |
| JB2 | G | TTTTTAG | TAATAA | T | G |
| JB3 | G | TTTTTAG | TAATAA | T | G |
| JB4 | G | TTTTTAG | TAATAA | T | G |
| JB5 | C | ******* | ******* | A | A |
| JB6 | | | | | |
| JB7 | G | TTTTTAG | TAATAA | T | G |
| JB8 | C | ******* | ******* | A | A |
| JB9 | G | TTTTTAG | TAATAA | T | G |
| JB10 | G | TTTTTAG | TAATAA | T | G |
| JB11 | G | TTTTTAG | TAATAA | T | G |
| JB12 | | | | | |
| JB13 | G | TTTTTAG | TAATAA | T | G |
| JB14 | G | TTTTTAG | TAATAA | T | G |
| JB15 | G | TTTTTAG | TAATAA | T | G |
| A1923 | G | TTTTTAG | TAATAA | T | |

TABLE 6-continued

| Lines | Position/Allele 363 | 447-453 | 519-524 | 612 | 752 |
|---|---|---|---|---|---|
| A3244 | G | TTTTTAG | TAATAA | T | G |
| AG2403 | G | TTTTTAG | TAATAA | T | G |
| AG2703 | | | | | |
| AG3201 | G | TTTTTAG | TAATAA | T | G |
| AG3202 | G | TTTTTAG | TAATAA | T | G |
| DKB17-51 | G | TTTTTAG | TAATAA | T | G |
| DKB19-51 | G | TTTTTAG | TAATAA | T | G |
| B2G2 | C | ******* | ******* | A | A |

Example 8

Development of Gy Mutation Markers

PCR analyses, such as Taqman® assays, were designed for the SNPs or INDELs identified above. Table 7 lists the primer and probe sequences of each assay as well as the marker name assigned to each marker. Two assays were designed for Gy1 and Gy3 respectively using SNPs at different positions. These assays were first run on the standard panel used in resequencing in this study and then used in segregating populations.

TABLE 7

| Gene | Marker Name | Assays | Description | Sequence |
|---|---|---|---|---|
| Gy1 | NS0199008 | GY1_conA-644 | Forward Primer | SEQ ID NO: 129 AATAACCACGCCTCAGGTTCTC |
| Gy1 | NS0199008 | GY1_conA-644 | Reverse Primer | SEQ ID NO: 130 GAGTGTTTAAGGACCAATGGAGAG A |
| Gy1 | NS0199008 | GY1_conA-644 | Vic Probe | SEQ ID NO: 131 CTTCACAACTCAAACAT |
| Gy1 | NS0199008 | GY1_conA-644 | FAM Probe | SEQ ID NO: 132 TTCACAACACAAACAT |
| Gy1 | NS0199009 | GY1_conB-839 | Forward Primer | SEQ ID NO: 133 CCCTCAAACCGGATAACCGTATAG |
| Gy1 | NS0199009 | GY1_conB-839 | Reverse Primer | SEQ ID NO: 134 CACTGGAATGGCTTGTTGTTAGG |
| Gy1 | NS0199009 | GY1_conB-839 | Vic Probe | SEQ ID NO: 135 ATGTCTCAATGAGCCC |
| Gy1 | NS0199009 | GY1_conB-839 | FAM Probe | SEQ ID NO: 136 ATGTCTCAATGAACCC |
| Gy2 | NS0199002 | GY2-102 | Forward Primer | SEQ ID NO: 137 CGTACATCATACATGTTATAAATT AAGCTCAACAA |
| Gy2 | NS0199002 | GY2-102 | Reverse Primer | SEQ ID NO: 138 GCATATGCAAGTGCTAAGATAACT TTGT |
| Gy2 | NS0199002 | GY2-102 | Vic Probe | SEQ ID NO: 139 ACACATTTTAATTACTATATATAA CT |

TABLE 7-continued

| Gene | Marker Name | Assays | Description | Sequence |
|---|---|---|---|---|
| Gy2 | NS0199002 | GY2-102 | FAM Probe | SEQ ID NO: 140 CACATTTTAATTACTATATATAGCT |
| Gy3 | NS0199004 | GY3-89 | Forward Primer | SEQ ID NO: 141 AGAGCCCTTTTTGCATGTGCTA |
| Gy3 | NS0199004 | GY3-89 | Reverse Primer | SEQ ID NO: 142 TCGTTCTTATTTATTGCTACGCACA CT |
| Gy3 | NS0199004 | GY3-89 | Vic Probe | SEQ ID NO: 143 CAAAAGGACAAAAGTGT |
| Gy3 | NS0199004 | GY3-89 | FAM Probe | SEQ ID NO: 144 AAAAGGACGAAAGTGT |
| Gy3 | NS0199010 | GY3_conA-1866 | Forward Primer | SEQ ID NO: 145 GGAACCAAGAGCAAGAGTTTCTAC A |
| Gy3 | NS0199010 | GY3_conA-1866 | Reverse Primer | SEQ ID NO: 146 CGCTTTCCTTTCTGGCTTTGAGTA |
| Gy3 | NS0199010 | GY3_conA-1866 | Vic Probe | SEQ ID NO: 147 CTCCTTGCTGCTTCT |
| Gy3 | NS0199010 | GY3_conA-1866 | FAM Probe | SEQ ID NO: 148 CCTCCTTTCTGCTTCT |
| Gy4 | NS0199003 | GY4-93 | Forward Primer | SEQ ID NO: 149 TCCAATTCACCAACTCCTTCAAAC T |
| Gy4 | NS0199003 | GY4-93 | Reverse Primer | SEQ ID NO: 150 CAAAGGGAAGAAAGAGAGAGAGT GA |
| Gy4 | NS0199003 | GY4-93 | Vic Probe | SEQ ID NO: 151 CTTCCTTAGTTCAATATAGG |
| Gy4 | NS0199003 | GY4-93 | FAM Probe | SEQ ID NO: 152 TCCTTAGTTCAATATGGG |
| Gy7 | NS0199001 | GY7-72 | Forward Primer | SEQ ID NO: 153 CATAGGAGAACACGAGGGATGTG |
| Gy7 | NS0199001 | GY7-72 | Reverse Primer | SEQ ID NO: 154 GGCTTCTACTTTGCTCTTCCTCTT |
| Gy7 | NS0199001 | GY7-72 | Vic Probe | SEQ ID NO: 155 AATGCGAAGATAAAG |
| Gy7 | NS0199001 | GY7-72 | FAM Probe | SEQ ID NO: 156 ATGCGAAAATAAAG |

Example 9

High Correspondence Between Gy Markers and Protein Subunits

Figure 6:
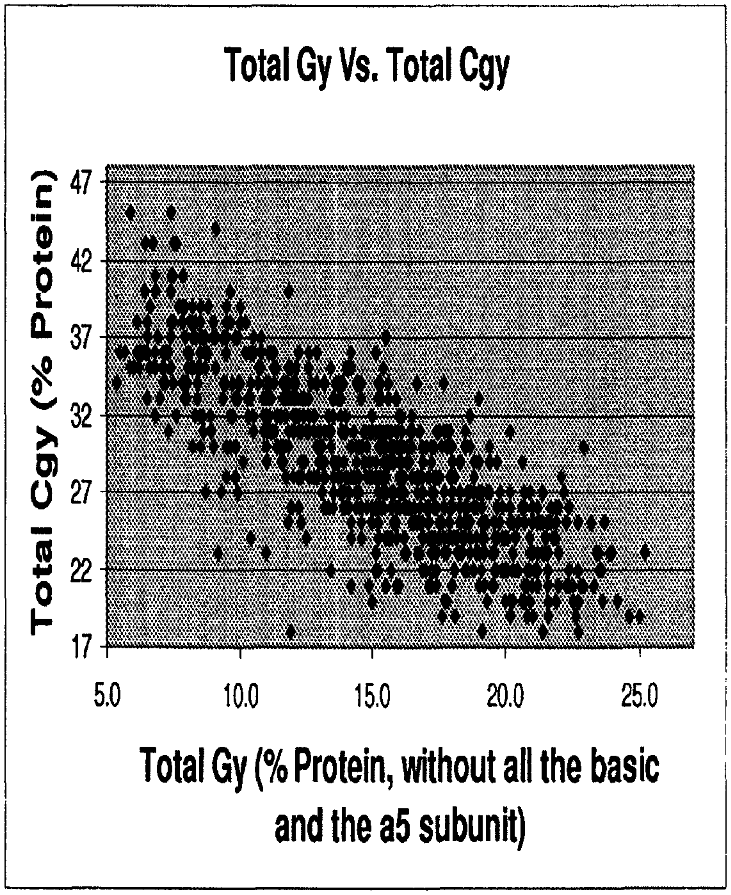
FIG. 6: Decreased expression of glycinin in soybean seed correlates with increased expression of β-conglycinin. Panel A. Graph plots the percentage of total protein encoded by Gy alleles (x axis) versus the percentage of total protein encoded by Cgy alleles (y axis). Panel B. Table shows the correlation coefficients between expression of Gy encoded proteins and the expression of Cgy1-4 encoded proteins.

F1 progeny plants were analyzed to determine total content of the glycinin and beta-conglycinin protein. The graph in FIG. 6A shows total glycinin protein versus total beta-conglycinin protein for each plant. The data indicates that lower expression of glycinin correlates with higher expression of beta-conglycinin (Cgy) subunits (FIG. 6B).

Genetic correlation between molecular markers and their corresponding glycinin subunits was carried out in two F2 segregating populations, JB0305602 and JB0305605. To establish which genetic markers were indicative of the mutant Gy alleles, all the individuals of the two populations were analyzed for protein content on SDS-PAGE and genotyped with SNP markers developed in this study together with a number of markers selected throughout the genome. As indicated above and in FIG. 1, protein bands for Gy1 and Gy3 were clustered together and thus they were measured as one unit. Table 8 shows that segregation of protein bands, expressed as percentage of total protein, is highly correlated with the SNP markers. For example, plants with the mutant allele at Gy1 always contain lower glycinin A1 and A2 subunits, 2.5 and 2.4%, respectively in both populations while those with "TT" allele contain higher glycinin A1 and A2 subunits, 7.6 and 8.1% respectively. The correlation is highly significant (P-values of $1.7\times10^{-55}$ and $4.1\times10^{-62}$ respectively) and a similar correlation was observed in the case of Gy2. At the Gy4 locus, individuals carrying "AA" alleles contain lower glycinin subunits A5A4B3, 0.6% and 0.1% in their respective populations, while heterozygotes ("AG") contain 1.8% in both populations and those with "GG" contain highest glycinin subunits A5A4B3, 2.9% and 3.3% in their respective populations. The correlation is highly significant, with P-values of $2.3\times10^{-40}$ and $2.3\times10^{-69}$ respectively. Data indicated that the NS0199008, NS0199002 and NS0199003 marker in particular correlated well with reduced expression of indicated glycinin subunits, and could be used to predict a reduced glycinin phenotype.

TABLE 8

| Population | Gene | Marker Name | Allele | Protein Mean (%) | #of F2 Plants | DF | ProbF | Rsquare |
|---|---|---|---|---|---|---|---|---|
| JB0305605 | Gy1 | NS0199008 | ** | 2.5 | 103 | 1 | 1.70E−55 | 0.49 |
| | Gy1 | NS0199008 | TT | 7.6 | 269 | 1 | | |
| | Gy2 | NS0199002 | ** | 2.8 | 109 | 1 | 1.00E−49 | 0.45 |
| | Gy2 | NS0199002 | TT | 7.6 | 263 | | | |
| JB0305602 | Gy1 | NS0199008 | ** | 2.4 | 89 | 1 | 4.10E−62 | 0.49 |
| | Gy1 | NS0199008 | TT | 8.1 | 283 | 1 | | |
| | Gy2 | NS0199002 | ** | 3 | 102 | 1 | 2.70E−54 | 0.48 |
| | Gy2 | NS0199002 | TT | 8.1 | 270 | | | |
| JB0305605 | Gy4 | NS0199003 | AA | 0.6 | 112 | 2 | 2.30E−40 | 0.43 |
| | Gy4 | NS0199003 | AG | 1.8 | 128 | | | |
| | Gy4 | NS0199003 | GG | 2.9 | 92 | | | |
| JB0305602 | Gy4 | NS0199003 | AA | 0.1 | 93 | 2 | 2.30E−69 | 0.62 |
| | Gy4 | NS0199003 | AG | 1.8 | 149 | | | |
| | Gy4 | NS0199003 | GG | 3.3 | 88 | | | |

Example 10

Variation in Protein Expression in Gy2 and Gy4 Null Soybean Plants

Agronomically elite soybean plants comprising non-transgenic mutations conferring a null Gy2 and Gy4 phenotype and a reduced Gy1/Gy3 phenotype were analyzed for total content of various glycinin and β-conglycinin subunits. Three distinct lines, Pedigree 1 (AH_DAK2301A1RMA3244/(B2G2/A1923:.077.):0001.0097.0015.)/DJW2500C0R: @.0013.):@.0114.0008.@); Pedigree 2 (AH_DAK2301A1RMA3244/(B2G2/A1923:.077.):0001.0097.0015.)/DJW2500C0R: @.0013.):@.0096.0007.@); and Pedigree 3 (AH_DAK2301A1RMA3244/(B2G2/A1923:.077.):0001.0097.0015.)/DJW2500C0R: @.0013.):@.0105.0006.@) (deposited as ATCC Accession No. PTA-6892) were studied and data for each is presented in Tables 9, 10 and 11 respectively.

In the case of each line, plants grown in various locations, during the 2004-2005 season were analyzed. Data presented in these tables indicates the total content of Gy1/Gy3, Gy5, α' BC, α BC and β BC protein subunits as a percentage of the total seed protein content. Also indicated is the total content of acidic glycinin subunits and total β-conglycinin content. For each of the three pedigrees the average data (Avg.) and standard deviation from the mean (St. Dev.) is indicated in the last two rows of each table. Values were calculated using the methods described above, in Example 3. In no case was detectable Gy2 or Gy4 encoded protein observed.

The studies outlined in Tables 9-11 indicated that the content of various glycinin and beta-conglycinin protein subunits was variable both between the three plant lines tested (e.g. effects from differing genomic backgrounds) and in plants grown in different environments conditions (at different locations). These data highlight the advantage of selection of Gy mutant plants by the use polymorphism markers, since detection of these markers will not be subject to variability based on genomic background and environmental conditions.

TABLE 9

| Pedigree | Gy1,3 | Gy5 | α' BC | α BC | β BC | Acidic Glycinins | β-Conglycinins |
|---|---|---|---|---|---|---|---|
| 1 | 1.98 | 4.36 | 12.300 | 15.630 | 7.00 | 6.34 | 34.93 |
| 1 | 2.46 | 6.83 | 12.276 | 14.274 | 9.91 | 9.29 | 36.46 |
| 1 | 3.01 | 6.12 | 12.375 | 16.158 | 7.19 | 9.13 | 35.72 |
| 1 | 2.98 | 6.69 | 12.63 | 16.731 | 6.79 | 9.67 | 36.15 |
| 1 | 2.35 | 4.94 | 12.693 | 15.393 | 4.94 | 7.29 | 33.03 |
| 1 | 2.48 | 4.97 | 11.906 | 14.579 | 9.06 | 7.45 | 35.55 |
| Avg. 1 | 2.54 | 5.65 | 12.36 | 15.46 | 7.48 | 8.20 | 35.31 |
| St. Dev.1 | 0.39 | 1.03 | 0.28 | 0.93 | 1.77 | 1.35 | 1.23 |

TABLE 10

| Pedigree | Gy1,3 | Gy5 | α' BC | α BC | β BC | Acidic Glycinins | β-Conglycinins |
|---|---|---|---|---|---|---|---|
| 2 | 1.69 | 5.31 | 13.301 | 18.618 | 6.01 | 7.00 | 37.93 |
| 2 | 2.33 | 5.72 | 13.351 | 16.495 | 6.98 | 8.05 | 36.83 |
| 2 | 2.21 | 5.44 | 11.661 | 18.332 | 8.47 | 7.65 | 38.46 |
| 2 | 2.32 | 5.61 | 13.194 | 18.020 | 7.28 | 7.93 | 38.49 |
| 2 | 2.22 | 6.43 | 14.027 | 18.156 | 6.14 | 8.65 | 38.32 |

TABLE 10-continued

| Pedigree | Gy1,3 | Gy5 | α' BC | α BC | β BC | Acidic Glycinins | β-Conglycinins |
|---|---|---|---|---|---|---|---|
| 2 | 1.93 | 5.92 | 12.711 | 18.036 | 9.62 | 7.85 | 40.37 |
| Avg. 2 | 2.12 | 5.74 | 13.04 | 17.94 | 7.42 | 7.86 | 38.40 |
| St. Dev.2 | 0.25 | 0.40 | 0.80 | 0.74 | 1.40 | 0.54 | 1.15 |

TABLE 11

| Pedigree | Gy1,3 | Gy5 | α' BC | α BC | β BC | Acidic Glycinins | β-Conglycinins |
|---|---|---|---|---|---|---|---|
| 3 | 2.70 | 5.73 | 14.090 | 19.802 | 6.63 | 8.43 | 40.52 |
| 3 | 1.90 | 4.45 | 15.315 | 21.201 | 6.08 | 6.35 | 42.60 |
| 3 | 2.33 | 5.94 | 14.608 | 20.974 | 8.63 | 8.27 | 44.21 |
| 3 | 2.66 | 5.40 | 12.277 | 18.842 | 8.12 | 8.06 | 39.24 |
| 3 | 2.91 | 6.96 | 14.863 | 20.699 | 5.40 | 9.87 | 40.96 |
| 3 | 1.77 | 5.73 | 13.303 | 17.909 | 8.65 | 7.50 | 39.86 |
| Avg. 3 | 2.38 | 5.70 | 14.08 | 19.90 | 7.25 | 8.08 | 41.23 |
| St. Dev.3 | 0.46 | 0.81 | 1.12 | 1.31 | 1.40 | 1.16 | 1.85 |

Example 11

Gy Genomic Markers can be Used to Select Low Glycinin Soybean Plants

Segregation of Gy1 (NS0199008), Gy2 (NS0199002) and Gy4 (NS0199003) markers was analyzed on two F2 populations. As shown in Table 9, both Gy1 and Gy3 are dominant markers, and each segregates in a 3:1 ratio. Gy4 is a co-dominant marker.

Figure 7:
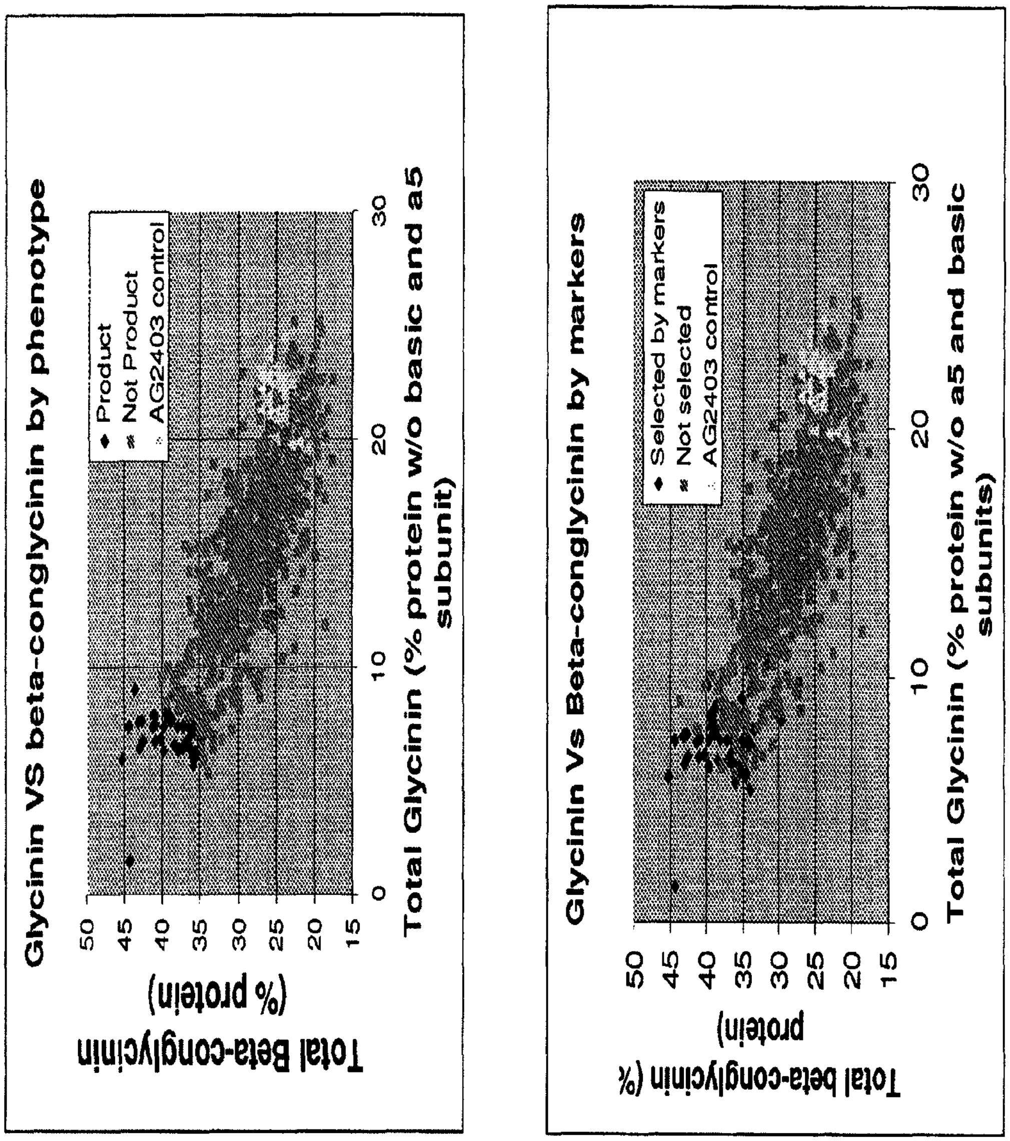
FIG. 7: Genomic Gy markers effectively selected conventional plants that produce seed with high β-conglycinin expression. Panel A. Graph plots total β-conglycinin protein content of seed (y axis) versus total seed glycinin content (x axis). Diamonds indicate plants selected by protein analysis of glycinin subunits. Panel B. Graph is the same as in FIG. 7, Panel A, however diamonds indicate plants selected by markers NS0199002, NS0199003, and NS0199008.

The three identified markers can be used to identify plants with low glycinin and high β-conglycinin seed content. FIG. 7 illustrates the glycinin and β-conglycinin content of F2 plants. Plants were selected based on either protein analysis of subunit expression (FIG. 7A) or using the three mutant Gy markers (FIG. 7B). The data shows that the selection based on markers misidentified less than 1% (7/754) F2 plants.

Example 12

Color Analysis of Soybean Seeds of Low Glycinin Soybean Plants Produced

Green seed color is often viewed as less desirable by soybean farmers and consumers. Eliminating the green seed color of a line would therefore be desirable. An analysis was carried out on low glycinin soybeans produced as described herein to analyze the extent to which the green seed color was eliminated. Color analysis was carried out on whole soybeans using the ColorFlex Reflectance Spectrophotometer (Model 45/0). The spectrometer was standardized using black glass and white tile. The standardization was checked using a green tile having color values certified by the manufacturer, Hunter Associates Laboratory, Inc. (Reston, Va., USA).

The spectrophotometer measures the CIE Tristimulus Color Scale Values X, Y and Z and from these values and calculates the CIELAB Color Scale Values L*, a* and b*. The CIELAB Color Scale allows the specification of color perception in terms of three-dimensional space (CIE, Colorimetry, Publication 15.2, Second Edition, Vienna, 1986), with a CIELAB Color Space organized in a cube. The L*-axis runs from top to bottom and is known as the lightness value, which extends from 0 (black) to 100 (white). The a* and the b*axes have no specific numerical limits. The coordinate a* represents redness when positive, gray when zero and greenness when negative. The coordinate b* represents yellowness when positive, gray when zero and blueness when negative.

A multi-layer of whole soybeans filled the 35×10 mm style polystyrene tissue culture dish with the lid on the bottom of the dish in order to protect the reading surface. The lid was removed from the bottom of the tissue culture dish before it was placed on the spectrophotometer port. The tissue culture dish with the whole soybeans was placed on the spectrometer port with the side to be measured towards the port. The light trap was placed over the sample in order to restrict any external light interference.

The CIE Tristimulus Color Scale screen was displayed on the ColorFlex. The Read Key was pressed and the CIE Tristimulus Color Scale Values were measured for the whole soybean sample. The color capture program recorded the values into an Excel spread-sheet. The view was toggled to the CIELAB Color Scale screen, the Read Key was pressed, and the spectrophotometer was used used to calculate the CIELAB Color Scale Values L*, a* and b* for the whole soybean sample.

Five replicates of whole soybeans in a multi-layer arrangement were measured for each sample. The same whole soybeans were repacked four times in order to achieve five color measurements. The results of the color analysis can be summarized in Table 12 as follows.

TABLE 12

| | | a* | stdev | L* | stdev |
|---|---|---|---|---|---|
| Commercial control (AG1901) | Commercial control (Agl901) | 7.08 | 0.3 | 54.55 | 1 |
| B2G2 | B2G2 | 1.91 | 0.28 | 51.65 | 1.34 |
| JB5 | HBC Line segregating for color | 3.73 | 0.59 | 53.65 | 0.76 |
| AJB2002K0C (A3244/ (B2G2/A1923: .077.)) | HBC line retaining some off-color | 7.36 | 0.25 | 52.39 | 1.69 |
| Pedigree 3 | Elite HBC variety | 7.34 | 0.2 | 57.66 | 0.84 |

Elite = a* > 5 and L* > 54

Example 13

Sequence Variations in Lipoxygenase Genes

The Lox2 sequence from GenBank, GI505137, was used as a query to blast against a Monsanto sequence database. Sixty high hits were downloaded and assembled using the SeqMan program (DNASTAR, INC, Madison, Wis.). Two distinct transcripts were identified in the Monsanto DNA sequence collection. One of the transcripts corresponded to a lipoxygenase-1 (Lox1) gene in GenBank and was thus named lx1 (SEQ ID NO:157), and the other corresponded to the Lox2 (lx2) gene (SEQ ID NO:158). Gene-specific primers were designed and used to generate amplicons from a panel of eight lines. The panel consisted of six mutants and two wild types. Table 13 lists the lines used in the sequencing panel.

TABLE 13

| Pos | Variety | Pedigree | Alleles |
|---|---|---|---|
| A | PI86023 | | lx2lx2 |
| B | L2-3 (aka PI561405) | Century x PI86023 | lx2lx2 |
| C | IA2025 | | lx1lx1lx2lx2lx3lx3 |
| D | IA2032 | | lx1lx1lx2lx2lx3lx3 |
| E | PI408251 | | lx1lx1Lx2Lx2Lx3Lx3 |
| F | PI417458 | | LX1LX1LX2LX2LX3LX3 |
| G | A3469 | | LX2LX2 |
| H | A2247 | | LX2LX2 |

Amplicon sequencing revealed that there were 27 polymorphisms among eight lines on the Lox1 locus, including 21 SNPs and 6 INDELs (Table 14). Out of these polymorphisms, 10 were located in exons. Based on the allelic scores at all these polymorphisms, eight lines in the sequence panel fall into six haplotypes. Both wild types A3469 and A2247 belong to the same haplotype while other mutants are of different haplotypes. A 74 bp deletion was detected in IA2025, IA2032 and PI408251. The deletion appears to be associated with lx1 mutant phenotypes (Table 13).

TABLE 14

| | | EX | INT | INT | INT | INT | EX | INT | INT | INT | INT | EX | INT | INT |
|---|---|---|---|---|---|---|---|---|---|---|---|---|---|---|
| Variety | Haplo | 178-180 | 326 | 363 | 380 | 713 | 1196 | 1253 | 1372 | 1388 | 1527 | 1554 | 2267 | 3055] |
| PI86023 | | — | — | — | — | — | A | T | T | T | A | A | G | C |
| L2-3 | Hap2 | GCG | * | C | A | A | A | T | T | T | A | A | G | C |
| IA2025 | Hap5 | *** | A | T | * | G | A | T | T | T | A | A | C | A |
| IA2032 | Hap6 | GCG | * | C | A | A | A | T | T | T | A | A | C | A |
| PI408251 | Hap4 | *** | A | T | * | G | A | T | T | T | A | A | C | A |
| PI417458 | Hap1 | GCG | * | C | A | A | T | A | G | C | T | C | C | A |
| A3469 | Hap3 | *** | A | T | * | G | T | A | G | C | T | C | C | A |
| A2247 | Hap3 | *** | A | T | * | G | T | A | G | C | T | C | C | A |

| | | | | INT | EX | INT | EX | INT | INT | EX | EX | EX | EX | EX | EX |
|---|---|---|---|---|---|---|---|---|---|---|---|---|---|---|---|
| Variety | Haplo | 3088 | 3125 | 3139 | 3204 | 3278 | 3832-3905 | 4043 | 4057 | 4193 | 4225 | 4247 | 4267 | 4430 | 4439 |
| PI86023 | | T | * | T | C | C | GATC# | A | * | C | T | A | C | A | G |
| L2-3 | Hap2 | T | * | T | C | C | GATC | A | * | C | T | A | C | A | G |
| IA2025 | Hap5 | G | G | A | G | A | **** | C | A | G | C | G | T | C | A |
| IA2032 | Hap6 | G | G | A | G | A | **** | C | A | G | C | G | T | C | A |
| PI408251 | Hap4 | G | G | A | G | A | **** | C | A | G | C | G | T | C | A |
| PI417458 | Hap1 | G | G | A | G | A | GATC | C | A | G | C | G | T | C | A |
| A3469 | Hap3 | G | G | A | G | A | GATC | C | A | G | C | G | T | C | A |
| A2247 | Hap3 | G | G | A | G | A | GATC | C | A | G | C | G | T | C | A |

Note: #GATC represents the 74 bp sequence deleted in IA2025, IA2032, and PI408251.

Polymorphisms at the Lox2 locus are shown on Table 15. Six SNPs and a 2 bp INDEL were detected and two distinct haplotypes are formed in these eight lines. The haplotypes are clearly associated with lx2 phenotypes (Table 13). All of these polymorphisms except the one at position 2542 are located in introns. The SNP at position 2542 is a missense mutation, causing a change in genetic codon from CAT encoding for Histidine to CAA encoding for Glutamine.

TABLE 15

| Variety | Haplotype | 323 | 439 | 139 | 143 | 1458 | 2486-87 | 254 |
|---|---|---|---|---|---|---|---|---|
| PI86023 | | C | A | A | C | G | ** | A |
| L2-3 | Hap1 | C | A | A | C | G | ** | A |
| IA2025 | Hap1 | C | A | A | C | G | ** | A |
| IA2032 | Hap1 | C | A | A | C | G | ** | A |
| PI408251 | Hap2 | T | G | G | T | T | AT | T |
| PI417458 | Hap2 | T | G | G | T | T | AT | T |
| A3469 | Hap2 | T | G | G | T | T | AT | T |
| A2247 | Hap2 | T | G | G | T | T | AT | T |

Figure 8:
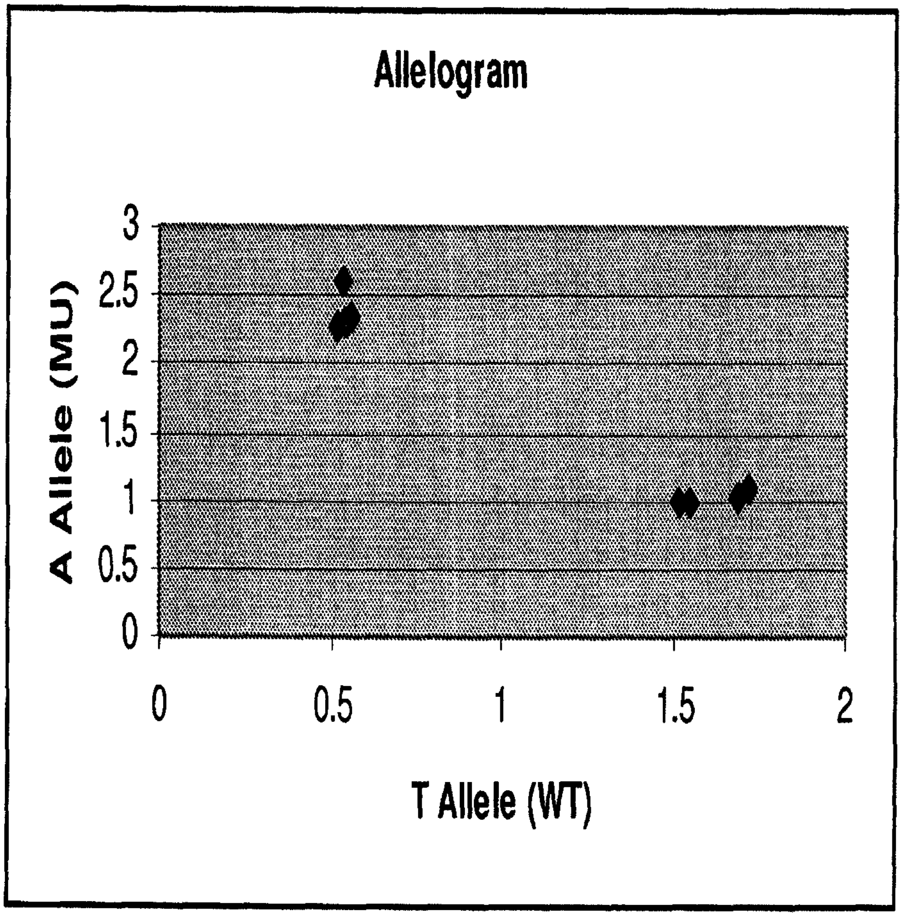
FIG. 8: Allelogram for the Taqman assay designed for the SNP at position 2542 (Marker NS0203296).

A Taqman assay was designed from the SNP at position 2542. The assay information is given in Table 16. The allelogram of this assay is shown on FIG. 8. This marker allowed a clear distinction between the "A" allele from the mutant at Lox2 and the "T" allele from wild type.

TABLE 16

| | |
|---|---|
| Marker | NS0203296 |
| Gene | Lox2 |
| SNP | 203296 |
| AssayID | 1915582-19230-203296 |
| Fwd Primer | GCTATCATCAACTCATGAGCCATTG (SEQ ID NO: 159) |
| Rev Primer | GTGTCGGTTTGTTGCTATGATGAAT (SEQ ID NO: 160) |
| VicProbe | CAATCACCGCTTGAGTAT (SEQ ID NO: 161) |
| VicAllele | A |
| FamProbe | AATCACCGCATGAGTAT (SEQ ID NO: 162) |
| FamAllele | T |

Example 14

Sequence Variations Associated with Kunitz Trypsin Inhibitor Null Phenotype in Soybeans Candidate sequences encoding the Kunitz Trypsin Inhibitor Protein (KTI) of soybean were identified from four candidate sequences encoding KTI in soybeans. One candidate sequence, KTIA (SEQ ID NO:167) was utilized as a template to design primers for subsequent PCR amplification reactions. Locus specific primers were designed from the candidate sequence, and PCR amplicons were generated from 5 KTI-null mutant lines and 7 wild-type lines (Table 17). Alignment of sequences from these amplicons allowed identification of nucleotide variations that are associated with the Kunitz phenotypes (FIG. 9). A 2-bp deletion at position 622-623 and one base mutation at position 624 (see FIG. 9) were detected in all Kunitz null mutants while a "GAG" was present in all the wild types in the same positions. The deletion/insertion is a nonsense mutation, causing the protein to terminate prematurely, explaining the phenotype of the mutant lines, which display the Kunitz null phenotype. This INDEL can be used as a genetic marker for marker-assisted selections for Kunitz null soybean lines and varieties.

TABLE 17

| Line | Genotypes |
|---|---|
| PI542044 | Titi |
| PI157440 | Titi |
| IS206-17 | Titi |
| PI547656 | Titi |
| PI547816 | Titi |
| PI518671 | TiTi |
| A3935 | TiTi |
| DKB19-15 | TiTi |
| AG2703 | TiTi |
| AG3302 | TiTi |
| AG2403 | TiTi |

A PCR-based TAQMAN marker-assisted assay employing primers (e.g. SEQ ID NOs: 168-171) was utilized to allow identification of the KTI-null trait (Table 18), and validation of the assay showed that the KTI-null marker segregated with the KTI-null phenotype.

TABLE 18

| KTI Assay information. Marker Name: NS0201535 | | |
|---|---|---|
| Primer1 | 32_1-1F | GAGAACAAAGATGCAATGGATGGTT (SEQ ID NO: 168) |
| Primer2 | 32_1-1R | GCTGTGGACAGAACACAAGCTTATA (SEQ ID NO: 169) |
| Vic_probe | 32_1-1V2 | AGAAACTCTCTCAAGTCT (SEQ ID NO: 170) |
| FAM_probe | 32_1-1M2 | CATCAGAAACTCTAAGTCT (SEQ ID NO: 171) |
| KTI_Null | | *** |
| Wild Type | | GAG |

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,992,375
U.S. Pat. No. 5,015,580
U.S. Pat. No. 5,024,944
U.S. Pat. No. 5,416,011
U.S. Pat. No. 5,545,545
U.S. Pat. No. 5,604,099
U.S. Pat. No. 5,637,785
U.S. Pat. No. 6,031,154
U.S. Pat. No. 6,140,085
U.S. Pat. No. 6,184,440
U.S. Pat. No. 6,486,383
U.S. Pat. No. 6,774,284
Adams et al., *J. Nutr.,* 134(3):511-516, 2004.
Allard, In: *Principles of Plant Breeding*, John Wiley & Sons, NY, 50-98, 1960.
Baba et al., *J. Nutr. Sci. Vitaminol.* (Tokyo), 50(1):26-31, 2004.
Beachy et al., *Ann. rev. Phytopathol.* 28:451 (1990
Beilinson et al., *Theor. Appl. Genet.,* 104(6-7):1132-1140, 2002.
Boerma and Moradshahi, *Crop Sci.,* 15:858-861, 1975.
Borthwick and Parker, *Bot. Gaz.,* 100:374-387, 1938.
Brim and Stuber, *Crop Sci.,* 13:528-530, 1973.
Charest et al., *Plant Cell Rep.* 8:643 (1990
Chen and Shoemaker, *J. Hered.,* 89:211-215, 1998.
Chrispeels et al., *J. Cell Biol.,* 93:306-313, 1982.
Christianson et al., *Science,* 222:632-634, 1983.
Comai et al., *Nature* 317:741-744 (1985)
Criswell and Hume, *Crop Sci.,* 12:657-660, 1972.
de Moraes et al., *Euphytica* 149:221-226, 2006.
Diers et al., *Theor. Appl. Genet.,* 89:297-304, 1993.
Duranti et al., *J. Nutr.,* 134(6):1334-1339, 2004.
Dutton and Sommer, *Biotechniques,* 11(6):700-7002, 1991.
Eichholtz et al., *Somatic Cell Mol. Genet.* 13:67 (1987)
Elliot et al., *Plant Molec. Biol.* 21:515 (1993
European Appln. 0 242 246
European Appln. 0640141
European Appln. 0797673
Fehr, In: *Theory and Technique, and Crop Species Soybean*, Iowa State Univ., Macmillian Pub. Co., NY, (1)(2):360-376, 1987b.
Fehr, In: Soybeans: Improvement, Production and Uses, 2nd Edition, Manograph., 16:249, 1987a.
Fehr, In: *Hybridization of Crop Plants*, Fehr and Hadley (Eds.), *Am. Soc. Agron. and Crop Sci. Soc. Am.*, Madison, Wis., 90-599, 1980.
Finer et al., In: *Soybean: Genetics, Molecular Biology and Biotechnology*, CAB Intl., Verma and Shoemaker (ed), Wallingford, Oxon, UK, 250-251, 1996.
Fisher et al., *Plant Physiol.,* 102(3):1045-1046, 1993.
Fraley et al., *Proc. Natl. Acad. Sci. USA,* 80:4803, 1983.
Geiser et al., *Gene,* 48:109, 1986.
Gordon-Kamm et al., *Plant Cell,* 2:603-618, 1990.
Hajika et al, *Jpn. J. Breed.,* 42:787-792, 1992.
Hamner, In: *The Induction of Flowering: Some Case Histories*, Evans (ed), Cornell Univ. Press, Ithaca, N.Y., 62-89, 1969.
Harada et al., *Japan J. Breed.,* 33:23-30, 1983.
Hartweck et al., In *Vitro Cell. Develop. Bio.,* 24:821-828, 1988.
Hildebrand et al., *Crop Sci.,* 22:851-853, 1982.
Jones et al., *Science,* 266:789, 1994.
Kitamura et al, *Jpn. J. Breed.,* 35:413-420, 1985.
Kitamura, *Agric. Biol. Chem.,* 27:234-239, 1984.
Knutzon et al., *Proc. Natl. Acad. Sci. USA,* 89:2624, 1992.
Ladin et al., *Plant Physil.,* 84:35-41, 1987.
Lander and Botstein, *Genetics,* 121(1):185-199, 1989.
Lee et al., *EMBO J.,* 7:1241, 1988.
Livak et al., *Nat. Gen.,* 9:341-342, 1995.
Logemann et al., *Bio/Technology,* 10:305, 1992.
Marshall et al., *Theor. Appl. Genet.,* 83:435, 1992.
Martin et al., *Science,* 262:1432, 1993.
Miki et al., *Theor. Appl. Genet.,* 80:449, 1990.
Mindrinos et al., *Cell,* 78:1089, 1994.
Moriyama et al., *Biosci. Biotechnol. Biochem.,* 68(2):352-359, 2004.
Myers, EPO 0273085
Natarajan et al., *J. Pl. Physiol.* (in press).
Nielsen et al., In: *Cellular and molecular biology of plant seed development*, Larkins and Vasil I K (Eds)., Kluwer Academic Publishers, Dordrecht, The Netherlands, 151-220, 1997.
Nielsen et al., *Plant Cell.,* 1:313-328, 1989.
Nishi et al., *J. Nutr.,* 133(2):352-357, 2003.
Orita et al., *Genomics,* 8(2):271-278, 1990.
PCT Appln. US93/06487
PCT Appln. WO93/19181
PCT Appln. WO96/30517
Pen et al., *Bio/Technology,* 10:292, 1992.
Poehlman and Sleper, In: *Breeding Field Crops*, Iowa State University Press, Ames, 1995
Przibila et al., *Plant Cell,* 3:169, 1991.
Reiter et al., *Proc. Natl. Acad. Sci. USA,* 89(4):1477-1481, 1992.
Shah et al., *Science,* 233:478, 1986.
Shanmugasundaram and Tsou, *Crop Sci.,* 18:598-601, 1978.
Shibata et al., *J. Biol. Chem.,* 262:10080-10085, 1987.
Shibata et al., *J. Biol. Chem.,* 263:6816-6821, 1988.
Shibles et al., In: *Crop Physiology, Some Case Histories*, Evans (ed), Cambridge Univ. Press, Cambridge, England, 51-189, 1975.
Shiroza et al., *J. Bacteol.,* 170:810, 1988.
Simmonds, In: *Principles of crop improvement*, Longman, Inc., NY, 369-399, 1979.
Sneep and Hendriksen, In: *Plant breeding perspectives*, Wageningen (ed), Center for Agricultural Publishing and Documentation, 1979.
Søgaard et al., *J. Biol. Chem.,* 268(30):22480-22484, 1993.
Sommer et al., *Biotechniques,* 12(1):82-87, 1992.
Stalker et al., *Science,* 242:419-423, 1988.
Steinmetz et al., *Mol. Gen. Genet.,* 20:220, 1985.
Utsumi, In: *Advances in Food and Nutrition Research*, Kinsella (Ed.), 36:89-208, Academic Press, San Diego, Calif., 1992.
Vanden Elzen et al., *Plant Mol. Biol.,* 5:299, 1985.
Wright et al., *Plant Cell Reports,* 5:150-154, 1986.
Yenofsky et al., *Mol. Gen. Genet.,* 211:215-222, 1988.

What is claimed is:

1. A method of predicting the phenotype of a soybean plant for glycinin and β-conglycinin content, said method comprising assaying the soybean plant for the presence of a non-transgenic mutant Gy1 allele comprising a deletion of the Gy1 allele found in line B2G2, a representative sample of seeds thereof is deposited under ATCC Accession No. PTA-6893;

assaying the soybean plant for the presence of a non-transgenic mutant Gy2 allele comprising a deletion of the Gy2 allele found in line B2G2; or assaying the soybean plant for the presence of a non-transgenic mutant Gy3 allele selected from the group consisting of an insertion at position 848-851, a single nucleotide polymorphism (SNP) at position 1083, a SNP at position 1120, and a SNP at position or 1866; wherein the position is the position in said allele corresponding to SEQ ID NO:164;

wherein the soybean plant comprising the non-transgenic mutant Gy1, Gy2, Gy3, or Gy4 allele comprises decreased glycinin and increased β-conglycinin content relative to a soybean plant that does not comprise the non-transgenic mutant Gy1, Gy2, Gy3, or Gy4 allele.

2. A method of plant breeding, said method comprising the steps of:

(a) assaying soybean plants for the presence of a non-transgenic mutant Gy1 allele comprising a deletion of the Gy1 allele found in line B2G2, a representative sample of seeds thereof is deposited under ATCC Accession No. PTA-6893;

assaying the soybean plant for the presence of a non-transgenic mutant Gy2 allele comprising a deletion of the Gy2 allele found in line B2G2; or assaying the soybean plant for the presence of a non-transgenic mutant Gy3 allele selected from the group consisting of an insertion at position 848-851, a single nucleotide polymorphism (SNP) at position 1083, a SNP at position 1120, and a SNP at position or 1866; wherein the position is the position in said allele corresponding to SEQ ID NO:164;

(b) selecting at least a first soybean plant comprising the Gy1, Gy2, Gy3, or Gy4 allele; and (c) crossing the first soybean plant to a second soybean plant to generate a progeny plant comprising the Gy1, Gy2, Gy3, or Gy4 allele that confers decreased glycinin and increased β-conglycinin content.

3. The method of claim 2, further comprising the step of: (d) repeating steps (a)-(c) with the progeny plant of step (c) as starting material at least about 2-10 times to produce additional progeny plants.

4. The method of claim 2, wherein the second soybean plant has a commercially significant yield.

5. The method of claim 4, further comprising selecting a progeny plant comprising said commercially significant yield.

6. The method of claim 2, comprising assaying the soybean plant for the presence of the mutant Gy1 allele comprising a deletion of the Gy1 allele found in line B2G2.

7. The method of claim 4, further comprising assaying the soybean plant for the presence of a non-transgenic mutant Gy4 allele, wherein the mutant Gy4 allele comprises a point mutation that abrogates the translation initiation codon.

8. The method of claim 2, wherein the first soybean plant is homozygous for said polymorphism.

9. The method of claim 2, wherein the first soybean plant comprises at least two polymorphisms.

10. The method of claim 7, comprising assaying polymorphisms within 50 cM of Gy1 and Gy4 alleles.

11. The method of claim 7, comprising assaying polymorphisms within 50 cM of Gy2 and Gy4 alleles.

12. The method of claim 7, comprising assaying the soybean plant for the presence of a non-transgenic mutant Gy4 allele corresponding to nucleotide 682 of SEQ ID NO:165.

13. The method of claim 2, wherein the first soybean plant comprises at least three polymorphisms.

14. The method of claim 2, wherein selecting the first soybean plant comprises detecting at least a first polymorphism in the Gy3 allele selected from the group consisting of an insertion at position 848-851, a single nucleotide polymorphism (SNP) at position 1083, a SNP at position 1120, and a SNP at position or 1866; wherein the position is the position in said allele corresponding to SEQ ID NO:164.

15. The method of claim 2, further comprising assaying the soybean plants for the presence of a non-transgenic mutant Gy5 allele.

16. The method of claim 15, wherein selecting the plant comprises detecting at least a first polymorphism in the Gy5 allele selected from the group consisting of a single nucleotide polymorphism (SNP) at position 363, a SNP at position 612, a deletion at positions 447-453 and a deletion at positions 519-524, wherein the position is the position in said allele corresponding to SEQ ID NO:166.

17. The method of claim 2, comprising detecting marker NS0199002 using primers or probes selected from the group consisting of primers or probes comprising the sequence of SEQ ID NO:137-140;

detecting marker NS0199003 using primers or probes selected from the group consisting of primers or probes comprising the sequence of SEQ ID NO149-152; or detecting marker NS0199008 using primers or probes selected from the group consisting of primers or probes comprising the sequence of SEQ ID NO:129-132.

18. The method of claim 2, wherein the first soybean plant comprises a polymorphism within 50 cM of a non-transgenic mutant lox2 allele.

19. The method of claim 18, wherein the polymorphism comprises a polymorphism in the lox2 allele selected from the group consisting of a single nucleotide polymorphism (SNP) at position 323, a SNP at position 439, a SNP at position 1390, a SNP at position 1431, a SNP at position 1458, a deletion at positions 2486-2487 and a SNP at position 2542; wherein the position is the position in said allele corresponding to SEQ ID NO:158.

20. The method of claim 2, wherein assaying soybean plants for a polymorphism comprises polymerase chain reaction (PCR).

21. The method of claim 2, wherein the polymorphism is detected by hybridization with a labeled nucleotide probe.

22. The method of claim 2, wherein the polymorphism is detected by DNA sequencing.

23. The method of claim 2, wherein step (a) further comprises assaying soybean plants for the presence of at least a first polymorphism in a soybean plant genomic region within 50 cM of a Kunitz Trypsin Inhibitor (KTI) null allele.

24. The method of claim 2, wherein selecting at least a first soybean plant in step (b) further comprises selecting a first soybean plant comprising a polymorphism within 50 cM of Kunitz Trypsin Inhibitor (KTI) null allele to select said null allele.

25. The method of claim 23, wherein the polymorphism within 50 cM of Kunitz Trypsin Inhibitor (KTI) null allele is selected from the group consisting of a 2-bp deletion at position 622-623 and a mutation at position 624, wherein the position is the position in said allele corresponding to SEQ ID NO:167.

26. The method of claim 23, wherein assaying soybean plants for a polymorphism comprises PCR.

27. The method of claim 23, wherein the polymorphism is detected by hybridization with a labeled nucleotide probe.

28. The method of claim 23, wherein the polymorphism is detected by DNA sequencing.

* * * * *